(12) United States Patent
Shaw et al.

(10) Patent No.: US 12,171,799 B2
(45) Date of Patent: *Dec. 24, 2024

(54) BOYSENBERRY, APPLE, AND BLACKCURRANT COMPOSITIONS AND METHODS OF PREPARATION AND USE THEREFOR

(71) Applicants: Odette M. Shaw, Palmerston North (NZ); Roger D. Hurst, Palmerston North (NZ)

(72) Inventors: Odette M. Shaw, Palmerston North (NZ); Roger D. Hurst, Palmerston North (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,390

(22) Filed: Feb. 22, 2023

(65) Prior Publication Data
US 2023/0277614 A1 Sep. 7, 2023

Related U.S. Application Data

(62) Division of application No. 16/635,609, filed as application No. PCT/NZ2018/050109 on Aug. 8, 2018, now Pat. No. 11,617,776.

(30) Foreign Application Priority Data

Aug. 8, 2017 (NZ) ...................................... 734440

(51) Int. Cl.
| | |
|---|---|
| A61K 36/73 | (2006.01) |
| A23L 2/02 | (2006.01) |
| A23L 33/00 | (2016.01) |
| A23L 33/105 | (2016.01) |
| A61K 31/05 | (2006.01) |
| A61K 31/352 | (2006.01) |
| A61K 36/185 | (2006.01) |
| A61K 45/06 | (2006.01) |
| A61P 11/00 | (2006.01) |

(52) U.S. Cl.
CPC ............... *A61K 36/73* (2013.01); *A23L 2/02* (2013.01); *A23L 33/105* (2016.08); *A23L 33/30* (2016.08); *A61K 31/05* (2013.01); *A61K 31/352* (2013.01); *A61K 36/185* (2013.01); *A61K 45/06* (2013.01); *A61P 11/00* (2018.01); *A23V 2002/00* (2013.01)

(58) Field of Classification Search
None
See application file for complete search history.

(56) References Cited

U.S. PATENT DOCUMENTS

2006/0024397 A9 2/2006 Nair et al.

FOREIGN PATENT DOCUMENTS

| | | |
|---|---|---|
| CN | 105901686 A | 8/2016 |
| DE | 102004052882 A1 | 5/2006 |
| KR | 2002-0042652 A | 6/2002 |
| WO | WO 2000/025723 A2 | 5/2000 |
| WO | WO 2001/015553 A1 | 3/2001 |
| WO | WO 2010/003787 A1 | 1/2010 |
| WO | WO 2010/082205 A1 | 7/2010 |

OTHER PUBLICATIONS

"100% Juice Variety Pack" Mintel GNPD database, Record ID:892269, Costco Wholesale, Kirkland Signature Hansen's Natural Juice Blast, USA, Ingredients: "Berry Blaze", published on Apr. 2008, 3 pages; Retrieved from http://www.gnpd.com/.
International Search Report and Written Opinion issued in PCT/NZ2018/050109, dated Oct. 12, 2018.
International Preliminary Report on Patentability and Written Opinion issued in PCT/NZ2018/050109, dated Feb. 20, 2020.
Wallace et al., "No difference in fecal levels of bacteria or short chain fatty acids in humans, when consuming fruit juice beverages containing fruit fiber, fruit polyphenols, and their combination" Science Direct, Nutrition Research, vol. 35, 2015, pp. 23-34.
Shaw et al., "Boysenberry ingestion supports fibrolytic macrophages with the capacity to ameliorate chronic lung remodeling" Am. J. Physiol Lung Cell Mol. Physiol., vol. 311, 2016, pp. L628-L638.
"Berri Qi", [online] published Jan. 5, 2017. [retrieved on Sep. 25, 2018] Retrieved from: 6 Pages retrieved on May 29, 2020.
Stevenson, et al., "Polyphenolic phytochemicals-just antioxidants or much more?" Cellular and Molecular Life Sciences, vol. 64, No. 22, 2007, pp. 2900-2916.
Wada et al., "Antioxidant Activity and Phenolic Content of Oregon Caneberries" J. Agric. Food Chem., vol. 50, No. 12, XP002977676, 2002, pp. 3495-3500.
Nyanhanda, et al., "Plant-derived Foods for the Attenuation of Allergic Airway Inflammation" Current Pharmaceutical Design, vol. 20, No. 6, 2014, pp. 869-878.
Meng-Jing Bao et al, "Apple polyphenol protects against cigarette smoke-induced acute lung injury," Nutrition 29 (2013) pp. 235-243.

*Primary Examiner* — Michael V Meller
(74) *Attorney, Agent, or Firm* — BakerHostetler

(57) ABSTRACT

The present disclosure encompasses compositions prepared from Boysenberry and apple, as well as compositions prepared from Boysenberry, apple and blackcurrant. Also encompassed are methods of preparing these compositions and methods of using these compositions, in particular, for treating or preventing disorders of the respiratory system, including amongst others: inflammation, asthma, chronic obstructive pulmonary disease, allergic airways inflammation, reactive airway disease, airway fibrosis, and airway remodelling.

15 Claims, 25 Drawing Sheets

FIG. 1A
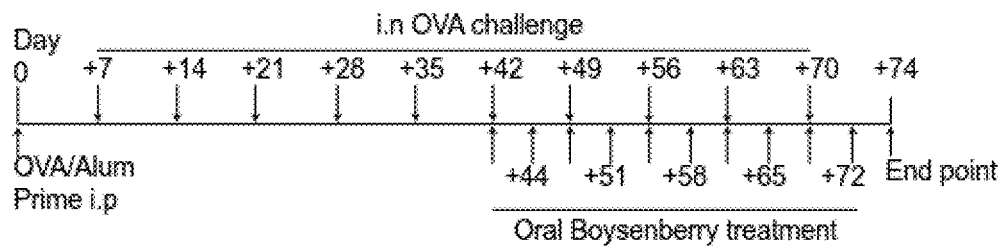
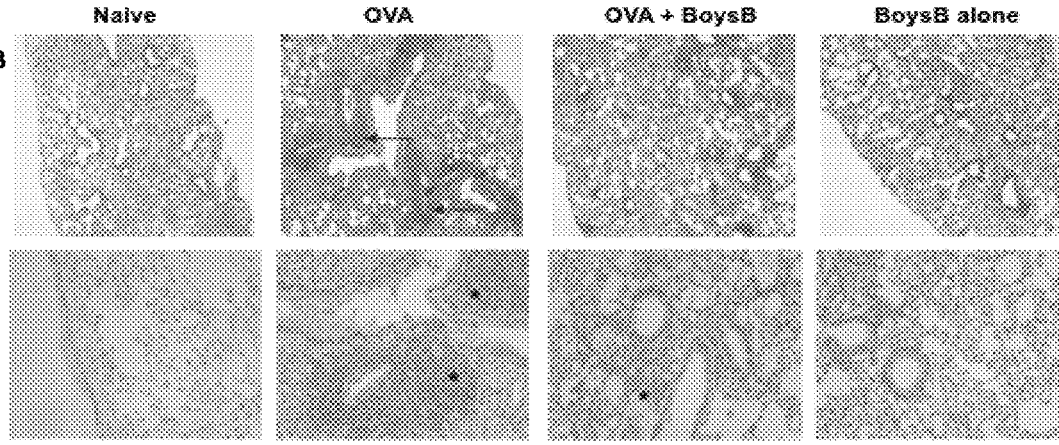
FIG. 1B
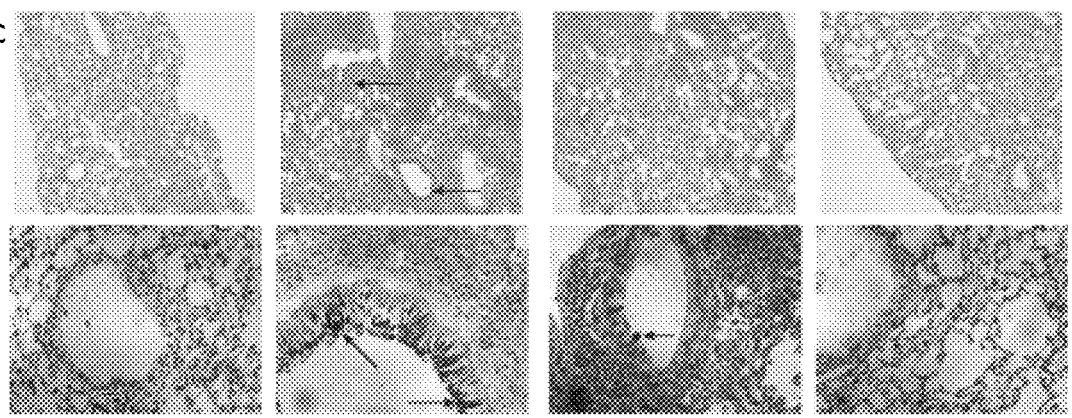
FIG. 1C
FIG. 1D
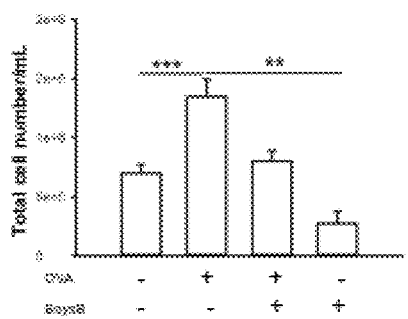
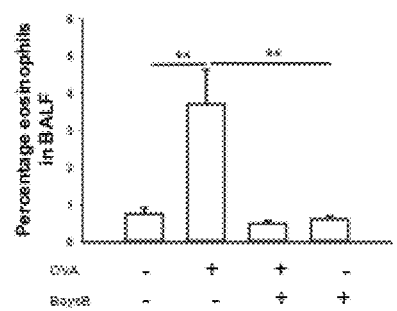

FIG. 4A
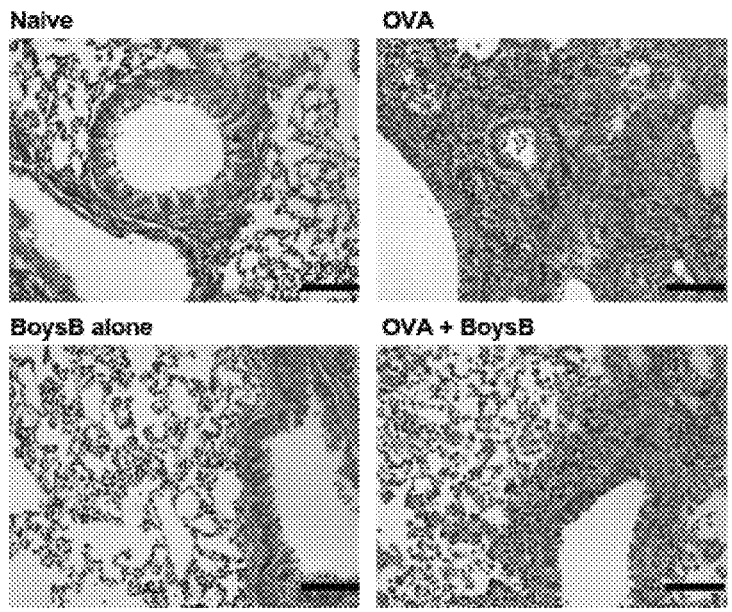
FIG 4B
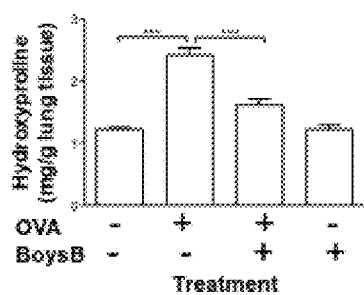
FIG. 4D
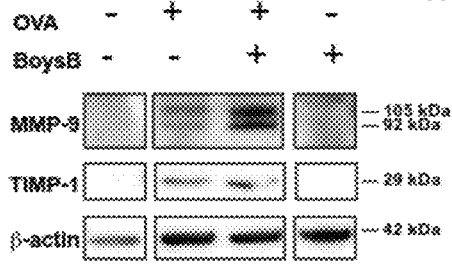
FIG. 4C
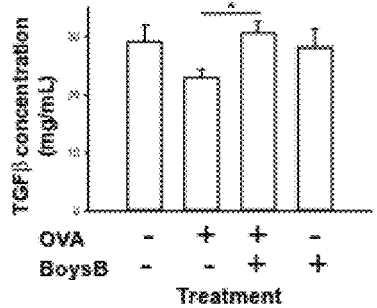
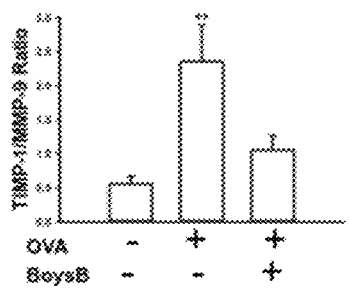
FIG. 4E FIG. 7A
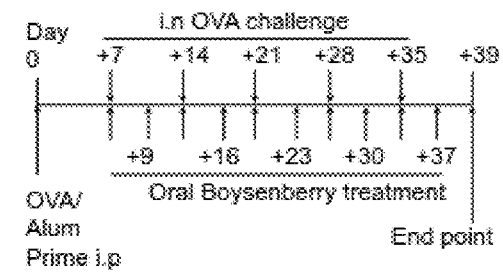
FIG. 7B
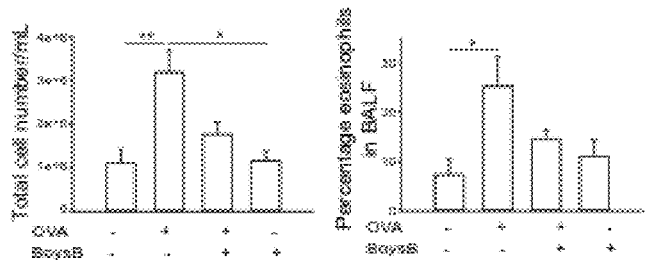
FIG. 7C
FIG. 7D
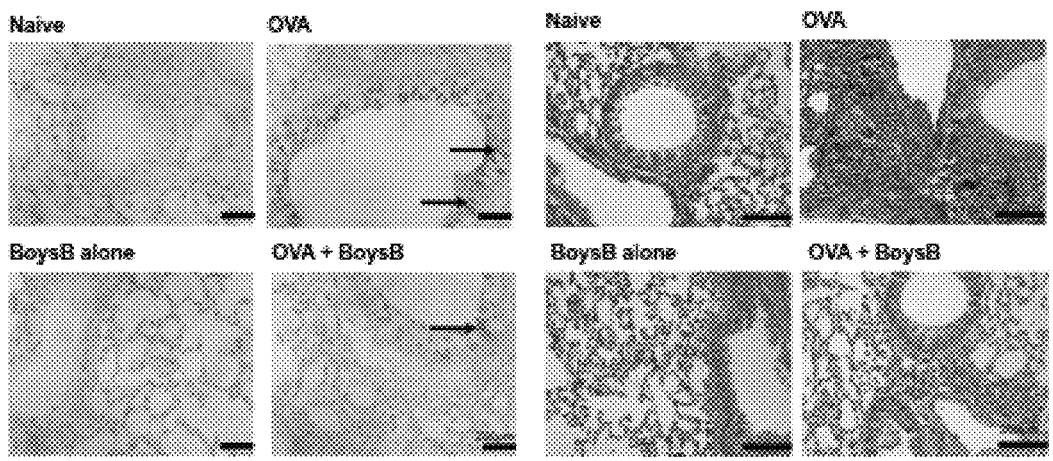
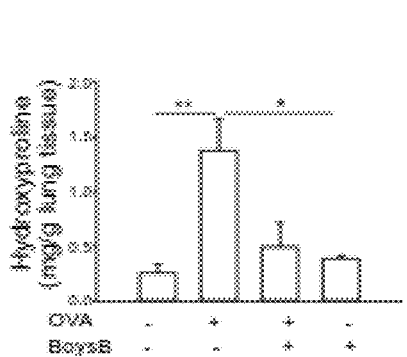
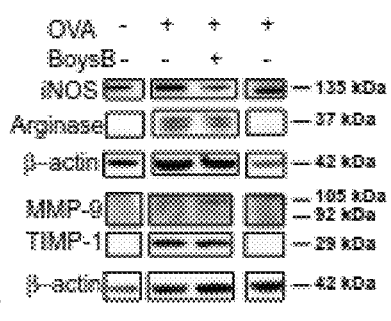
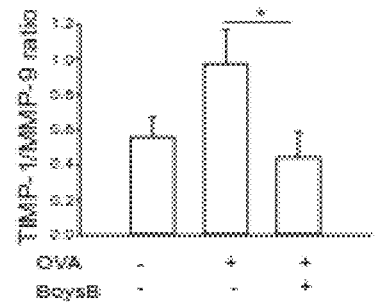
FIG. 7E
FIG. 7F
FIG. 7G

FIG. 12
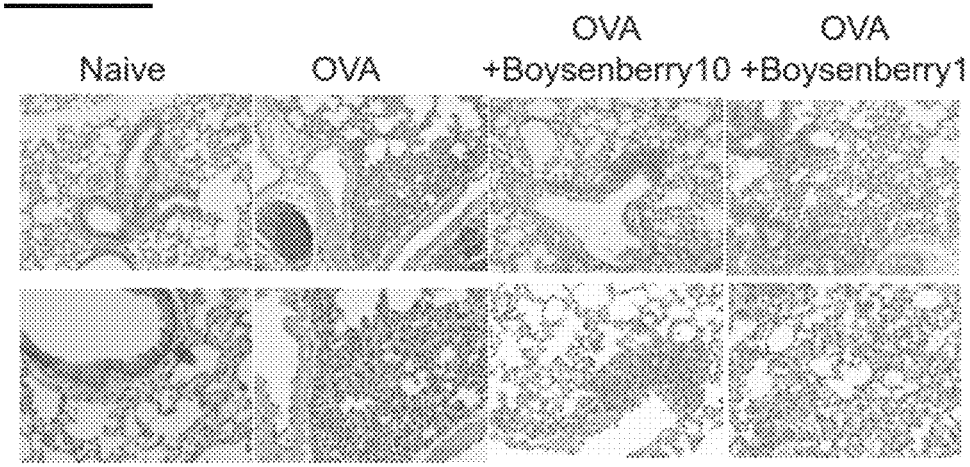
Naive | OVA | OVA +Boysenberry10 | OVA +Boysenberry1
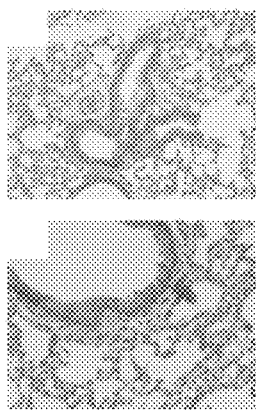
FIG. 13A
Naïve
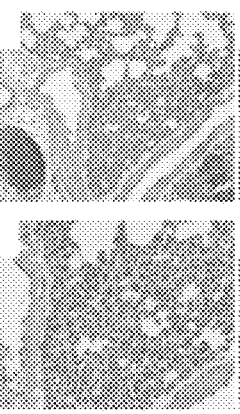
FIG. 13B
+OVA
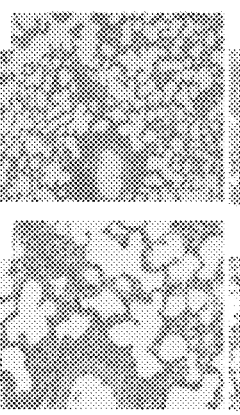
FIG. 13C
OVA +BerriQi™ Boysenberry with apple 10
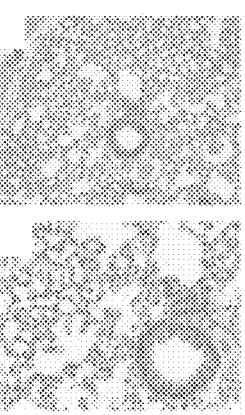
FIG. 13D
OVA +BerriQi™ Boysenberry with apple 1
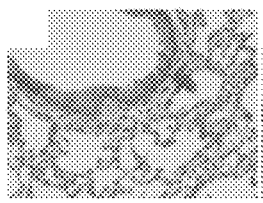
FIG. 13E
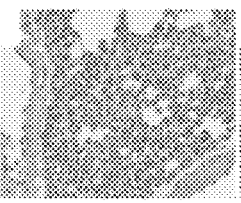
FIG. 13F
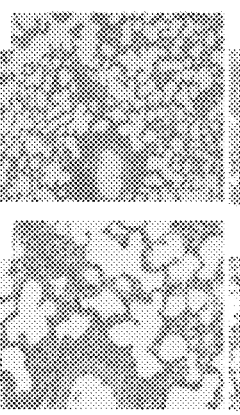
FIG. 13G
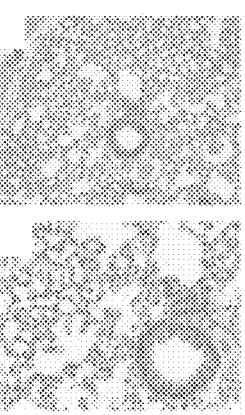
FIG. 13H

FIG. 18
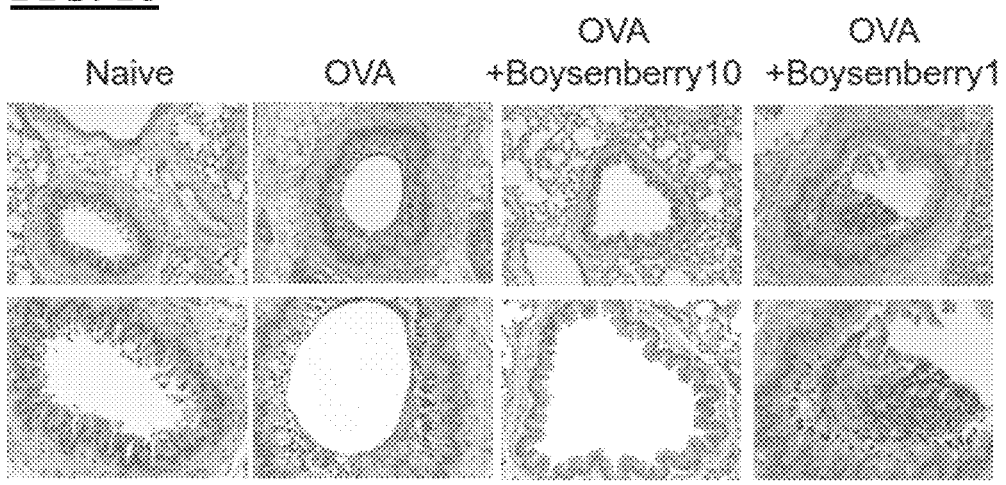
| FIG. 19A | FIG. 19B | FIG. 19C | FIG. 19D |
|---|---|---|---|
| Naïve | +OVA | OVA +BerriQi™ Boysenberry with apple 10 | OVA +BerriQi™ Boysenberry with apple 1 |
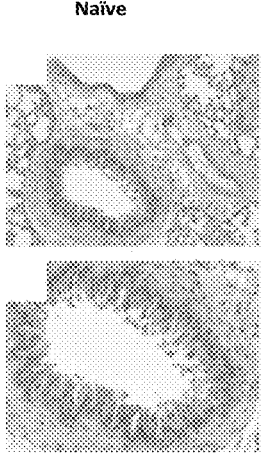 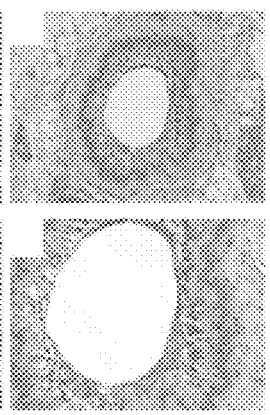 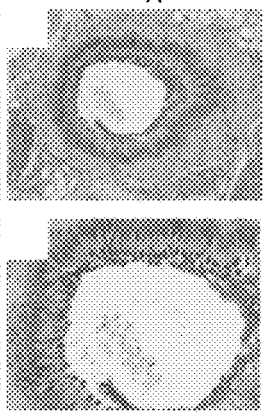 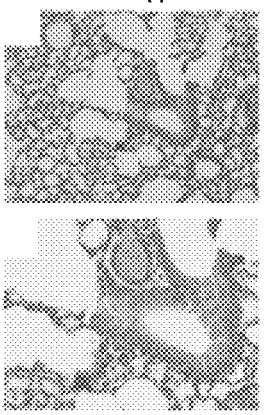
FIG. 19E     FIG. 19F     FIG. 19G     FIG. 19H

FIG. 20
Naïve    OVA    OVA+Apple10    OVA+Apple1
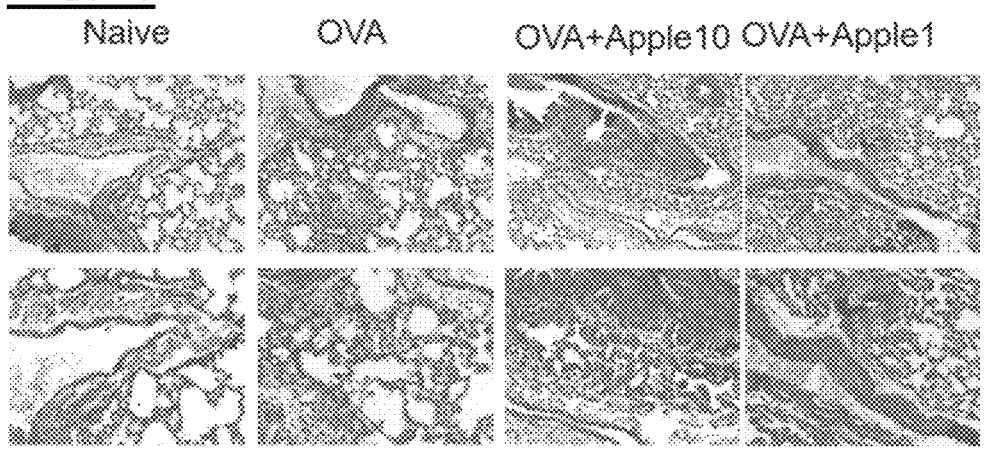
FIG. 21
Naïve    OVA    OVA+Boysenberry10    OVA+Boysenberry1
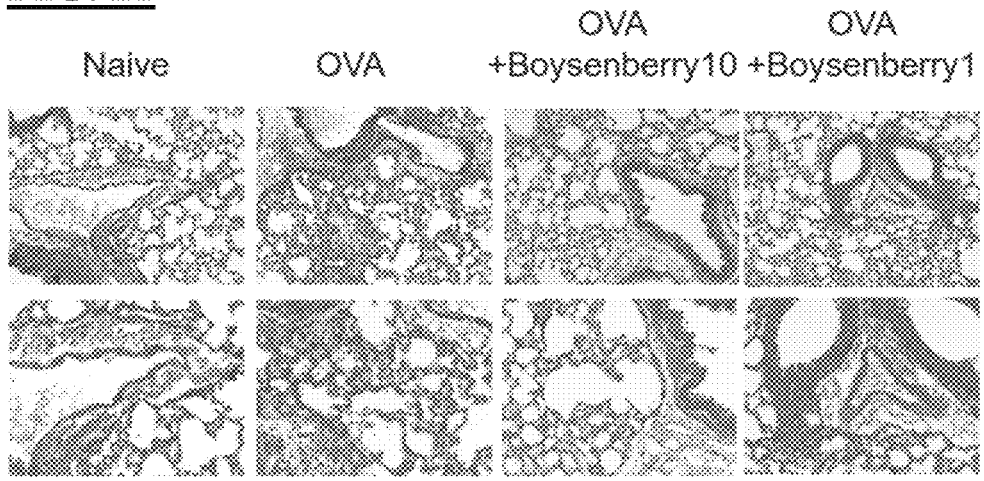
| FIG. 22A | FIG. 22B | FIG. 22C | FIG. 22D |
|---|---|---|---|
| Naïve | +OVA | OVA +BerriQi™ Boysenberry with apple 10 | OVA +BerriQi™ Boysenberry with apple 1 |
 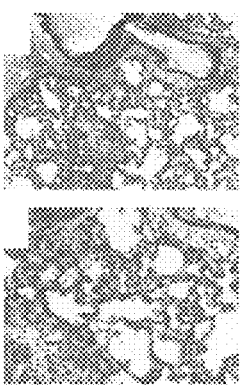 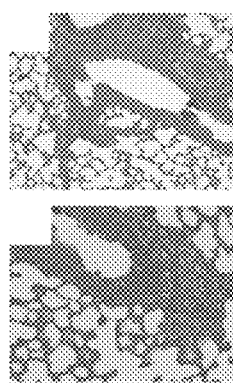 
FIG. 22E    FIG. 22F    FIG. 22G    FIG. 22H

BOYSENBERRY, APPLE, AND BLACKCURRANT COMPOSITIONS AND METHODS OF PREPARATION AND USE THEREFOR

CROSS-REFERENCE TO RELATED APPLICATIONS

This application is a divisional of U.S. patent application Ser. No. 16/635,609, filed Jan. 31, 2020, which is the National Stage Application of International Patent Application No. PCT/NZ2018/050109 filed Aug. 8, 2018, which claims the benefit of New Zealand Patent Application No. 734440 filed Aug. 8, 2017, the entire contents of which are incorporated herein by reference.

FIELD OF THE INVENTION

The present disclosure relates to compositions prepared from Boysenberry and apple, and compositions prepared from Boysenberry, apple and blackcurrant. The present disclosure relates also to methods of preparing such compositions, and methods of using such compositions, including methods of treating or preventing disorders of the respiratory tract, such as inflammatory conditions of the respiratory tract, including asthma, chronic obstructive pulmonary disease, allergic airways inflammation, reactive airway disease, airway fibrosis, and airway remodelling and the physiological conditions that lead to these conditions.

BACKGROUND OF THE INVENTION

Airway remodelling is understood as a progressive and irreversible decline in airway function due to chronic inflammatory processes that result in structural changes in the airway walls (67). Remodelling of the airways may involve all layers of the airway walls and can occur anywhere along the respiratory tract, from the large to the small airways. Remodelling leads to key changes in epithelial tissue (68). Damaged epithelial cells release profibrotic cytokines, including EGF and TGF-β, which leads to fibroblast proliferation, myofibroblast activation, and ultimately to the formation of subepithelial fibrosis (69). Airway smooth muscle hypertrophy and hyperplasia lead to an increase in airway wall thickness. In turn, this leads to accelerated lung function decline and irreversible or only partially reversible airflow obstruction.

Acute disorders causing airway inflammation include asthma and COPD. It is estimated that 150 million people are affected by asthma worldwide, with a 5-15% prevalence in children (61). The prevalence of COPD is estimated to be between 15-20%, and it is estimated to cause 2.75 million deaths per annum (86). In the case of chronic asthma there is evidence of cumulative tissue remodelling, fibrosis, and consequent loss of lung function (45, 59). Fibrosis and remodelling are also associated with COPD. Remodelling manifests as a progressive increase in symptoms such as dyspnoea and a corresponding decrease in bronchodilator responsiveness (67). Current asthma treatments are designed to manage inflammation and mitigate the symptoms and severity of asthma attacks (30, 43). COPD treatments are also designed to control inflammation and improve airflow. However, no asthma or COPD medications are known to prevent airway remodelling (70-74), and there are no current treatments available to prevent aberrant remodelling.

Asthma pathogenesis and lung tissue remodelling have been linked to an increase in profibrotic, arginase-positive, alternatively activated macrophages (AAMs) in the lung (27, 29, 34). However, temporal depletion of macrophage populations in a model of bleomycin-induced pulmonary fibrosis illustrates that lung macrophages may also develop fibrolytic functions that contribute toward the resolution of fibrosis (14).

Mediators of tissue remodelling, such as the matrix metalloproteinases (MMPs), play an important role in regulating fibrosis (5, 7, 8, 10, 38). Of these, MMP-9 is widely reported to increase in conditions of lung inflammation and fibrosis and is associated with improved symptoms in asthma sufferers (25, 32, 33). MMP-9, in concert with other MMPs, exerts fibrolytic activity that leads to the breakdown of denatured collagens that could moderate inappropriate lung remodelling (5, 60). As such, MMP-9 may represent a possible therapeutic target to limit lung damage in chronic asthma as well as other pulmonary diseases.

Large epidemiological studies have found that increased fruit and vegetable consumption correlates with reduced asthma symptoms (39, 46, 47). These population studies have identified foods high in polyphenols such as apples, pears (13, 51, 62), carrots, tomatoes (46-48), and citrus (11) as having inverse correlations with frequency and severity of reported asthma symptoms, in particular wheeze and cough symptoms (11, 13, 46, 47). However, the effect of fruits high in polyphenols on lung fibrosis and tissue remodelling is unknown. To date, no generally successful methods for preventing airway remodelling have been established.

Given the occurrence of respiratory disorders in the population, including allergic airways inflammation associated with asthma, COPD, reactive airway disease, airway fibrosis, and airway remodelling, there is a need for new compositions, particularly compositions derived from natural sources, for restoring and maintaining respiratory health.

SUMMARY OF THE INVENTION

In one aspect, the invention encompasses a method of treating or preventing inflammation in the respiratory tract, comprising: administering to a subject a composition comprising a Boysenberry and apple concentrate or a Boysenberry, apple and blackcurrant concentrate, thereby treating or preventing the inflammation in the respiratory tract in the subject.

Also encompassed is a composition, for example, a nutraceutical composition, comprising a Boysenberry and apple concentrate or a Boysenberry, apple and blackcurrant concentrate for treating or preventing inflammation in the respiratory tract in a subject.

In one other aspect, the invention encompasses a method of treating or preventing asthma, comprising: administering to a subject a composition comprising a Boysenberry and apple concentrate or a Boysenberry, apple and blackcurrant concentrate, thereby treating or preventing the asthma in the subject.

Also encompassed is a composition, for example, a nutraceutical composition, comprising a Boysenberry and apple concentrate or a Boysenberry, apple and blackcurrant concentrate for treating or preventing asthma in a subject.

In yet one other aspect, the invention encompasses a method of treating or preventing chronic obstructive pulmonary disease, comprising: administering to a subject a composition comprising a Boysenberry and apple concentrate or a Boysenberry, apple and blackcurrant concentrate, thereby treating or preventing the chronic obstructive pulmonary disease in the subject.

Also encompassed is a composition, for example, a nutraceutical composition, comprising a Boysenberry and apple concentrate or a Boysenberry, apple and blackcurrant concentrate for treating or preventing chronic obstructive pulmonary disease in a subject.

In still one other aspect, the invention encompasses a method of treating or preventing aberrant collagen deposition or fibrosis in the respiratory tract, comprising: administering to a subject a composition comprising a Boysenberry and apple concentrate or a Boysenberry, apple and blackcurrant concentrate, thereby treating or preventing the aberrant collagen deposition or fibrosis in the respiratory tract of the subject.

Also encompassed is a composition, for example, a nutraceutical composition, comprising a Boysenberry and apple concentrate or a Boysenberry, apple and blackcurrant concentrate for treating or preventing aberrant collagen deposition or fibrosis in a subject.

In even one other aspect, the invention encompasses a method of treating or preventing airway remodelling, comprising: administering to a subject a composition comprising a Boysenberry and apple concentrate or a Boysenberry, apple and blackcurrant concentrate, thereby treating or preventing the airway remodelling in the subject.

Also encompassed is a composition, for example, a nutraceutical composition, comprising a Boysenberry and apple concentrate or a Boysenberry, apple and blackcurrant concentrate for treating or preventing airway remodelling in a subject.

In various aspects:

The composition comprises Boysenberry juice concentrate, Boysenberry puree, or Boysenberry powder.

The composition comprises apple juice concentrate, apple puree, or apple powder.

The composition comprises blackcurrant juice concentrate, blackcurrant puree, or blackcurrant powder.

The composition comprises a dosage unit comprising about 5 to about 500 mg total anthocyanins.

For the nutraceutical composition comprising the Boysenberry and apple concentrate, the composition comprises a dosage unit comprising about 5 to about 500 mg total Boysenberry anthocyanins.

For the nutraceutical composition comprising the Boysenberry, apple and blackcurrant concentrate, the composition comprises a dosage unit comprising about 5 to about 500 mg total Boysenberry and blackcurrant anthocyanins.

The composition is formulated for enteral administration.

The composition is formulated for oral administration.

The composition is formulated as a syrup or as drops.

The composition is formulated as a gel or jelly.

The composition is formulated as a tablet or capsule.

The composition is formulated for administration at a dosage of about 0.1 mg/kg to about 10 mg/kg total anthocyanins/subject's body weight.

For the nutraceutical composition comprising the Boysenberry and apple concentrate, the composition is formulated for administration at a dosage of about 0.1 mg/kg to about 10 mg/kg total Boysenberry anthocyanins/subject's body weight.

For the nutraceutical composition comprising the Boysenberry, apple and blackcurrant concentrate, the composition is formulated for administration at a dosage of about 0.1 mg/kg to about 10 mg/kg total Boysenberry and blackcurrant anthocyanins/subject's body weight.

The composition is formulated for administration at a dosage of about 10 mg to about 1000 mg total anthocyanins per day.

For the nutraceutical composition comprising the Boysenberry and apple concentrate, the composition is formulated for administration at a dosage or about 10 mg to about 1000 mg total Boysenberry anthocyanins per day.

For the nutraceutical composition comprising the Boysenberry, apple and blackcurrant concentrate, the composition is formulated for administration at a dosage of or about 10 mg to about 1000 mg total Boysenberry and blackcurrant anthocyanins per day.

Alternatively, the dosage is about 10 mg to about 200 mg total anthocyanins per day, or about 50 mg total anthocyanins per day.

For the nutraceutical composition comprising the Boysenberry and apple concentrate, the dosage is about 10 mg to about 200 mg total Boysenberry anthocyanins per day, or about 50 mg total Boysenberry anthocyanins per day.

For the nutraceutical composition comprising the Boysenberry, apple and blackcurrant concentrate, the dosage is about 10 mg to about 200 mg total Boysenberry and blackcurrant anthocyanins per day, or about 50 mg total Boysenberry and blackcurrant anthocyanins per day.

The composition comprises added polyphenols.

The composition is formulated for co-administration with a further respiratory aid.

The composition is formulated for co-administration with one or more treatments for a chronic respiratory disorder.

The inflammation is associated with a chronic respiratory disorder.

The inflammation is associated with one or more of: asthma, chronic obstructive pulmonary disease, allergic airways inflammation, reactive airway disease, airway fibrosis, and airway remodelling.

The asthma is atopic or non-atopic.

The asthma is associated with airway fibrosis or airway remodelling.

The chronic obstructive pulmonary disease is associated with smoking or pollution.

The chronic obstructive pulmonary disease is associated with airway fibrosis or airway remodelling.

The aberrant collagen deposition or the fibrosis is associated with a chronic respiratory disorder.

The aberrant collagen deposition or the fibrosis is associated with asthma or chronic obstructive pulmonary disease.

The airway remodelling is associated with a chronic respiratory disorder.

The airway remodelling is associated with one or more of: asthma and chronic obstructive pulmonary disease.

In still one further aspect, the invention comprises the use of a composition comprising a Boysenberry and apple concentrate or a Boysenberry, apple and blackcurrant concentrate for preparing a nutraceutical composition for:

(i) treating or preventing inflammation in a respiratory tract in a subject;
(ii) treating or preventing asthma in a subject;
(iii) treating or preventing chronic obstructive pulmonary disease in a subject;
(iv) treating or preventing allergic airways inflammation in a subject;
(v) treating or preventing reactive airway disease in a subject;
(vi) treating or preventing aberrant collagen deposition in a subject;
(vii) treating or preventing fibrosis in a respiratory tract in a subject;
(viii) treating or preventing airway remodelling in a subject.

In various aspects, the therapeutic use employs the compositions, dosages, and formulations, and relates to the various conditions, as noted above.

The foregoing brief summary broadly describes the features and technical advantages of certain embodiments of the present invention. Further technical advantages will be described in the detailed description of the invention and examples that follows. Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to limit the invention's scope.

BRIEF DESCRIPTION OF THE DRAWINGS

FIGS. 1A-1D. Therapeutic oral Boysenberry treatment reduces OVA-induced chronic lung inflammation. FIG. 1A: 6-week-old male C57Bl/6 mice (n=10 per group) were primed i.p. with OVA/alum (day 0) then challenged i.n. with OVA every 7 days for 10 weeks. From weeks 6 to 10 Boysenberry juice was administered orally (gavage) 1 h prior to, and 2 days after, each i.n. OVA challenge. FIG. 1B: representative H&E staining of lung tissue from naive, 10-week OVA challenge only (OVA), 10-week OVA challenge with therapeutic Boysenberry (OVA BoysB) treatment, and Boysenberry alone (BoysB)-treated mice. Arrows and * indicate immune cell infiltrate. Magnification ×4 (top) and ×10 (bottom). FIG. 1C: representative AB-PAS staining of lung tissue. Arrows indicate dark purple mucus-positive bronchioles. Magnification ×4 (top) and ×20 (bottom). FIG. 1D: total cells per ml BALF and flow cytometric quantification of percentage of eosinophils in BALF following final OVA challenge. P<0.01, *P<0.001 (n=10 per group) one-way ANOVA with Tukey's post hoc test compared with naive and OVA challenge with therapeutic Boysenberry treatment and Boysenberry alone-treated mice.

FIG. 2A: representative H&E staining of lung tissue from 10-week OVA-challenged mice, with and without Boysenberry treatment. Arrows indicate macrophages. Magnification ×100, scale 200 μm. FIG. 2B: representative Western blot analysis of iNOS (135 kDa) and arginase (37 kDa) expression in lung tissue. Noncontiguous bands from the same Western blot are shown. FIGS. 2C and 2D: quantification of iNOS and arginase Western blot signals normalized to β-actin signal. **P<0.01 (n=10 per group) one-way ANOVA with Tukey's post hoc test.

FIG. 3A: CD68+CD206+macrophages identified by *. FIG. 3B: CD206+arginase+macrophages identified by *. DAPI nuclear stain (dark blue). Magnification ×40, scale 200 μm.

FIGS. 4A-4E. Boysenberry treatment decreases collagen deposition and increases MMP-9 protein expression in lung tissue during OVA-induced chronic lung inflammation. FIG. 4A: representative Masson's trichrome staining. Magnification ×40, scale 200 μm. FIG. 4B: hydroxyproline levels (mg/g lung tissue); ***P<0.001 (n=10) one-way ANOVA with Tukey's post hoc test. FIG. 4C: lung TGFβ concentration as determined by ELISA; *P 0.05 (n 10 per group) one-way ANOVA with Tukey's post hoc test. FIG. 4D: Western blot analysis of MMP-9 (pro 105 kDa; active 92 kDa) and TIMP-1 (29 kDa) expression (noncontiguous bands from the same Western blot are shown) in lung tissue from 10-week OVA-challenged mice with and without Boysenberry treatment. FIG. 4E: ratio of TIMP-1/MMP-9 protein expression normalized to β-actin loading control; **P<0.01 (n=10) one-way ANOVA with Tukey's post hoc test compared with naive and OVA plus Boysenberry treatment.

FIG. 5A: DAB labelling of MMP-9+macrophages (arrows). FIG. 5B: immunofluorescent labelling of CD206+MMP-9+macrophages (*). DAPI nuclear stain (dark blue). Magnification ×40, scale 200 μm.

FIG. 6A: 6-week-old male C57Bl/6 mice (n=10 per group) were primed i.p. with OVA/alum (day 0) then challenged i.n. with OVA every 7 days for 5 weeks. From weeks 6 to 7 macrophages were depleted using clodronate liposomes (CloLip) the day before Boysenberry juice was administered orally (gavage). FIG. 6B: flow cytometric quantification of percentage of macrophages in BALF following final clodronate macrophage depletion; *P<0.05 (n=10 per group) one-way ANOVA with Tukey's post hoc test. FIG. 6C: hydroxyproline levels (mg/g lung tissue) in the lung; *P<0.05 (n=10 per group) one-way ANOVA with Tukey's post hoc test.

FIGS. 7A-7G. Prophylactic oral Boysenberry treatment reduces OVA-induced chronic lung inflammation and collagen deposition. FIG. 7A: 6-week-old male C57Bl/6 mice (n=10 per group) were primed i.p. with OVA/alum then challenged i.n. with OVA every 7 days for 5 weeks. Boysenberry juice was administered orally (gavage) 1 h prior and 2 days after each i.n. OVA challenge. FIG. 7B: lung tissue was stained with total cells per ml BALF and flow cytometric quantification of percentage of eosinophils in BALF following final OVA challenge; *P<0.05, **P<0.01 (n=10 per group) one-way ANOVA with Tukey's post hoc test. FIG. 7C: AB-PAS, dark purple mucus-positive bronchioles (arrows); magnification ×20, scale 200 μm. FIG. 7D: Masson's trichrome; magnification ×40, scale 200 μm. FIG. 7E: hydroxyproline levels (mg/g lung tissue) in the lung. *P<0.05, **P<0.01 (n=10 per group) one-way ANOVA with Tukey's post hoc test. FIG. 7F: Western blot analysis of iNOS, arginase, MMP-9, and TIMP-1 lung tissue. Noncontiguous bands from the same Western blot are shown. FIG. 7G: ratio of TIMP-1/MMP-9 protein levels normalized to β-actin loading control. *P<0.05, (n=10 per group) one-way ANOVA with Tukey's post hoc test.

FIG. 12. Treatment utilising BerriQi™ Boysenberry with apple administration in model of acute allergic airways inflammation. Haematoxylin and eosin staining of lung tissues following Boysenberry treatment.

FIGS. 13A-13H. Treatment utilising BerriQi™ Boysenberry with apple administration in model of acute allergic airways inflammation. Haematoxylin and eosin staining of lung tissues following BerriQi™ Boysenberry with apple treatment. Representative 10× (FIGS. 13A-13D) and 20× (FIGS. 13E-13H) images of (FIG. 13A, FIG. 13E) naïve, (FIG. 13B, FIG. 13F) OVA, (FIG. 13C, FIG. 13G) BerriQi™ Boysenberry with apple 10, and (FIG. 13D, FIG. 13H) BerriQi™ Boysenberry with apple 1. Immune cells appear as dark pink/purple clusters.

FIG. 18. Treatment utilising BerriQi™ Boysenberry with apple administration in model of acute allergic airways inflammation. Alcian blue/periodic acid Schiff diastase staining of lung tissues following Boysenberry treatment.

FIGS. 19A-19H. Treatment utilising BerriQi™ Boysenberry with apple administration in model of acute allergic airways inflammation. Alcian blue/periodic acid Schiff diastase staining of lung tissues following BerriQi™ Boysenberry with apple treatment. Representative 10× (FIGS. 19A-19D) and 20× (FIGS. 19E-19H) images of images of (FIG. 19A, FIG. 19E) naïve, (FIG. 19B, FIG. 19F) OVA, (FIG. 19C, FIG. 19G) BerriQi™ Boysenberry with apple 10, and (FIG. 19D, FIG. 19H) BerriQi™ Boysenberry with apple 1. Mucous positive goblet cells are dark purple.

FIG. 20. Treatment utilising BerriQi™ Boysenberry with apple administration in model of acute allergic airways inflammation. Masson's trichrome staining of lung tissues following apple treatment.

FIG. 21. Treatment utilising BerriQi™ Boysenberry with apple administration in model of acute allergic airways inflammation. Masson's trichrome staining of lung tissues following Boysenberry treatment.

FIGS. 22A-22H. Treatment utilising BerriQi™ Boysenberry with apple administration in model of acute allergic airways inflammation. Masson's trichrome staining of lung tissues following BerriQi™ Boysenberry with apple treatment. Representative 10× (FIGS. 22A-22D) and 20× (FIGS. 22E-22H) images of images of (FIG. 22A, FIG. 22E) naïve, (FIG. 22B, FIG. 22F) OVA, (FIG. 22C, FIG. 22G) BerriQi™ Boysenberry with apple 10, and (FIG. 22D, FIG. 22H) BerriQi™ Boysenberry with apple 1.

DETAILED DESCRIPTION OF THE INVENTION

Figure 2A:
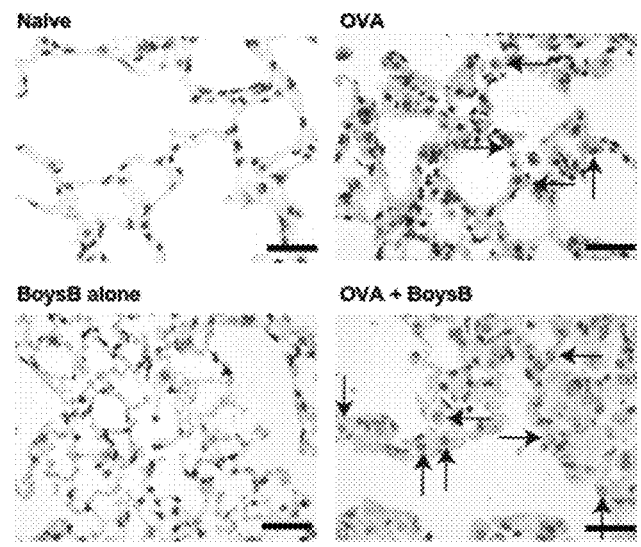
FIGS. 2A-2D. Boysenberry treatment increases arginase expression and macrophage accumulation in lung tissue during OVA-induced chronic lung inflammation.

The following description sets forth numerous exemplary configurations, parameters, and the like. It should be recognised, however, that such description is not intended as a limitation on the scope of the present invention, but is instead provided as a description of exemplary embodiments.

All references, including patents and patent applications, cited in this specification are hereby incorporated by reference. No admission is made that any reference constitutes prior art. Nor does discussion of any reference constitute an admission that such reference forms part of the common general knowledge in the art, in New Zealand or in any other country.

Definitions

In each instance herein, in descriptions, embodiments, and examples of the present invention, the terms "comprising", "including", etc., are to be read expansively, without limitation. Thus, unless the context clearly requires otherwise, throughout the description and the claims, the words "comprise", "comprising", and the like are to be construed in an inclusive sense as to opposed to an exclusive sense, that is to say in the sense of "including but not limited to".

The term "consisting essentially of", as used herein, may refer to the presence of a concentrate in a composition. For example, the concentrate may be at least 80% by weight of the composition, or at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.8%, or at least 99.9% by weight of the composition (% w/w). For liquids, the concentrate may be at least 80% by volume of the composition volume, or at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.8%, or at least 99.9% by volume of the composition volume (% v/v).

In the present description, the articles "a" and "an" are used to refer to one or to more than one (i.e., to at least one) of the grammatical object of the article. By way of example, "an element" can be taken to mean one element or more than one element.

Throughout this description, the term "about" is used to indicate that a value includes the standard deviation of error for the method being employed to determine the value, for example, levels of compounds or dosage levels, as described in detail herein. In particular, the term "about" encompasses a 10% to 15% deviation (positive and negative) in the stated value or range, particularly 10% deviation (positive and negative) in the stated value or range.

"Airway remodelling", also referred to as tissue or lung remodelling, refers to the development of specific structural changes in the airway wall. This may include, for example, remodelling of the fibrous connective tissue in the lining of the airways, for example, in the lungs. Airway remodelling may include one or more of subepithelial fibrosis, myofibroblast accumulation, airway smooth muscle hyperplasia, and hypertrophy, mucous gland and goblet cell hyperplasia, and epithelial disruption. Symptoms may include decreased airway distensibility (i.e., stiffer airways), diminished elastic recoil, progressive decline in FEV1 (forced expiratory volume 1), and FVC (forced vital capacity), accelerated lung function decline, irreversible or only partially reversible airflow obstruction, dyspnoea, and decreased responsiveness to respiratory therapy (e.g., asthma or COPD therapeutics).

"Asthma" refers to an inflammatory disorder of the airways of the lungs, characterized by variable and recurring breathing impairment, including airflow obstruction and bronchospasm. Airflow obstruction may be defined as reduced FEV1 and/or reduced FEV1/VC ratio. The airflow obstruction in asthma may be reversible with or without medication. Symptoms of asthma may include one or more of wheezing, coughing, chest tightness or pain, and shortness of breath. Included herein are atopic (e.g., allergen or antigen induced) and non-atopic forms of asthma, as well as exercise-induced asthma, occupational asthma, aspirin-induced asthma, and alcohol-induced asthma.

A "respiratory aid" is a composition that assists with airway function or other aspects of the respiratory system, e.g., medicines, herbal compositions, essential oils, and various compositions for inhalation.

"Airway", "respiratory tract", and "respiratory system" refer to any of the organs, tissues, or cellular components involved in gas exchange (i.e., breathing). This includes the upper respiratory tract, trachea, bronchi, bronchioles, alveoli, lungs, pleura and pleural cavity, and the nerves and muscles of breathing. It will be understood that "airways" describes the various structural components (e.g., cellular components, tissues, and organs) as well as the space where gas exchange occurs.

"Apple" as used herein encompasses any fruit of the genus *Malus*, and any hybrid, variety, and genetic derivative thereof. Included, specifically, are *Malus pumila*, as well as the particular cultivars of 'Gala' 'Golden Supreme' 'McIntosh' 'Transparent' 'Primate' 'Sweet Bough' 'Duchess' 'Fuji' 'Jonagold' 'Golden Delicious' 'Red Delicious' 'Chenango' 'Gravenstein' 'McIntosh' 'Snow' 'Blenheim' 'Winesap' 'Granny Smith' 'King' 'Wagener' 'Swayzie' ' Greening' and 'Tolman Sweet'. Included also are the cultivars 'Alice' '*Ambrosia*' 'Ananasrenette' 'Aroma' 'Discovery' 'Envy' 'Braeburn' 'Bramley' 'Arkansas Black' 'Dougherty'/'Red Dougherty' 'Goldrenette'/'Reinette' 'Jazz' 'Jonagold' 'James Grieve' 'Yellow Transparent' 'Pacific rose' 'Lobo' 'Sampion'/'Shampion' 'Sonya' 'Splendour'/ 'Splendor' 'Summerred' 'Pink Lady' 'Belle de Boskoop' 'Cox Pomona' 'Cox's Orange Pippin' 'Kidd's Orange Red' and 'SugarBee'. Further included are the cultivars of 'Haralson' 'Wealthy' 'Honeygold' and 'Honeycrisp'. Included as well are crabapples, apple-crabapple hybrids, and cooking apples.

"Blackcurrant" as used herein encompasses any black/dark coloured *Ribes* fruit from the family Grossulariaceae, which includes but is not limited to that of *Ribes nigrum, Ribes nigrum* L., *Ribes americanum, Ribes hudsonianum, Ribes laxiflorum*, and *Ribes×nidigrolaria*. Any hybrid, variety, and genetic derivative of these are also included. Included amongst suitable blackcurrant cultivars are those of 'Andega', 'Ben Ard', 'Ben Alder', 'Ben Dorain', 'Ben Gairn', 'Ben Hope', 'Ben Lomand', 'Ben More', 'Ben Rua', 'Ben Sarek', 'Ben Tirran', 'Blackaddef', 'Black Down', 'Burga', 'Orcs', 'Magnus', 'Murchison', 'Sefton', 'Titania', 'Consort', 'Crusader', 'Geant de Boskoop', 'Noir de Bourgogne', 'Royal de Naples', 'Boskoop Giant', 'Tench', 'Tiben', 'Tines', 'Tisel', and 'Willoughby'.

"Boysenberry" as used herein encompasses a *Rubus* hybrid berry, which includes but is not limited to a berry obtained from the plant identified as *Rubus ursinus* var *loganobaccus* cv Boysenberry, *Rubus ursinus×Rubus idaeus, Rubus loganbaccus×baileyanus* Britt, and *Rubus idaeus×Rubus ulmifolius*. Generally speaking, a Boysenberry may be derived from a cross between raspberry and blackberry plants, or between raspberry, blackberry, and loganberry plants. Included are various Boysenberry hybrids, varieties, and genetic derivatives thereof. Boysenberries are referred to herein as berries or, more broadly, as fruits.

"Chronic obstructive pulmonary disease", or COPD, refers to a lung disorder associated with progressive obstruction of the airways and poor airflow. Airflow obstruction may be defined as a reduction in FEV1 and/or a reduction in FEV1/VC ratio. The airflow obstruction in chronic obstructive pulmonary disease may not be fully reversible. Symptoms include but are not limited to shortness of breath, cough, and sputum production (i.e., phlegm). COPD may be associated with smoking, air pollution, poorly ventilated cooking or heating fires. A genetic component may also be involved in COPD. The disorder is also known as chronic obstructive lung disease (COLD), chronic obstructive airway disease (COAD), chronic bronchitis, pulmonary emphysema, amongst other known terminology.

"Concentrate", for example, in relation to a Boysenberry, apple, or blackcurrant concentrate, or any combination thereof, refers to a composition where the liquid component (e.g., juice) has been partly or substantially removed. Removal of a liquid component may be by evaporation or any other means. A concentrate may be prepared, for example, as a puree, paste, or powder, or may be prepared from a Boysenberry, apple, or blackcurrant juice, or any combination thereof, e.g., prepared as a juice concentrate.

A "disorder" of respiratory tract includes a disease or other condition affecting any of the organs, tissues, or cellular components involved in gas exchange (i.e., breathing), as noted herein. The disorders may be an acute or chronic condition, such as inflammation and conditions that are associated with inflammation. Particular disorders of interest include asthma, chronic obstructive pulmonary disease, reactive airway disease, airway fibrosis, and airway remodelling. Other disorders are described in detail herein.

A "genetic derivative" of a plant refers to offspring, sports, or other cultivars that are obtained from the parent stock. This includes offspring obtained from a genetic cross with the parent, e.g., F1 progeny or F2 progeny. The term "genetic derivative" may refer to the derived plant, itself, or to its fruit.

"Fibrosis", as in airway or pulmonary fibrosis, refers to a disruption in the regulation of collagen and other extracellular matrix components in the respiratory tract. In the airways of patients with fibrosis, there may be increased extracellular matrix deposition, such as in the reticular basement membrane region, lamina propria, and/or submucosa. Scar formation and the accumulation of excess fibrous connective tissue leads to thickening of the airway walls. Symptoms may include reduced oxygen supply, shortness of breath, chronic cough, fatigue and/or weakness, chest discomfort including chest pain, loss of appetite, and weight loss. Included are idiopathic forms of airway fibrosis, as well as airway fibrosis associated with smoking, air pollution, connective tissue disease (e.g., rheumatoid arthritis, sarcoidosis, etc), infections, medications (e.g., methotrexate, bleomycin, etc), and radiation therapy.

"Inflammation" refers to a condition characterised by one or more of: vasodilation, heat, redness, discomfort, swelling, edema, lesions, fissures, ulcerations, leukocyte extravasation, and loss of function. Included are both acute and chronic forms of inflammation, such as acute airways inflammation, and other inflammatory disorders, e.g., autoimmune diseases or allergic conditions. Particularly included are asthma, chronic obstructive pulmonary disease, airway fibrosis, reactive airway disease, and airway remodeling. Other inflammatory disorders are described elsewhere in this document.

As noted herein, the terms "lyophilising" and "freeze drying" are used synonymously. It will be understood that the terms "freeze drying"/"lyophilising" do not exclude the use of higher temperatures (i.e., higher than freezing temperatures). For example, higher temperatures may be used for removing residual moisture during the secondary drying phase for lyophilisation/freeze drying procedures.

A "nutraceutical" refers to a standardised composition for administration to a subject. It may be a pharmaceutical grade composition, and may maintain or improve the health of a subject, or may treat or prevent one or more disorder in a subject.

"Reactive airway disease" refers to an inflammatory airway disorder characterised by reversible airway narrowing due to external stimuli. The term can encompass other known disorders such as asthma, chronic obstructive pulmonary disease, upper respiratory tract infections, etc, or can refer to conditions that are similar to these disorders but not directly diagnosed as such, e.g., having asthma-like syndrome or asthma-like symptoms. Subjects with reactive airway disease may show one or more symptoms of coughing, wheezing, or shortness of breath upon exposure to particular stimuli, for example, smoke, vapour, fume, or other irritants.

As used herein, a "subject" may be a human or non-human animal, particularly a mammal, including cattle, sheep, goats, pigs, horses, and other livestock, including, as well, dogs, cats, and other domesticated pets. In particular aspects, the subject is a human being.

"Treating" as used herein is meant as reducing, ameliorating, or resolving a disorder, for example a respiratory disorder, such as a disease or other condition of the respiratory system. A treatment will result in the reduction, amelioration, or elimination of one or more symptoms of the disorder.

"Preventing" as used herein is meant as stopping or delaying the onset of a disorder, for example a respiratory disorder, such as a disease or other condition of the respiratory system. A preventative measure will result in the stoppage or delay of one or more symptoms of the disorder, or a lessening of symptoms if such do arise. It should be understood that the term "treating or preventing" does not exclude the possibility of obtaining both treatment and prevention (e.g., at the same time or at different times) of a disorder in any given subject. In the same way treatment of "asthma or fibrosis" does not exclude the possibility of obtaining treatment (e.g., simultaneous or not simultaneous) of both disorders.

Compositions Comprising Boysenberry and the Associated Bioactivity of these Compositions The inventors have found that consumption of a Boysenberry composition reduces allergen-induced lung remodelling in a chronic model of asthma. For these experiments, the effect of Boysenberry consumption was tested on lung fibrosis, lung macrophage phenotype, and MMP-9 expression in a chronic model of allergic airway inflammation. The results demonstrated that oral Boysenberry treatment supports the development of lung macrophages that express a mixed antifibrotic, AAM (alternatively activated macrophages) phenotype with the capacity to ameliorate fibrosis and promote balanced lung repair (74; incorporated herein by reference in its entirety). Further to this, the inventors have found that combined administration of Boysenberry and apple compositions, and combined administration of Boysenberry, apple and blackcurrant compositions, can be used to reduce numbers of immune cells associated with airways inflammation. This can include one or more of eosinophils, neutrophils, monocytes, and antigen presenting cells. Surprisingly, and advantageously, the combined Boysenberry and apple compositions are effective at low dosages.

Boysenberries are known to be high in Vitamin C and fibre and contain high levels of anthocyanins (120-160 mg/100 g) that give Boysenberries their deep, dark colour. The ORAC (oxygen radical absorption capacity, i.e., antioxidant level) for Boysenberries is 42 μmoles/TE/g almost double that of blueberries, a well known antioxidant food. Boysenberries contain notable amounts of ellagic acid, a phenolic compound. The ellagic acid level in Boysenberries is 5.98 mg/g of dry weight. Boysenberries also have a high ratio of free ellagic acid to total ellagitannins. The inventors have tested concentrates to confirm biological activity.

As described in Example 2, these solutions included: Boysenberry 10 (Boysenberry juice solution), 6.7%, Boysenberry 1 (Boysenberry juice solution), 0.67%, apple 10 (apple juice solution), 18.7%, apple 1 (apple juice solution), Boysenberry and apple 10 (BerriQi™ Boysenberry with apple; combined juice solution), 6.7%/18.7%, Boysenberry and apple 1 (BerriQi™ Boysenberry with apple; combined juice solution), 0.67%/1.87%. Additional oral compositions are described in Examples 3-5, including BerriQi™ Boysenberry with apple composition at 100%, 50% or 25% concentration, and BerriQi™ Boysenberry with apple and blackcurrant composition at 100% concentration. The 100% BerriQi™ Boysenberry with apple composition includes Boysenberry juice concentrate at 27% and apple juice concentrate at 73%. The 100% BerriQi™ Boysenberry with apple and blackcurrant composition includes Boysenberry juice concentrate at 13.5%, apple juice concentrate at 7%, and blackcurrant juice concentrate at 13.5%. Further details are provided in the Examples section, below.

From the inventors' results it is evident that Boysenberries and apples and Boysenberry, apple and blackcurrant may be used in compositions for treating or preventing inflammation of the respiratory tract, treating or preventing asthma, treating or preventing chronic obstructive pulmonary disease, treating or preventing allergic airways inflammation, treating or preventing fibrosis of the respiratory tract, or treating or preventing airway remodelling. In particular, as to airway remodelling, the compositions of the invention may be used to treat or prevent one or more of: the thickening of the walls of the alveoli, increasing of collagen fibres in the airway, spreading of collagen fibres into the airway tissues, and collapsing or closing of the airspace(s). In addition, the compositions of the invention may be used to reduce tissue inflammation and collagen deposition that leads to airway remodelling.

In addition, from the results shown herein, it will be understood that Boysenberry and apple compositions and Boysenberry, apple and blackcurrant compositions may be used to restore, improve, or maintain the health of the respiratory system, for example, in one or more activities of: decreasing collagen deposition, abrogating aberrant collagen deposition, decreasing cellular infiltration into the airways, decreasing airway damage due to cellular infiltration, reducing cells in the lung fluid, e.g., inflammatory cells, reducing mucus production, reducing mucus-positive cells, decreasing hydroxyproline levels, increasing matrix metallopeptidase expression levels, e.g., protein levels, increasing MMP-9 expression levels, e.g., protein levels, increasing TGFβ expression levels, e.g., protein levels, decreasing the ratio level of TIMP-1/MMP-9, e.g., protein ratio levels, decreasing the activation or number of inflammatory cells, increasing the number or activity of alternatively activated macrophages, increasing the number or activity of arginase+ macrophages, increasing the number or activity of CD68+/CD206+/arginase+macrophages, or decreasing iNOS expression levels, e.g., protein levels. Further uses for these compositions are described in detail herein.

Methods of Producing Compositions Comprising Boysenberry and Apple and Compositions Comprising Boysenberry, Apple and Blackcurrant The present invention relates generally to a composition prepared from Boysenberry and apple, as well as a composition prepared from Boysenberry, apple and blackcurrant. While specific combinations of Boysenberry and apple, and Boysenberry, apple and blackcurrant, are described herein, it is understood that the composition of the invention can include any combination of Boysenberry, apple, and blackcurrant therein. In one particular aspect, the composition is prepared from *Rubus ursinus* var *loganobaccus* cv Boysenberry. In other aspects, one or more genetic derivatives from this Boysenberry plant may be used. For example, it may be desirable to use F1 or F2 progeny from a genetic cross that includes the parent stock of the Boysenberry plant. Alternatively, any sports or other cultivars obtained from the parent may be used. It may be desirable to source the Boysenberries from New Zealand, in particular, or alternatively, from Chile.

The composition is preferably prepared as a Boysenberry concentrate, for example, a Boysenberry puree, a Boysenberry pomace, Boysenberry paste, Boysenberry powder, Boysenberry juice concentrate. The Boysenberry and apple composition may comprise an apple concentrate, for example, an apple puree, an apple pomace, an apple paste, an apple powder, or apple juice concentrate. If an apple juice concentrate is used, this may have originated from cloudy apple juice or clear apple juice. The Boysenberry, apple and blackcurrant composition may comprise a blackcurrant concentrate, for example, a blackcurrant puree, a blackcurrant pomace, a blackcurrant paste, a blackcurrant powder, a blackcurrant juice concentrate. It will be understood that Boysenberry, apple, or blackcurrant pomaces, in particular, may be used, which include the solid remains of the fruit after pressing for juice. The pomace may encompass one or more of the skins, pulp, seeds, and stems of the fruit. In addition, it is possible to include one or more of a Boysenberry juice, an apple juice, and a blackcurrant juice in the compositions disclosed herein.

Accordingly, the composition may be prepared in liquid or powdered form, for example, a lyophilised powder, or in any other suitable dosage form. The composition may be formulated as a tonic, extract, elixir, linctus, concentrate, syrup, solution, suspension, emulsion, draught, puree, paste, or as drops. In other aspects, the composition may be formulated as a gel or jelly, or a capsule, for example, with liquid or semi-liquid contents. The composition may be provided in sachet form, for example, a powder sachet, or a gel or jelly sachet. Included also are formulations comprising thin strips, or comprising solids in a capsule to mix with food or drink. Other formulas are also possible, as described herein below.

In certain aspects, it may be desirable to formulate the Boysenberry and apple composition (e.g., Boysenberry and apple juice concentrate or puree) or the Boysenberry, apple and blackcurrant composition (e.g., Boysenberry, apple and blackcurrant juice concentrate or puree) into a powder. As specific exemplifications, apple powder may comprise apple pomace powder or apple pectin powder. Commercial Boysenberry, apple, and blackcurrant powders are known and available, as noted herein. The powder may be formulated as tablets (including rapid dissolve tablets) or capsules (including extended release capsules). The tablets may be scored tablets, chewable tablets, effervescent tablets, orally disintegrating tablets, or tablets for forming a suspension. The capsules may be gel capsules, for example, and may include powdered contents. This includes gel capsules made by single piece gel encapsulation and two piece gel encapsulation. Non-gelatine capsules are also included, as well as caplets. The powder may be provided in free flowing form or as a solid cake. The composition may be provided as a powder for forming a suspension, powder for forming a solution, bulk oral granules, or bulk oral powder.

The compositions of the invention may be prepared from Boysenberry, apple, or blackcurrant juice concentrate or puree obtained from one or more commercial sources. For example, commercial sources of New Zealand Boysenberry products include Boysenberries New Zealand Ltd, Nelson, and Tasman Bay Berries, Nelson. Commercially available products include individually quick frozen berries, Boysenberry puree, block frozen berries, Boysenberry juice concentrate, and Boysenberry powder. Commercial sources of New Zealand apple and blackcurrant products include those from EnzaFoods New Zealand Ltd, Hastings, New Zealand, as well as Juice Products New Zealand, Timaru, New Zealand, NZ Blackcurrant Co-operative Ltd, Nelson, New Zealand, Fruit Solutions, FSL Foods, Nelson, New Zealand, and Reso, Auckland, New Zealand, and encompass cloudy apple juice concentrate, clear apple juice concentrate, apple pomace, apple puree, blackcurrant juice concentrate, and blackcurrant puree. In addition, apple and blackcurrant powders may be obtained commercially from TreeTop®, FutureCeuticals, Nutradry, Sujon, Viberi™, Zeaberry™, Waitaki Biosciences, amongst other suppliers. Specific suppliers of apple and blackcurrant juice concentrate include Infruit Ltd, Auckland, New Zealand, and RD2 International Ltd, Auckland, New Zealand, while manufacturers include Profruit (2006) Ltd, Hastings, 4175, New Zealand, as noted herein.

The pH of the juice concentrate or puree, for example, the combined Boysenberry and apple juice concentrate, and combined Boysenberry, apple and blackcurrant juice concentrate, may range from 3.2 to 3.8; or 3.0 to 4.0; or 3.1 to 3.9; or may be about 3.1, about 3.2, about 3.3, about 3.4, about 3.5, about 3.6, about 3.7, about 3.8, about 3.9, or about 4.0. For the apple juice concentrate that is used to make the combined concentrate, the pH may range from 2.8 to 4.4; 2.9 to 4.3; 3.0 to 4.2; or 3.1 to 4.0; or may be about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, or about 4.5. For the blackcurrant juice concentrate that is used to make the combined concentrate, the pH may range from 1.0 to 5.0; 2.0 to 4.0; 1.5 to 3.5; 2.1 to 3.4; or 2.3 to 3.3; or may be about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0.

For the Boysenberry juice concentrate, the acidity (% w/w citric acid anhydrous) may be about 1 to about 20, about 1.5 to about 15, about 2 to about 12, about 5 to about 10, about 6 to about 9, about 10, about 9, about 8.5, about 8.3, about 8.2, about 8.17, about 8.1, about 8, about 7, about 6, or about 5. For the apple juice concentrate, the acidity (% w/w malic) may be about 0.5 to about 4.5, about 0.8 to about 4.2, about 1.0 to about 4.0, about 1.2 to about 3.5, or about 0.5, about 0.7, about 0.9, about 1, about 1.2, about 1.5, about 1.7, about 1.9, about 2, about 2.2, about 2.5, about 2.7, about 2.9, about 3, about 3.2, about 3.5, about 3.7, about 3.9, about 4, about 4.2, or about 4.5. For the blackcurrant juice concentrate, the acidity (citric acid g/100 g) may be about 5 to about 20, about 8 to about 18, about 7 to about 17, or about 5, about 6, about 7, about 8, about 9, about 10, about 11, about 12, about 13, about 14, about 15, about 16, about 17, about 18, about 19, about 20, about 21, about 22, about 23, about 24, or about 25.

In some circumstances, it may be desirable to adjust the pH of the puree or that of the final composition to approximate physiological levels. In particular, it may be useful to obtain a pH range from 6.0 to 8.0; or 6.5 to 7.5; or 6.8 to 7.2; or a pH of about 6.5, about 6.7, about 6.8, about 6.9, about 7.0, about 7.1, about 7.2, about 7.3, about 7.4, or about 7.5.

In certain aspects, the compositions of the invention may be prepared by "soft pulping" technology referred to in New Zealand Patent No. 235972 (incorporated by reference herein), which can be adapted to produce a "soft" Boysenberry, apple, or blackcurrant puree. It may be useful to prepare the puree to have seeds removed. It may also be useful to prepare the puree with a sieve size of about 1 mm or less.

A juice concentrate may be prepared as a natural sugar solution that is extracted or pressed and filtered from the skin and pulp, and may include the seeds. The solution may be depectinized, filtered, and evaporated under vacuum to a specified Brix level. For example, the juice concentrate may be folded about two to about seven times the original Brix value. In particular, the concentrate may be folded about two times, about three times, about four times, about five times, about six times, or about seven times the original Brix value.

In certain aspects, the Boysenberry juice concentrate may be manufactured from sound, ripe graded boysenberries (e.g., *Rubus ursinus* var *loganobaccus* cv Boysenberry). In particular aspects, the Boysenberry juice concentrate may have a final sugar level ranging from 55° to 75° Brix; or 59° to 69° Brix; or 61° to 66° Brix; or about 60°, about 61°, about 62°, about 63°, about 64°, about 65°, about 65.4°, about 65.5°, about 65.6°, about 66°, about 67°, about 68°, about 69°, about 70°, or about 71° Brix. In various aspects, the combined Boysenberry and apple juice concentrate, and the combined Boysenberry, apple and blackcurrant juice concentrate may have the Brix values as noted directly above. Similarly, the apple juice concentrate and blackcurrant juice concentrate that is used to make the combined concentrate may have the Brix values as noted above, when uncorrected for acidity.

The juice concentrate may be produced by milling, mashing and pressing into single strength juice which is centrifuged, pasteurized, depectinised, filtered and then concentrated by evaporation with aroma returned in the standardisation process. The standardised concentrate may then be packed through the hygienic filler head into the required pack style without further heat treatment. The concentrate can be checked for compliance with the definition of a pure fruit juice, for example, as defined by the FSANZ-Food Standards Australia New Zealand.

It is expected that the Boysenberry juice concentrate will be rich in colouration. For example, the Boysenberry juice concentrate may have a colour ratio (absorbance 520 nm/absorbance 430 nm) of about 1.5 to about 3.0, about 1.8 to about 2.8, about 1.9 to about 2.2, or about 1.9, about 2, about 2.01, about 2.05, about 2.1, or about 2.2. In addition, the juice concentrate may have a colour intensity (utilising Chroma meter) of about 15 to about 30, about 20 to about 28, about 21 to about 25, about 22 to about 24, or about 22, about 23, about 23.2, about 23.5, about 23.7, about 24, or about 25. The juice concentrate is also expected to be relatively clear in appearance, for example, with clarity levels of about 0.01 to about 0.1, about 0.02 to about 0.08, about 0.03 to about 0.06, about 0.04 to about 0.05, or about 0.03, about 0.04, about 0.045, about 0.047, about 0.048, about 0.05, or about 0.06.

The blackcurrant concentrate that is used to make the combined concentrate will also have deep colouration. For example, the blackcurrant concentrate may have a colour ratio (absorbance 520 nm/absorbance 430 nm at pH 3) of about 1.5 to about 4.0, about 1.8 to about 3.8, or about 2.0 to about 3.0; or a colour ratio of about 1.8, or about 1.9, or about 2.0, or about 2.1, or about 2.2, or about 2.3, or about 2.4, or about 2.5, or about 2.6, or about 2.7, or about 2.9, or about 3.0, or about 3.2, or about 3.3, or about 3.4, or about 3.5.

In contrast, the apple juice concentrate that is used to make the combined concentrate may be relatively colourless, for example, less than 0.35 abs at 420 nm 12 Bx, or at least less than 0.45 abs at 420 nm 12 Bx. For apple juice concentrate, this can also be express as a general range of about 0.15 to about 0.45 abs, about 0.10 to about 50 abs, or about 0.19 to about 45 at 440 nm and 11.5° Brix. The apple juice concentrate may be used as a clear concentrate, e.g., free from haze. The specific gravity of the various juice concentrates may be about 1.2 to about 1.4, about 1.29 to about 1.39, or about 1.32 to about 1.36, or about 1.2, about 1.3, about 1.31, about 1.32, about 1.33, about 1.35, about 1.36, about 1.37, about 1.38, about 1.39, or about 1.4 at 20° C. The various measurement methodologies, e.g., colour ratios, clarity, etc, are known in the art, and may be found, for example, in the AIJN code of practice in the International Fruit Juice Federation Handbook of Analysis, 1996, International Fruchtsaft-Union, Zug, Switzerland.

In initial preparatory stages, the Boysenberry, apple, or blackcurrant may undergo a pre-treatment process which may include the well known steps of ripening, inspecting, grading, and/or sorting of the berries/fruit. With regard to ripening, it is preferable to use ripe or mature Boysenberry, apple, or blackcurrant when producing the compositions of the invention; however, rotted or decaying material is preferably avoided. Ripeness can be assessed using widely known and used methods in the art. Ripeness can be measured prior to picking or processing the Boysenberry, apple, or blackcurrant. In particular, ripeness may be measured using the Brix system, as noted herein. Boysenberry, apple, or blackcurrant that is overly mature or fermenting may not produce an ideal composition. Boysenberry, apple, or blackcurrant with a Brix level below the ideal may be artificially ripened before use.

As part of the processing, the Boysenberry, apple, or blackcurrant may be sterilised. The fruit may be passed through an assembly having one or more roller brushes for removing any adhering foreign matter. Conventional washing techniques may then be employed. For example, it is possible to use a series of spray nozzles to wash the Boysenberry, apple, or blackcurrant. Wash additives aiding cleansing or reducing the bacteria count on the Boysenberry, apple, or blackcurrant may be employed according to local regulations and requirements. For example, the Boysenberry, apple, or blackcurrant may be washed by a chlorine wash and/or an ozone impregnated water wash followed by a fresh water rinse.

The sterilized Boysenberry, apple, or blackcurrant may then be conveyed into a hopper. This can be tapered to form a funnel to direct the berries or fruit to a pressing assembly. The pressing assembly may be adapted to perform a pulping or comminution process. Such process can be relatively mild and gentle ("soft pulping") compared to conventional fruit pulping techniques. With soft pulping, no significant disintegration or lysis of fruit cells or components. Preferably, only a minor proportion (generally less than 5-10%) of seeds is fragmented by this process.

In one embodiment, the pressing assembly performs the soft pulping of the Boysenberry, apple, or blackcurrant by pressing between a twin converging belt press. The press belts may be multiple loops rotated about a series of pulleys. The distance separating the press belts may decrease in the direction of travel of the Boysenberry, apple, or blackcurrant. In this way, increased force may be exerted upon the Boysenberry, apple, or blackcurrant as it travels along the length of the pressing assembly. This can produce pulping without significant damage to the seeds. This in turn prevents seeds from contaminating the pulp.

The pulp generated from the pressing assembly may be directed to a screening process, in order to separate the seeds from the pulp. In particular, the pulp may be separated from the seed using a soft mechanical screening technique. For example, a pulp finisher may be used. This includes a rotating flexible impeller which is rotated within a cone shaped screen having apertures of a predetermined size. In particular aspects, the size of the apertures is selected to permit the pulp and juice to pass through the screen while retaining a substantial portion, if not all, of the seeds within the interior cavity defined by the screen.

In certain aspects, it may be preferable to use a paste rather than a puree from the Boysenberry, apple, or blackcurrant. A paste may be made as a concentrate. For example, the fruit may be heated for several hours, strained, and reduced to a thick, concentrated form. The fruit may be heated after removing the skins, or after the pulping or pureeing process. The fruit can be heated gradually, and then kept heated at a moderate temperature, with mixing. Upon thickening, the paste can be spread on a flat sheet, or transferred to a packaging, for example, a bag, tube, jar, bottle, or other container. The paste may be transferred aseptically, such that it is suitable for human consumption. It may be desired to prepare the paste from mature berries/fruits. The paste may be prepared from pulped fruit. The paste may be a smooth preparation.

The pulp (e.g., in paste or puree form) or juice concentrate may be processed by a freezing step. This may be followed by or used in conjunction with a drying step. In an alternative embodiment, the pulp is dried and processed to a powder without an intervening freezing step. For example, methods involving drum drying may be used. In the drum-drying process, a puree or paste may be dried at relatively low temperatures over rotating, high-capacity drums that produce sheets of drum-dried product. In certain aspects, an additive may be used to accelerate or otherwise assist the drying process. For example, pea starch or other drying aids may be utilised. The dried product may then be milled to a finished flake or powder form. Advantageously, drum drying techniques may be used to produce a dried composition that retains its key components, e.g., phenolic compounds, and can be easily reconstituted using liquid. For example, drum dried products may be made to be cold water soluble. As further alternatives, belt drying or convection drying may be used. Such drying methods are widely known and used in the field.

If freezing is used, it is preferable to freeze the pulp or juice concentrate as soon as possible after it is produced to maintain freshness. However, freezing may be carried out within 24 or 48 hours, as needed. Freezing methodologies are well known and need not be described in significant detail herein. Blast freezing is particularly preferred for use with the invention. The pulp or juice concentrate may be frozen in standard sized pales, which are used to collect the fresh pulp/concentrate after processing. The pulp or juice concentrate can be stored frozen (e.g., at −18° C.) until it is required.

The frozen pulp or juice concentrate may be freeze dried, i.e., lyophilised. Freeze drying techniques are widely known and commonly used. The freeze drying cycle may be about 48 hours; or ranging from 40 to 56 hours; or 12 to 36 hours; or 36 to 60 hours; or about 40 hours, about 42 hours, about 44 hours, about 46 hours, about 48 hours, about 50 hours, about 52 hours, or about 54 hours. A longer freeze drying cycle, e.g., at least 48 hours ("gentle freeze drying"), may be used to retain maximal activity. In particular aspects, the process may be carried out to such that water formation is avoided, and the moisture content is minimised during processing.

It may be desirable to use a particular lyophilisation process for obtaining the dried product. For example, a lyophilisation drying program may be used as part of an automated drying system. The lyophilisation process may include multiple drying steps, e.g., with step-wise increases and reductions in temperature. Preferably, a primary drying setting is used for sublimation, followed by one or more secondary drying settings that are used to remove residual moisture. In particular aspects, the top temperature of the lyophilisation process does not exceed 70° C. In other aspects, the temperature of the lyophilisation process ranges between −10° C. to 70° C. In one other aspect, up to 48 hours of lyophilisation is utilised.

The resulting dried product may then be milled into a powder which can then be utilised as appropriate. Milling methods are well known and widely used in the art. Standard mesh sizes may be used to produce the powder, for example, US 20, US 23, US 30, US 35, US 40, US 45, or US 50 mesh sizes may be used. The sieve size for the powder may range from 1.0 to 0.3 mm; or 0.84 to 0.4 mm; or 0.71 to 0.5 mm; or may be about 1.0 mm, about 0.84 mm, about 0.71 mm, about 0.59 mm, about 0.5 mm, about 0.47 mm, about 0.465 mm, about 0.437 mm, about 0.4 mm, about 0.355 mm, or about 0.3 mm.

To ensure minimal degradation of ingredients, the preparation process may be performed at a temperature of less than 40° C. In various embodiments, the process is performed at a temperature ranging from −4° C. to 40° C.; or from −1° C. to 10° C.; or from 1° C. to 6° C.; or at about 0° C., about 1° C., about 2° C., about 3° C., about 4° C., about 5° C., or about 6° C. These temperatures may be kept during the entire preparation process, including the storage of the whole fruit, prior to it being broken open, and during the pulping/pureeing process. For optimal results, these temperatures are kept at least from the point that the fruit has been broken open. Use of such temperatures avoids oxidation of the fruit and the use of reducing agents. In certain circumstances, it may be possible to obtain organic certification.

The processing method is preferably performed so as to prevent or at least minimise any damage or effects on the active material in the fruit. To ensure optimal production methods, the resulting compositions can be monitored for activity, for example, for anthocyanin levels, polyphenol levels, and/or antioxidant activity.

Assays for polyphenols are well known in the art and are also described below. In particular, it is possible to measure gallic acid equivalents (GAE) to determine total polyphenol content. For example, the Folin-Ciocalteu method (employing the Folin-Ciocalteu reagent, also called Folin's phenol reagent or Folin-Denis reagent) may be used for colorimetric in vitro assays of phenolic compounds (75). It is expected that the total polyphenol content of a Boysenberry juice concentrate will be relatively high, for example, about 500 to about 5000 mg GAE/100 g FW, about 1000 to about 3000 mg GAE/100 g FW, about 1500 to about 2500 mg GAE/100 g FW, about 3000, about 2500, about 2000, about 1500, or about 1000 mg GAE/100 g FW. It is noted that FW indicates the fresh weight of the juice concentrate.

Anthocyanins may be quantified by HPLC. This can be used give breakdown of individual compounds and expressed as cyanidin 3-glucoside equivalents (76). For example, HPLC eluted components may be monitored at 530 nm for anthocyanins. A standard curve may be prepared using a cyanidin-3-glucoside standard (for example, from Extrasynthese) and total anthocyanins may be calculated on this basis. Other phenolics may also be analysed by HPLC, for example at 250-700 nm. A range of standards may be run, including gallic acid, ellagic acid, quercetin, rutin and catchin. Absorbance spectra and retention time of the standards may be compared with unknowns in the HPLC traces. This analysis can include measurements for ellagic acid. As non-limiting examples, the total anthocyanin content of a Boysenberry juice concentrate (expressed as cyanidin 3-glucoside equivalents) may be about 1000 to about 10,000 mg/100 g FW, about 2000 to about 8000 mg/100 g FW, about 4000 to about 7000 mg/100 g FW, about 5500 to about 6500 mg/100 g FW, or about 8000, about 7000, about 6500, about 6800, about 6000, about 5000, about 4000, or about 3000 mg/100 g FW.

For the combined Boysenberry and apple compositions, it is expected that the total anthocyanins may account for about 40-50% of the total polyphenol content that is present in these compositions, or at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, or at least 55% of the total polyphenol content that is present in these compositions. For the combined and Boysenberry, apple and blackcurrant compositions, it is expected that the total anthocyanins may account for about 70-80% of the total polyphenol content that is present in these compositions, or at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, or at least 80%, of the total polyphenol content that is present in these compositions.

In addition, for the combined Boysenberry and apple compositions and the Boysenberry, apple and blackcurrant compositions, it is expected that the total polyphenols (including anthocyanins) may account for about 80-90% of the total polyphenol content that is present in these compositions, or at least 70%, at least 71%, at least 72%, at least 73%, at least at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, or at least 95% of the total polyphenol content that is present in these compositions.

Further to this, for the combined Boysenberry and apple compositions and the Boysenberry, apple and blackcurrant compositions, it is expected that the hydrolysable tannins will account for about 25% to about 35% of the total polyphenols in the composition. For the Boysenberry, apple and blackcurrant compositions, it is expected that the hydrolysable tannins will account for about 8% to about 12% of the total polyphenols in the composition. An exemplary method for measuring hydrolysable tannins is LC-MS (liquid chromatography-mass spectrometry) analysis, as described in detail herein.

Antioxidant capacity may be measured by ORAC and/or DPPH assays. The oxygen radical absorbance capacity assay is one of the most widely utilised assays to test the antioxidant potential of foods. The ORAC assay measures antioxidant inhibition of peroxyl radical-induced oxidation (77, 78, 84). Trolox, a water-soluble analogue of vitamin E, may be used as a control standard. In an additional assay, DPPH (2,2-diphenyl-1-picrylhydrazyl) may be used to show the kinetic behaviour of polyphenols as free radical scavengers. The higher the antioxidant activity, the larger the decrease of DPPH concentration. A methanolic solution of the DPPH radical changes from purple to colourless when quenched by antioxidants. The decrease in DPPH is measured at 515 nm against standard curves, e.g., Trolox and DPPH (79, 80).

As particular exemplifications, the antioxidant capacity for the Boysenberry juice concentrate may be about 10,000 to about 100,000 ORAC value (μmol Trolox/100 g FW), about 20,000 to about 80,000 ORAC value, about 30,000 to about 70,000 ORAC value, about 40,000 to about 50,000 ORAC value, or about 80,000, about 70,000, about 60,000, about 50,000, about 40,000, about 30,000, or about 20,000 ORAC value. As further exemplifications, the antioxidant capacity for the Boysenberry juice concentrate may be measured with the DPPH assay (at 100% MeOH) as about 1000 to about 6000 μmol TEAC/100 g FW, about 2000 to about 5000 μmol TEAC/100 g FW, about 2500 to about 2900 μmol TEAC/100 g FW, or about 5000, about 4000, about 3000, about 2800, about 2500, about 2000, or about 1000 μmol TEAC/100 g FW.

Alternatively or additionally, the compositions can be tested for other components, e.g., sugars, folate, and Vitamin C. The corresponding assays are widely known. For example, folate levels of the Boysenberry juice concentrate may be measured using standard methodologies (see, e.g., 83), and may be about 20 μg/100 g FW, about 30 μg/100 g FW, about 40 μg/100 g FW, or about 50 μg/100 g FW, about 60 μg/100 g FW, about 70 μg/100 g FW, or about 80 μg/100 g FW, or about 10 to about 100 μg/100 g FW, about 20 to about 80 μg/100 g FW, about 30 to about 70 μg/100 g FW, about 20 to about 50 μg/100 g FW, or about 50 to about 70 μg/100 g FW.

It will be understood that other known assays may also be used to analyse the disclosed compositions (see, e.g., 85), and the invention is not limited to one particular assay for bioactive compounds, including phenolics, anthocyanins, antioxidants, vitamins, carbohydrates, etc. It will be understood also that the levels identified herein for juice concentrates can be readily extrapolated to powdered forms, as well as puree and paste forms.

In some circumstances, it may be possible to use genetic derivative of the plant to obtain the compositions of the invention. It is expected that a composition obtained from such derivative would share one or more of the characteristics of the compositions obtained from the original stock. Exemplary features include: polyphenol levels and polyphenol profiles, including anthocyanidin levels and profiles, vitamin levels, and reduction of OVA-induced inflammation, as noted above and disclosed in detail herein. Regarding the fruit itself, it is expected that the fruit obtained from a genetic derivative would share a similar compositional makeup as the parent fruit.

Compositions Comprising Boysenberry and Apple and Compositions Comprising Boysenberry, Apple and Blackcurrant The inventors have found that Boysenberry compositions include beneficial ingredients that are useful for maintaining the health of the respiratory system, as well as treating and preventing respiratory problems. The inventors have shown that a Boysenberry concentrate is particularly efficacious for reducing airway inflammation and fibrosis. Also efficacious are a combined Boysenberry and apple concentrate, and a combined Boysenberry, apple and blackcurrant concentrate, as described herein. As such, the Boysenberry compositions, including combined Boysenberry and apple compositions, and combined Boysenberry, apple and blackcurrant compositions, disclosed herein can be used to support or improve overall respiratory health and/or to treat or prevent various disorders or other conditions of the respiratory tract, including inflammation, asthma, chronic obstructive pulmonary disease, airway fibrosis, and airway remodelling. In this way, the disclosed compositions are understood to be anti-inflammatory compositions, and also anti-asthmatic compositions, as well as being compositions that are active against chronic obstructive pulmonary disease, reactive airway disease, airway fibrosis, and airway remodelling.

As described herein, a Boysenberry composition may comprise a juice concentrate or a powder concentrate prepared from Boysenberries. The composition may further comprise a juice concentrate or a powder concentrate prepared from apples, or may further comprise a juice concentrate or a powder concentrate prepared from blackcurrants. As various alternatives, the composition may consist of, or may consist essentially of: a juice concentrate or a powder concentrate prepared from Boysenberries and a juice concentrate or a powder concentrate prepared from apples, or a juice concentrate or a powder concentrate prepared from Boysenberries and a juice concentrate or a powder concentrate prepared from blackcurrants.

Generally speaking, the Boysenberry and apple concentrate may include various ratios of Boysenberry concentrate to apple concentrate. As exemplifications, the percentages of Boysenberry concentrate to apple concentrate (having a combined percentage of 100% v/v) may include about 17% Boysenberry concentrate to about 83% apple concentrate, about 18% Boysenberry concentrate to about 82% apple concentrate, about 19% Boysenberry concentrate to about 81% apple concentrate, about 20% Boysenberry concentrate to about 80% apple concentrate, about 21% Boysenberry concentrate to about 79% apple concentrate, about 22% Boysenberry concentrate to about 78% apple concentrate, about 23% Boysenberry concentrate to about 77% apple concentrate, about 24% Boysenberry concentrate to about 76% apple concentrate, about 25% Boysenberry concentrate to about 75% apple concentrate, about 26% Boysenberry concentrate to about 74% apple concentrate, about 27% Boysenberry concentrate to about 73% apple concentrate, about 28% Boysenberry concentrate to about 72% apple concentrate, about 29% Boysenberry concentrate to about 71% apple concentrate, about 30% Boysenberry concentrate to about 70% apple concentrate, about 31% Boysenberry concentrate to about 69% apple concentrate, about 32% Boysenberry concentrate to about 68% apple concentrate, about 33% Boysenberry concentrate to about 67% apple concentrate, or about 34% Boysenberry concentrate to about 66% apple concentrate, these percentages being representative of v/v values.

In the same way, the percentages of Boysenberry and blackcurrant concentrate to apple concentrate (having a combined percentage of 100% v/v) may include about 17% Boysenberry and blackcurrant concentrate to about 83% apple concentrate, about 18% Boysenberry and blackcurrant concentrate to about 82% apple concentrate, about 19% Boysenberry and blackcurrant concentrate to about 81% apple concentrate, about 20% Boysenberry and blackcurrant concentrate to about 80% apple concentrate, about 21% Boysenberry and blackcurrant concentrate to about 79% apple concentrate, about 22% Boysenberry and blackcurrant concentrate to about 78% apple concentrate, about 23% Boysenberry and blackcurrant concentrate to about 77% apple concentrate, about 24% Boysenberry and blackcurrant concentrate to about 76% apple concentrate, about 25% Boysenberry and blackcurrant concentrate to about 75% apple concentrate, about 26% Boysenberry and blackcurrant concentrate to about 74% apple concentrate, about 27% Boysenberry and blackcurrant concentrate to about 73% apple concentrate, about 28% Boysenberry and blackcurrant concentrate to about 72% apple concentrate, about 29% Boysenberry and blackcurrant concentrate to about 71% apple concentrate, about 30% Boysenberry and blackcurrant concentrate to about 70% apple concentrate, about 31% Boysenberry and blackcurrant concentrate to about 69% apple concentrate, about 32% Boysenberry and blackcurrant concentrate to about 68% apple concentrate, about 33% Boysenberry and blackcurrant concentrate to about 67% apple concentrate, or about 34% Boysenberry and blackcurrant concentrate to about 66% apple concentrate, these percentages being representative of v/v values.

As non-limiting examples, the percentage of blackcurrant concentrate in the combined Boysenberry, apple and blackcurrant concentrate may be about 5% to about 20%, or about 8% to about 18%, or about 10% to about 15%, or a percentage of about 5%, about 8%, about 10%, about 13.5%, about 15%, about 18%, or about 20%, these percentages being representative of v/v values. In particular aspects, the percentage of the blackcurrant concentrate is the same or substantially the same as the percentage of Boysenberry concentrate in the combined Boysenberry, apple and blackcurrant concentrate.

The Boysenberry and apple concentrate and the Boysenberry, apple and blackcurrant concentrate (having a combined percentage of 100% w/v) may include less than 1% of a preservative, for example, about 0.005% to about 0.5%, or about 0.05% to about 0.15%, or may include about 0.04%, about 0.06%, about 0.08%, about 0.1%, about 0.12%, about 0.14%, about 0.16%, about 0.18%, or about 0.2% of a preservative, these percentages being representative of w/v values. Useful preservatives include but are not limited to sorbic acid, sodium sorbate, potassium sorbate, citric acid, ascorbic acid, malic acid, tartaric acid, propionic acid, and benzoic acid, for example, in the form of its sodium salt, e.g., sodium benzoate.

The composition may be formulated as a liquid, for example, a juice concentrate, syrup, suspension, or tonic for oral administration, or as a solution for enteral administration. Alternatively, the composition may be formulated as a powder to be encapsulated, tableted, or added to or incorporated in other products. Particularly encompassed are delayed release formulas, extended release formulas, as well as formulas for rapid disintegration. Capsules, for example gel capsules, are specifically encompassed, as well as sachets and chewable tablets. Additionally included are combination formulas, which include the powder of the invention mixed with other beneficial agents, e.g., one or more respiratory aids. In various aspects, the composition may be prepared as a nutraceutical composition, a pharmaceutical composition, a functional food or beverage, a natural ingredient (e.g., a natural additive), or a natural supplement (e.g., a dietary supplement).

It is expected that the Boysenberry composition, including the combined Boysenberry and apple composition and the combined Boysenberry, apple and blackcurrant composition, will be prepared to include high levels of anthocyanins. For example, the composition may include about 2 to about 50,000 mg/ml total anthocyanins or total Boysenberry and blackcurrant anthocyanins, or about 20 to about 40,000 mg/ml, about 25 to about 35,000 mg/ml, about 30 to about 30,000 mg/ml, about 40 to about 25,000 mg/ml, about 50 to about 20,000 mg/ml, about 60 to about 15,000 mg/ml, about 70 to about 10,000 mg/ml, about 80 to about 8000 mg/ml, about 90 to about 6000 mg/ml, about 100 to about 5000 mg/ml, about 10 to about 1000 mg/ml, about 20 to about 800 mg/ml, about 30 to about 600 mg/ml, about 50 to about 200 mg/ml, or about 50,000, about 40,000, about 35,000, about 25,000, about 20,000, about 15,000, about 12,000, about 10,000, about 8000, about 7500, about 5000, about 2500, about 2000, about 1000, about 1500, about 1200, about 1000, about 750, about 500, about 250 mg/ml, about 200 mg/ml, about 150 mg/ml, about 100 mg/ml, about 75 mg/ml, about 50 mg/ml, about 25 mg/ml, about 20 mg/ml, or about 10 mg/ml total anthocyanins, or total Boysenberry and blackcurrant anthocyanins, or a dry weight equivalent thereof.

In specific aspects, the Boysenberry composition, including the combined Boysenberry and apple composition and the combined Boysenberry, apple and blackcurrant composition, may be administered at a dosage unit of about 1 mg to about 20,000 mg total anthocyanins or total Boysenberry and blackcurrant anthocyanins, or about 1 mg to about 2000 mg total anthocyanins or total Boysenberry and blackcurrant anthocyanins, or about 5 mg to about 5000 mg, about 10 mg to about 3000 mg, about 10 to about 1000, about 15 mg to about 1500 mg, about 20 mg to about 1000 mg, about 25 mg to about 850 mg, about 30 mg to about 600 mg, about 35 mg to about 550 mg, about 50 to about 500 mg, about 5 to about 500, about 10 mg to about 200 mg, about 1 to about 400 mg, about 1 to about 200 mg, about 40 mg to about 400 mg, about 40 to about 200 mg, about 20 mg to about 80 mg, about 30 mg to about 60 mg, about 45 mg to about 55 mg, or about 20,000 mg, about 15,000 mg, about 12,000 mg, about 10,000 mg, about 7500 mg, about 5000 mg, about 4000 mg, about 3000 mg, about 2000 mg, about 1500 mg, about 1200 mg, about 1000 mg, about or about 500 mg, about 400 mg, about 300 mg, about 200 mg, about 100 mg, about 90 mg, about 95 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, or about 10 mg total anthocyanins or total Boysenberry and blackcurrant anthocyanins. In particular aspects, the dosage unit may be about 50 mg to about 500 mg total anthocyanins or total Boysenberry and blackcurrant anthocyanins.

The dosage units as noted above may be administered once per day, twice per day, or three times per day, or more as needed. An exemplary, and non-limiting, daily dosage may be about 10 mg to about 1000 mg total anthocyanins or total Boysenberry and blackcurrant anthocyanins. The dosage may be adjusted for pediatric, geriatric, overweight, underweight, or other patients, where required.

If a Boysenberry juice, apple juice, or blackcurrant juice concentrate is made by standard commercial production methods (large or small scale), or obtained from commercial sources, the juice concentrate, including the combined Boysenberry and apple juice concentrates and the combined Boysenberry, apple and blackcurrant juice concentrates, may be administered at a dosage unit of about 0.5 to about 50 ml, about 0.5 to about 20 ml, about 0.5 to about 10 ml, about 1 to about 9 ml, about 2 to about 8 ml, about 3 to about 7 ml, about 4 to about 6 ml, or about 50, about 40, about 30, about 20, about 15, about 12.5, about 10, about 9, about 8, about 7, about 6, about 5, about 4, about 3, about 2, about 1, or about 0.5 ml of juice concentrate. In particular aspects, the dosage unit may be about 5 ml of juice concentrate. The various dosage units may be administered once per day, twice per day, or three times per day, or more as needed. Dosage modification can be made for patient size and age in accordance with known methods.

Each of the Boysenberry, apple, and blackcurrant concentrates will be rich sources of phenolics, anthocyanins, and other beneficial components. For example, a blackcurrant juice concentrate will be expected to include a total anthocyanin content (g/100 g) of at least 0.8, at least 0.9, at least 1.0, at least 1.1, at least 1.2, at least 1.3, at least 1.4, or at least 1.5. For exemplary anthocyanin quantitation methods, see (98) and (99). The blackcurrant juice concentrate will also be expected to include Vitamin C (ascorbic acid; mg/100 g) levels of at least 500, at least 550, at least 600, at least 650, at least 700, at least 750, at least 780, at least 800, at least 850, or at least 900. The blackcurrant juice concentrate will further be expected to include a total phenolics content (g/100 g) of at least 3.0, at least 3.2, at least 3.4, at least 3.6, at least 3.8, at least 4.0, at least 4.2, at least 4.4, at least 4.6, at least 4.8, or at least 5.0. For exemplary phenolics quantitation methods, see (100).

In certain circumstances, it may be desirable to isolate or enrich the polyphenols from the fruits being used. In particular, it may be advantageous to use the Boysenberry, apple, or blackcurrant to obtain polyphenol enriched compositions, phenolic concentrates, or compositions comprising isolated phenolics, e.g., isolated anthocyanins. For example, the compositions of the invention may be enriched for polyphenols such that their concentration is increased relative to the other components of the fruit, e.g., sugars. In particular aspects, the compositions of the invention may include polyphenols that have been isolated away from (e.g., purified from) the other components of the fruit. The particular polyphenols for isolation or enrichment are described in detail herein.

Methods of enriching and extracting polyphenols are widely known in the art (e.g., 81, 82). The resulting composition may include at least 2 times, at least 3 times, at least 4 times, at least 5 times, or at least 10 times the amount of polyphenols compared to the composition prepared without polyphenol enrichment or isolation steps. The polyphenol enriched compositions, phenolic concentrates, and compositions comprising isolated phenolics may be dried as a powder, and used in accordance with the present invention.

The dosage form may contain excipients, for example, one or more anti-adherents, binders, coatings, disintegrants, flavours, colours, sweeteners, lubricants, glidants, flow agents, anti-caking agents, sorbents, or preservatives. Useful excipients include but are not limited to: stearin, magnesium stearate, and stearic acid; saccharides and their derivatives, e.g., disaccharides: sucrose, lactose; polysaccharides and their derivatives, e.g., starches, cellulose or modified cellulose such as microcrystalline cellulose and cellulose ethers such as hydroxypropyl cellulose; sugar alcohols such as isomalt, xylitol, sorbitol and maltitol; proteins such as gelatin; synthetic polymers such as polyvinylpyrrolidone, polyethylene glycol; fatty acids, waxes, shellac, plastics, and plant fibres, e.g., corn protein zein; hydroxypropyl methylcellulose; crosslinked polymers, e.g., crosslinked polyvinylpyrrolidone (crospovidone), and crosslinked sodium carboxymethyl cellulose (croscarmellose sodium); sodium starch glycolate; silicon dioxide, fumed silica, talc, and magnesium carbonate.

It is expected that the Boysenberry compositions disclosed herein will include various components, for example, carbohydrates and polyphenols, and in particular, anthocyanidins. Anthocyanidins of interest include cyanidins and rutinosides, such as cyanidin-3-O-sophoroside, cyanidin-3-O-glucoside, epicatechin, cyanidin-3-O-glucosylrutinoside, cyanidin-3-O-rutinoside, cyanidin-3-(6'-p-coumaryl)glycoside-5-glycoside, cyanidin-3-O-glycoside, cyanidin-3,5-diglycoside, and cyanidin-3-O-2G-glucosylrutinoside. Also of interest are hydrolysable tannins such as ellagitannins and ellagic acid. The Boysenberry compositions of the invention may also include various carbohydrates, and in particular, various sugars, including neutral sugars. As to neutral sugars, the Boysenberry compositions may include one or more of fructose and glucose, as well as sucrose.

Similarly, the apple compositions as disclosed herein will encompass various components, including various carbohydrates and polyphenols. Of particular interest are phenolic compounds such as flavonoids and cinnamic and benzoic acid derivatives. Included are catechins, procyanidins, and hydroxycinnamates, and more particularly included are included are 3-hydroxy flavonoids such as anthocyanins, flavanols, and flavan-3-ols. Key individual compounds include epicatechin, catechin, procyanidin dimer B2, 5-caffeoylquinic acid, and quercetin glycosides. Dihydrochalcones such as phloridzin are particularly included as flavonoid precursors found in apples. Apple peels can be used to obtain high levels of polyphenols and flavonoids such as quercetin glycosides and cyanidin. Apple flesh and cores can be used to obtain high levels of chlorogenic acid. Particular cultivars can be used to maximise polyphenol levels. In particular, cider apples can be used to maximise procyanidins that are responsible for their astringency and bitterness. The apple compositions of the invention may also include various carbohydrates, and in particular, various sugars, including neutral sugars. As to neutral sugars, the apple compositions may include one or more of fructose, glucose, and sucrose.

As disclosed herein, the blackcurrant compositions of the invention will include various components, including sugars and polyphenols. Noted specifically are hydroxycinnamates such as chlorogenic and p-coumaroylquinic acids, and also anthocyanins, and flavonol glycosides. Of particular interest are polyphenol compounds such as delphinidin 3-O-glucoside; delphinidin 3-O-rutinoside; delphinidin-3-O-(6-p-coumaroyl)glucoside; cyanidin 3-O-glucoside; cyanidin 3-O-rutinoside; cyanidin 3-O-glucoside-6-p-cumaryl; peonidin 3-O-rutinoside; malvidin 3-O-rutinoside; neochlorogenic acid; p-coumaric acid glucoside; myricetin derivatives; quercetin 3-O-rutinoside; quercetin 3-O-galactoside; and quercetin 3-O-glucoside. For example, the skin may be used to obtain high levels of anthocyanins. The blackcurrant compositions of the invention may also include various carbohydrates, and in particular, various sugars, including neutral sugars. As to neutral sugars, the compositions in the invention may include one or more of fructose, glucose, and sucrose.

Methods of Using Compositions Comprising Boysenberry and Apple and Compositions Comprising Boysenberry, Apple and Blackcurrant As noted above, the Boysenberry compositions disclosed herein, including the compositions comprising Boysenberry and apple, and the compositions comprising Boysenberry, apple and blackcurrant, can be used to support or improve overall respiratory health and/or to treat or prevent various conditions of the respiratory tract, including inflammation, and respiratory disorders associated with inflammation, such as asthma, chronic obstructive pulmonary disease, reactive airway disease, airway fibrosis, and airway remodelling. Other conditions associated with inflammation in the respiratory tract include: allergy or allergic disorders, emphysema, bronchitis, respiratory bronchiolitis, interstitial lung disease, inflammatory airway disease, fibrosing alveolitis, intrinsic alveolitis, pulmonary eosinophilia, pulmonary vasculitis, pneumonia, interstitial pneumonia, desquamative interstitial pneumonia, lymphoid interstitial pneumonia, nonspecific interstitial pneumonia, eosinophilic pneumonia, pneumonitis, pleurisy (pleuritus), pleural effusion, cystic fibrosis, primary ciliary dyskinesia, acute respiratory distress syndrome (ARDS), sarcoidosis, dermatomyositis, toxocariasis, Wegener's granulomatosis, Langerhans cell histiocytosis, Sjogren's syndrome, Kartagener syndrome, vocal cord dysfunction, spasmodic croup, autoimmune disease such as lupus, reflexive vasomotor disease, and autonomic disorders. Additional factors associated with inflammation in the respiratory tract include smoking, air pollution, allergens, infection (e.g., viral or bacterial), certain medication (e.g., chemotherapeutic agents), radiation treatment, medical devices (e.g., ventilators), and surgery.

The compositions of the invention find use for treating or preventing respiratory tract inflammation, asthma, chronic obstructive pulmonary disease, airway fibrosis, airway remodelling, or other conditions described herein. As exemplary dosages, the compositions may be administered at dosages to obtain about 0.1 to about 200 mg/kg, about 0.2 to about 180 mg/kg, about 0.25 to about 150 mg/kg, about 0.5 to about 125 mg/kg, about 0.6 to about 100 mg/kg, about 0.7 to about 90 mg/kg, about 0.1 to about 50 mg/kg, about 0.1 to about 20 kg/mg, about 0.1 to about 10 mg/kg, about 0.1 to about 5 mg/kg, about 0.1 to about 1 mg/kg, about 1 to about 20 mg/kg, about 1 to about 10 mg/kg, 1 to about 5 mg/kg, or about 200 mg/kg, about 100 mg/kg, about 90 mg/kg, about 80 mg/kg, about 70 mg/kg, about 60 mg/kg, about 50 mg/kg, about 40 mg/kg, about 30 mg/kg, about 20 mg/kg, about 10 mg/kg, about 9 mg/kg, about 8 mg/kg, about 7 mg/kg, about 6 mg/kg, about 5 mg/kg, about 4 mg/kg, about 3 mg/kg, about 2 mg/kg, about 1 mg/kg, about 0.9 mg/kg, about 0.8 mg/kg, about 0.7 mg/kg, about 0.6 mg/kg, about 0.5 mg/kg, about 0.4 mg/kg, about 0.3 mg/kg, about 0.2 mg/kg, or about 0.1 mg/kg, of total anthocyanins or total Boysenberry anthocyanins in relation to patient body weight. In particular aspects, the dosage may be about 0.1 mg/kg to about 10 mg/kg. The dosages as indicated above may be administered once per day, twice per day, three times per day, or more, as needed. Administration may be made with food, or before a meal. The appropriate dosage and dosage form will be readily determined by a person of skill in the art.

Various routes of administration may be used for the compositions, including enteral administration and oral administration. Oral administration may be by tablet, capsule, sachet, drops, elixir, linctus, solution, emulsion, suspension, draught, puree, paste, syrup, gel, jelly, tonic, or other known means. Enteral administration may be by duodenal tubing or gastric tubing, including nasogastric tubing. Different means of administration are known in the art and may be utilised by a skilled person. The compositions disclosed herein are not limited to a particular form for administration.

It may be useful to add one or more phenolic compounds to the compositions of the invention, to further supplement the phenolic activity therein. Exemplary compounds include but are not limited to: phenolic derivatives such as phenolic acid, and flavonoids such as lignins, proanthocyanidins, anthocyanins, anthocyanidins, isoflavones, catechins, tannins, quercetin, naringenin, and hesperidin. Specific anthocyanin compounds of interest are described herein. Particularly encompassed are phenolic compounds extracted from one or more of: tea, cocoa, wine, soybeans, feijoa, citrus fruits, apples, pears, grapes, berries, and kiwifruit. Specific phenolics include but are not limited to: ellagic acid, chlorogenic acid, catechin, epicatechin, kaemferol, E-caffeoyl-3-glucoside, E-caffeoyl-4-glucoside, neochlorogenic acid, phlorizin, procyanidin B1 and B2, quercetin, quercetin rhamnoside, and quercetin rutinoside.

As additional aspects, the compositions of the invention may be co-administered with one or more respiratory aids. A respiratory aid may be a medication, prescription or non-prescription, or an alternative treatment, such as a herbal remedy, or an essential oil, e.g., for vaporisation and/or inhalation. Of particular interest is use of the composition of the invention as a respiratory treatment during and/or following other respiratory treatments. For example, the composition may be formulated as a combined dosage form with one or more medicines or alternative treatments. Alternatively, the Boysenberry composition may be administered as a separate dosage form along with one or more medications or alternative treatments. A respiratory aid may have one or more physiological effects, for example, anti-inflammatory, anti-spasmodic, bronchodilation, and/or muscle relaxation effects. Any respiratory aid may be long or short acting, and may be directed to a particular disorder, such as asthma, chronic obstructive pulmonary disease, etc.

Exemplary medications include but are not limited to bronchodilators, including short-acting bronchodilators such as albuterol (e.g., Vospire ER), levalbuterol (e.g., Xopenex), ipratropium (e.g., Atrovent), albuterol/ipratropium (e.g., Combivent), corticosteroids such as fluticasone (e.g., Flovent, Flovent Diskus, Flovent HFA), budesonide (e.g., Pulmicort, Pulmicort Flexhaler), mometasone (e.g., Asmanex), beclomethasone (e.g., QVAR), flunisolide (e.g., Aerospan), prednisolone, methylprednisolone, and hydrocortisone, methylxanthines such as theophylline (e.g., Theochron, Theo-24, Elixophyllin), long-acting bronchodilators such as aclidinium (e.g., Tudorza), arformoterol (e.g., Brovana), formoterol (e.g., Foradil, Perforomist), glycopyrrolate (e.g., Seebri Neohaler), indacaterol (e.g., Arcapta), olodaterol (e.g., Striverdi Respimat), salmeterol (e.g., Serevent), tiotropium (e.g., Spiriva), and umeclidinium (e.g., Incruse Ellipta), combinations of two or more long-acting bronchodilators such as glycopyrrolate/formoterol (e.g., Bevespi Aerosphere), glycopyrrolate/indacaterol (e.g., Utibron Neohaler), tiotropium/olodaterol (e.g., Stiolto Respimat), umeclidinium/vilanterol (e.g., Anoro Ellipta).

Further exemplary medications include but are not limited to combinations of inhaled corticosteroid(s) and long-acting bronchodilator(s) such as budesonide/formoterol (e.g., Symbicort), fluticasone/salmeterol (e.g., Advair, Advair Diskus), and fluticasone/vilanterol (e.g., Breo Ellipta), phosphodiesterase-4 inhibitors such as roflumilast (e.g., Daliresp), beta agonists, including short-acting beta agonists such as albuterol (e.g., ProAir HFA, Ventolin HFA), and levalbuterol (e.g., Xopenex HFA), anticholinergics such as ipratropium bromide (e.g., Atrovent HFA), long-acting beta antagonists (LABAs) such as formoterol (Perforomist), and salmeterol (e.g., Serevent Diskus), leukotriene modifiers such as montelukast (Singulair), zafirlukast (Accolate), and zileuton (e.g., Zyflo, Zyflo CR), immunomodulators such as mepolizumab (Nucala), omalizumab (e.g., Xolair), reslizumab (e.g., Cinqair), bronchodilators such as epinephrine (e.g., Primatene Mist, Bronkaid, Asthmahaler), ephedrine, and theophylline-ephedrine (e.g., Primatene tablets).

EXAMPLES

The examples described herein are provided for the purpose of illustrating specific embodiments of the invention and are not intended to limit the invention in any way.

Example 1: OVA-Induced Chronic Airway Inflammation and Oral Treatment with Boysenberry Overview Lung fibrosis negatively impacts on lung function in chronic asthma and is linked to the development of profibrotic macrophage phenotypes. Epidemiological studies have found that lung function benefits from increased consumption of fruit high in polyphenols. However, previous studies have not investigated Boysenberry compositions, or effects on fibrotic or remodelling in airway systems.

The inventors investigated the effect of Boysenberry consumption, in both therapeutic and prophylactic treatment strategies in a mouse model of chronic antigen-induced airway inflammation. Boysenberry consumption reduced collagen deposition and ameliorated tissue remodelling alongside an increase in the presence of CD68+CD206+ arginase alternatively activated macrophages in the lung tissue. The decrease in tissue remodelling was associated with increased expression of profibrolytic matrix metalloproteinase-9 protein in total lung tissue.

The inventors identified alternatively activated macrophages in the mice that consumed Boysenberry as a source of the matrix metalloproteinase-9. The inventors hypothesise that oral Boysenberry treatment moderate chronic tissue remodelling by supporting the development of profibrolytic alternatively activated macrophages expressing matrix metalloproteinase-9. Regular Boysenberry consumption therefore has the ability to moderate chronic lung remodelling and fibrosis in asthma and other chronic pulmonary diseases.

Materials

Anti-actin (clone AC-15), ovalbumin (OVA), 4% formalin, Tween 20, trans-hydroxyproline, 3,3'-diaminobenzidine (DAB) substrate, ketamine/xylazine, and all other chemicals were obtained from Sigma (Auckland, NZ). Alum was obtained from Serya (Heidelberg, Germany). The Boysenberry juice was obtained as New Zealand 65 Brix Boysenberry juice concentrate kindly provided by Berryfruit Export NZ, currently trading as Boysenberries New Zealand Ltd (Nelson, New Zealand). The 65 Brix Boysenberry juice concentrate from Berryfruit Export NZ was diluted in sterile water to obtain a concentrate of 100 mg/ml total anthocyanins. From this, a further dilution was prepared to obtain a dosage of 10 mg/kg of total anthocyanins. This further dilution is noted as Boysenberry solution.

Anti-mouse polyclonal inducible nitric oxide synthase (iNOS) (ab3523), arginase, TIMP-1 (ab38978), and MMP-9 (ab38898) were obtained from Abcam (Cambridge, UK). Antibodies against mouse CD68 (clone FA-11) CD3e, CD8a, CD4, CD11b, CD11c, and Gr-1 were obtained from BioLegend (San Diego, CA) and anti-CD206 (clone MR5D3) was obtained from AbDSerotec (Oxford, UK). Anti-mouse SiglecF, MHCH, and CD45 were from BD Biosciences (San Jose, CA).

TGFβ ELISA kit was obtained from R&D Systems (Minneapolis, MN). Vectastain Elite ABC staining kit was from Vector Laboratories (Burlingame, CA). Bio-Plex multiplex cytokine assays for IL-4, IL-5, IL-6, IL-13, and IFNγ, DC Lowry protein assay kit, and PVDF membrane were from Bio-Rad (Hercules, CA). BSA, NuPage 4-12% gels, MES running buffer, sample loading buffer, Novex sharp prestained, and MagicMark XP protein standards and all other buffers were from Life Technologies (Auckland, NZ).

Animals

C57BL/6J male mice were bred and group housed (5 per cage) in conventional polycarbonate cages with a filter top, in a specific pathogen-free animal facility at the Malaghan Institute of Medical Research, Wellington, New Zealand. All experimental procedures were approved by the Victoria University of Wellington Animal Ethics Committee (approval number 2011R3M).

Mice were maintained on a 12-h light-dark cycle, at 21±2° C. ambient temperature with freely available irradiated standard laboratory rodent chow (Specialty Feeds, Glen Forrest, WA, Australia) and acidified water.

OVA-Induced Chronic Airway Inflammation and Oral Boysenberry Treatment

Six-week-old mice were randomized into experimental groups (n=10 per group) and primed intraperitoneally (i.p.) with 100 μg OVA in 200 μl alum adjuvant on day 0. On day +7 mice were challenged intranasally (i.n.) with 100 μg OVA or PBS.

Figure 6A:
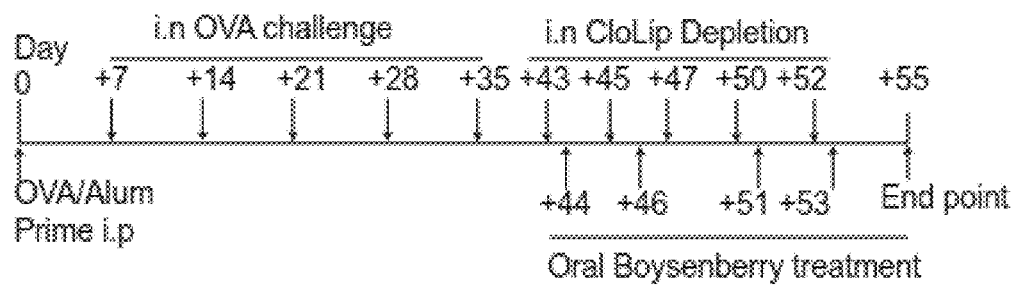
FIGS. 6A-6C. Depletion of lung macrophages reduced the effect of oral Boysenberry treatment on OVA-induced chronic lung inflammation.

To establish chronic disease the i.n. challenge was repeated weekly (FIGS. 1A and 6A). Four days following the last i.n. OVA challenge mice were euthanized (ketamine/xylazine overdose) and bronchial-alveolar lavage fluid (BALF), serum, mediastinal lymph nodes and lung tissue were collected.

For the treatment studies mice were fasted overnight before being orally gavaged with 250 μl of Boysenberry solution (see above); dosage at 10 mg/kg of total anthocyanins) or sterile water on the day of OVA challenge and again 2 days post-OVA challenge (FIGS. 1A and 6A).

Clodronate Liposome Depletion of Lung Macrophages and Tissue Analysis

Clodronate liposomes were prepared as previously described (58). Chronic OVA-induced tissue damage was established over 5 weeks. Mice were then treated intranasally with 100 μl clodronate liposomes the day prior to each oral gavage with 250 μl of Boysenberry solution (see above; dosage at 10 mg/kg of total anthocyanins) or sterile water (FIG. 6A). Two days following the last oral gavage mice were euthanized (ketamine/xylazine overdose) and BALF, serum, mediastinal lymph nodes, and lung tissue were collected.

Cells isolated from the BALF were stained for key surface markers to identify monocytes/macrophages (CD45+/CD11b+/Cd11c+/MHCIIlow) and eosinophils (CD45+/CD11b+/siglecF+) by flow cytometry as previously described (52). TGFβ ELISA and Bio-Plex multiplex cytokine assays were performed on lung tissue supernatants following the manufacturer's instructions. Lung tissue was fixed in 4% formalin, sectioned, and stained with hematoxylin and eosin (H&E), Masson's Trichrome or Alcian blue-periodic acid-Schiff (AB-PAS) stains (Dept. of Pathology, Wellington School of Medicine, University of Otago, Wellington, NZ).

Further sections were cut for immunological labelling. Lung sections were incubated with biotin-conjugated MMP-9, then labelled with DAB and counter-stained with hematoxylin. Other tissue sections were incubated with fluorescently labelled CD68 (31), CD206 (57), and arginase or MMP-9 (44), then counterlabelled with DAPI-containing mounting medium.

All sections were imaged on an Olympus BX51 compound microscope and captured by using cellSens (Olympus NZ) software, bright light in colour and fluorescence in grayscale. Fluorescence images were processed (cropped, false coloured, and merged) in Pixelmator image software (Vilnius, Lithuania). Fluorescently labelled cells were quantified by four independent, blinded observers. Cells were counted in random fields from multiple animals and scored as negative, single positive, or double positive for CD68, CD206, arginase, or MMP-9. Data were expressed as a percentage of total cells counted.

Biochemical and Molecular Biological Tissue Analysis and Statistical Analysis

Biochemical and molecular biological tissue analysis. Lung tissue was snap frozen and stored at $-70°$ C. Lung collagen was quantified by the hydroxyproline assay as previously described (2). For Western blotting, tissue was homogenized in protein lysis buffer (Tris·HCl, NaCl, 10% Nonidet P-40, 10% sodium deoxycholate, 100 nM EDTA, pH 7.4 with protease and phosphatase inhibitors). Protein concentration was quantified by a Lowry protein assay as per the manufacturer's instruction.

Samples (30 µg protein) were separated by SDS-PAGE gel electrophoresis under reducing conditions and transferred onto PVDF membrane. Nonspecific protein binding was blocked with 3% BSA (10 mM PBS with 0.2% Tween 20) and the membranes were probed overnight with primary antibodies specific to iNOS (64), arginase (53), MMP-9 (44), and TIMP-1 (55), or β-actin (12) loading control (4° C.). Membranes were washed and incubated with horseradish peroxidase-conjugated secondary antibodies and visualized by chemiluminescence on a Carestream Gel Logic Pro 6000 imager. Protein expression was densitometrically quantified and normalized to β-actin with Imagers Gel analysis tool (50). Images were processed and cropped in Pixelmator image software.

Data were analysed by one-tailed Student's t-test for comparisons between two groups or one-way ANOVA with Tukey's post hoc test for comparisons between three or more groups as indicated (Prism, GraphPad, San Diego, CA). $P<0.05$ or less was considered statistically significant.

Results—Boysenberry Consumption Ameliorates OVA-Induced Chronic Airway Inflammation To investigate the effect of Boysenberry treatment on established lung remodelling, mice were challenged weekly with intranasal OVA for 5 weeks, then challenged weekly with OVA for an additional 5 weeks alongside weekly oral treatment with Boysenberry (FIG. 1A).

As shown in FIG. 1B, lung tissue from OVA-challenged mice exhibited increased cellular infiltrate and loss of lung structure. OVA-induced cellular infiltrate and lung damage were decreased in Boysenberry-treated mice (FIG. 1B). Staining of lung tissue for mucus production identified fewer mucus-positive cells in OVA-challenged mice receiving Boysenberry treatment compared with OVA only-challenged mice (FIG. 1C). Boysenberry treatment alone had no effect on cellular infiltration, lung structure, or mucus production.

Results—Boysenberry Treatment Increases AAMs in the Lung of OVA-Challenged Mice

Figure 2B:
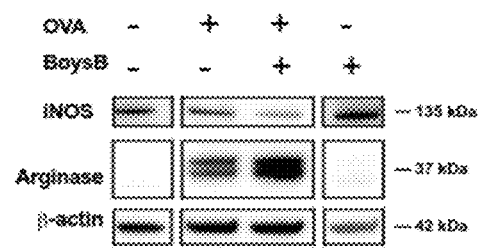
Figure 2C:
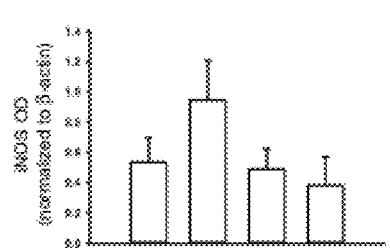
Figure 2D:
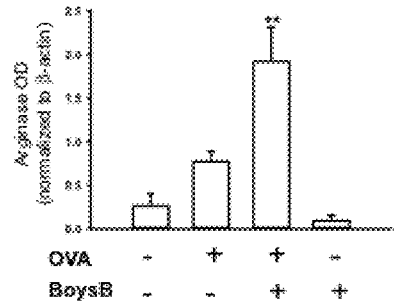

H&E-stained lung tissue sections showed more macrophages in OVA/Boysenberry-treated mice compared with OVA mice (FIG. 2A). Immunoblot analysis of lung tissue identified a decrease in iNOS expression in the lung tissue of OVA/Boysenberry-treated mice compared with OVA challenge alone (FIGS. 2B and 2C). At the same time, an increase was observed in arginase expression in OVA-challenged mice (FIGS. 2B and 2D). that was further enhanced in OVA-challenged mice treated with Boysenberry. Arginase expression was not affected by Boysenberry treatment alone.

AAMs expressing arginase are closely associated with lung remodelling (29). To determine whether the observed lung macrophages were alternatively activated, lung tissue was stained with fluorescently labelled antibodies for the macrophage marker CD68 and the AAM markers CD20 and arginase.

Figure 3A:
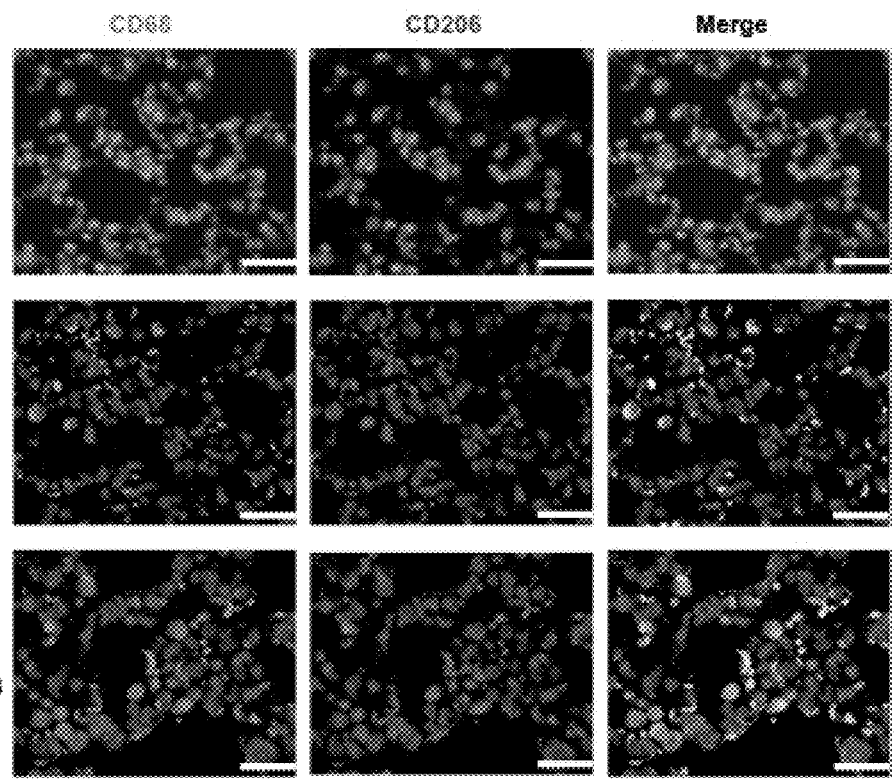
FIGS. 3A-3B. Boysenberry treatment increases the accumulation of arginase+ alternatively activated macrophages during OVA-induced chronic lung inflammation. Representative immunofluorescent labelling of lung tissue from 10-week OVA-challenged mice with and with-out Boysenberry treatment.
Figure 3B:
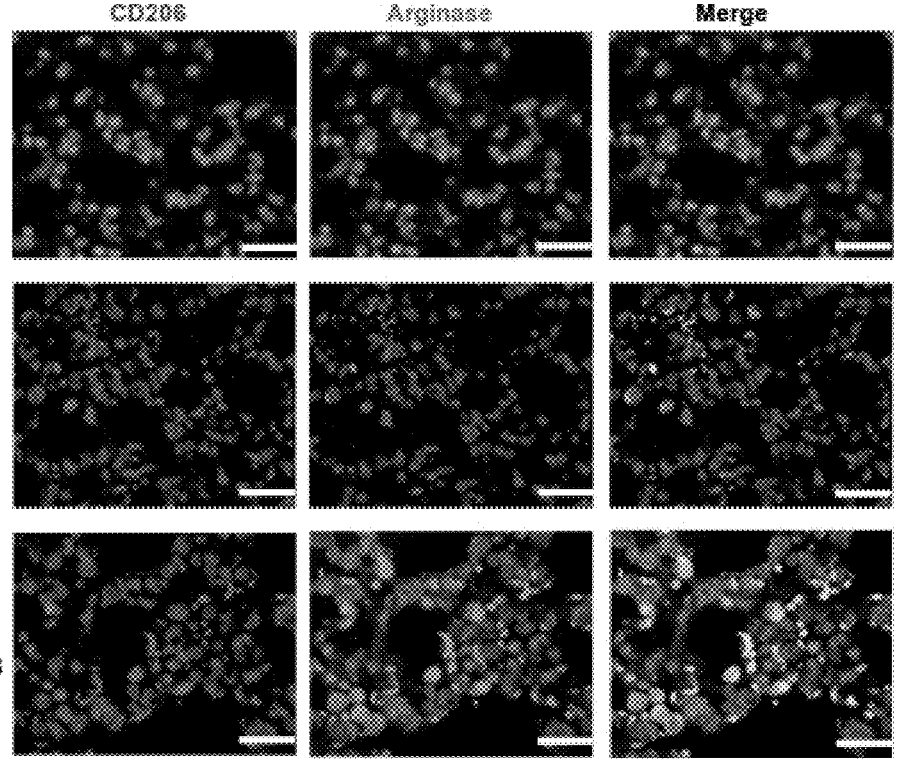

Lung tissue from OVA/Boysenberry-treated mice showed an increase in CD68+CD206+arginase+macrophages compared with OVA-challenged mice (FIGS. 3A-3B). Quantitative analysis of the CD68+CD206+arginase+macrophages further confirmed a significant increase in the percentage of CD68+CD206+arginase+macrophages in the lung tissue of OVA/Boysenberry-treated mice compared with OVA-challenged mice ($60.00\pm3.54\%$ compared with $23.47\pm5.61\%$, $P<0.001$, one-tailed Student's t-test). Together these data identify an increase in the number of lung macrophages expressing an alternatively activated phenotype in OVA-challenged mice receiving Boysenberry treatment.

Results—Boysenberry Treatment Decreases OVA-Induced Collagen Deposition and Increases MMP-9 Expression in the Lung Increased AAMs and arginase expression are commonly associated with tissue fibrosis (14, 27, 66); therefore the effect of Boysenberry treatment was investigated for OVA-induced collagen deposition in the lung. Following this the levels of hydroxyproline were measured in the lung tissue as a surrogate marker of collagen deposition (2, 63).

OVA challenge alone resulted in abnormal collagen deposition in the airways with signs of collagen invasion throughout the lung tissue that was abrogated in the lungs of OVA/Boysenberry-treated mice (FIGS. 4A-4E). In addition, there was a significant drop in the levels of hydroxyproline in the lungs of OVA-challenged mice treated with Boysenberry, confirming that Boysenberry treatment ameliorated OVA-induced collagen deposition (FIG. 4B). Boysenberry restored the OVA-induced decrease in the levels of TGFβ in the lung (FIG. 4C) but did not affect the levels of IL-4, IL-5, IL-6, IL-13, or IFNγ (data not shown).

To determine how Boysenberry treatment could be moderating lung fibrosis the expression of MMP-9 was measured in the lung tissue by immunoblot.

It was determined that MMP-9 expression was increased in OVA-challenged mice treated with Boysenberry compared with mice challenged with OVA alone (FIG. 4D). Boysenberry treatment alone did not affect MMP-9 levels in the lung. Tissue inhibitor of matrix metalloproteinases-1 (TIMP-1) is the endogenous inhibitor of MMP-9 (49). The ratio of TIMP-1/MMP-9 expression significantly increased in the lung tissue of chronic OVA-challenged mice and this increase was reversed with Boysenberry treatment (FIG. 4E). These results indicate that Boysenberry-mediated reduction in collagen deposition and tissue remodelling was associated with elevated production of fibrolytic MMP-9 and a subsequent rebalance in the ratio of TIMP-1/MMP-9.

Figure 5A:
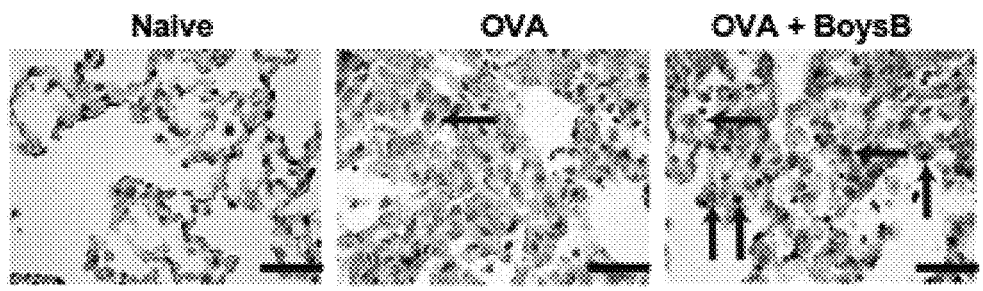
FIGS. 5A-5B. Boysenberry treatment increases MMP-9 expression by alternatively activated macrophages in lung tissue during OVA-induced chronic lung inflammation.
Figure 5B:
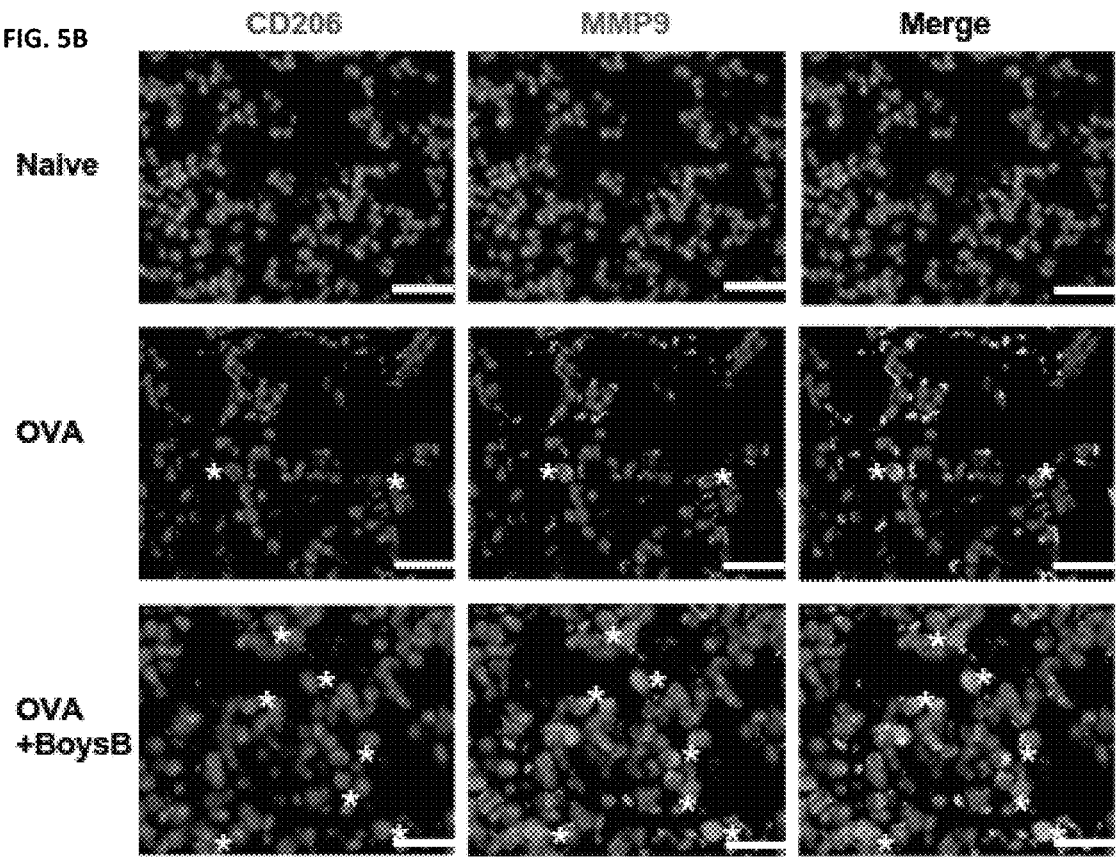

Results—Alternatively Activated Macrophages are a Source of MMP-9 Protein in the Lungs of OVA/Boysenberry-Treated Mice Lung tissue slides were analysed to identify potential cellular sources of MMP-9. DAB-MMP-9 staining identified a high degree of MMP+ cells exhibiting macrophage morphology in OVA/Boysenberry-treated mice compared with OVA-treated controls (FIG. 5A). Immunofluorescent staining (FIG. 5B) and quantitative analysis of the lung tissue confirmed that there were more MMP-9+/CD206+/CD68+ cells present in OVA/Boysenberry-treated lungs than those challenged with OVA alone (39.30±6.39 vs. 21.07±5.82%; P<0.05, one-tailed Student's t-test). These results identify CD206+/CD68+ AAMs as a source of the increased MMP-9 protein levels.

Figure 6B:
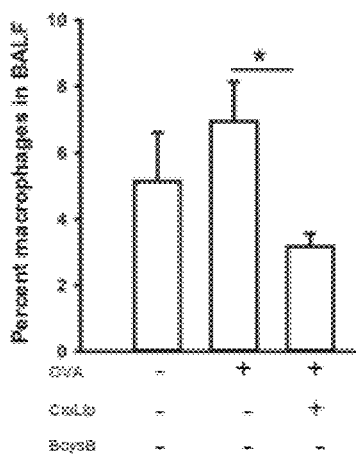
Figure 6C:
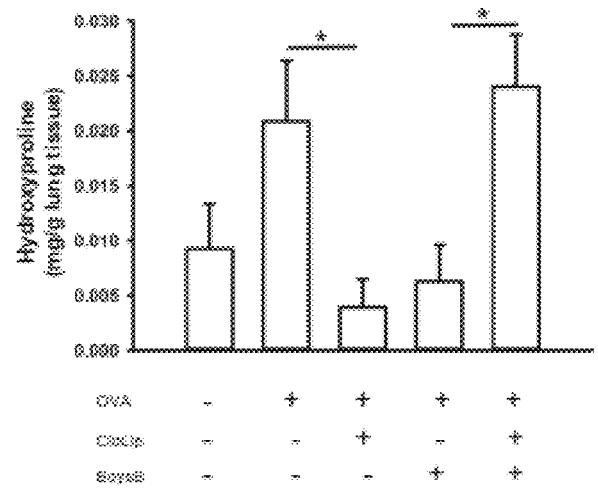

Results—Depletion of Lung Macrophages Reduces the Beneficial Effect of Boysenberry Consumption on Tissue Remodelling in Established Chronic Lung Inflammation Next, the inventors looked at the effect of depleting lung macrophages on the beneficial effects of Boysenberry on chronic lung inflammation. Macrophages were depleted by administration of clodronate liposomes after establishing chronic lung inflammation and remodelling, and prior to administration of each Boysenberry treatment (FIG. 6A). It was confirmed that significant depletion of the lung macrophages had been obtained by flow cytometry (FIG. 6B) and that this was associated with a significant reduction in hydroxyproline levels in the lung of OVA-challenged mice treated with Boysenberry (FIG. 6C). These data indicate that Boysenberry requires macrophages to mediate its beneficial effects on lung tissue remodelling.

Results—Boysenberry Treatment Prophylactically Prevents OVA-Induced Airway Inflammation Finally, the effect of Boysenberry treatment was tested using a prophylactic dosing regimen (FIG. 7A). Again, Boysenberry treatment resulted in abrogation of OVA-induced tissue remodelling and significantly reduced cells in the lung lavage fluid (FIGS. 7B-7D), This was associated with lower levels of hydroxyproline in the lung tissue and a decrease in the ratio of TIMP-1/MMP-9 expression (FIGS. 7E-7G).

Discussion

Fruit consumption has been linked with improved lung function in asthma sufferers and the amelioration of acute airway inflammation in experimental models (16, 19, 40). However, no findings have been established in these studies in relation to Boysenberry compositions, airway fibrosis, or airway remodelling, and it is well established that other known asthma treatments have failed to address airway remodelling.

It is demonstrated herein that consumption of a Boysenberry composition moderates chronic lung remodelling and fibrosis in both a therapeutic and a prophylactic setting. Furthermore, the data indicate that macrophages play an important role in Boysenberry-mediated protection and that this protection may result from modulation of AAMs and increased MMP-9 activity.

An increase in both arginase activity (26, 27, 41) and AAMs (4, 9) is often linked with asthma pathogenesis. However, there is evidence that the presence of AAMs does not specifically underpin the development of allergic asthma (37), which indicates that AAMs may play an alternative role.

As shown herein, the Boysenberry treatment increased the population of arginase-positive AAMs alongside a drop in iNOS expression in the lung tissue of chronic OVA-challenged mice. Arginase and iNOS play an interactive role in regulating lung inflammation and repair (34, 35, 66). Where iNOS activity is associated with active inflammation, arginase expression is indicative of a switch toward inflammatory resolution (35, 63). Boysenberry consumption therefore appears to rebalance the lung environment, supporting inflammation resolution by modulating the functional phenotype of AAMs in the lung.

The presence of AAMs has been associated with decreased Th-2 cytokine production in lung inflammation (36, 42). However, it was determined that no changes in the levels of Th-2 cytokines IL-4, IL-5, and IL-13 with Boysenberry consumption following OVA challenge. This indicated that inhibition of proinflammatory Th-2 cytokine production by AAMs was not contributing to the protective effect of Boysenberry treatment.

Clinical and animal data indicate that the role of MMP-9 in asthma is multifaceted. Lung macrophages producing MMP-9 have been identified in both experimental and clinical settings (1, 5, 49). Elevated levels of active MMP-9 have been found in plasma and sputum samples from patients with asthma, compared with healthy controls (3, 23). Increased MMP-9 expression has been correlated with acute asthma exacerbation, including increased lung eosinophilia (6, 23). Conversely, an increase in MMP-9 levels has been associated with improved lung function in airway disease (25, 65). MMP-9 overexpression has also been shown to have beneficial effects in a model of pulmonary fibrosis (5). In contrast, data from MMP-9 knockout mice show a partial reduction in the development of asthma symptoms and reduced remodelling but, in some cases, a lack of MMP-9 has been shown to exacerbate disease (15, 24, 32).

MMP-9 exerts many downstream effects on different immune parameters, including the activation of both pro- and anti-inflammatory cytokines (15). Nevertheless, the data shown herein indicate that Boysenberry-induced protection of lung tissue from chronic collagen deposition and fibrosis is orchestrated, in part, through the generation of fibrolytic AAM producing MMP-9. Consistent with this, the data show that depletion of macrophages during the resolution phase of inflammation leads to increased collagen deposition with Boysenberry consumption. A similar resolution-promoting role for macrophages has been illustrated in bleomycin-induced pulmonary fibrosis (14).

Matrix metalloproteinases are regulated by their natural inhibitors TIMPs, and high TIMP-1/MMP-9 ratios are proposed to favour collagen deposition and lung remodelling (21, 28, 38). Here a significant increase was observed in the ratio of expression of TIMP-1/MMP-9 in the lung tissue of chronic OVA-challenged mice and this was reversed by Boysenberry treatment. The drop in the ratio of TIMP-1/MMP-9 in Boysenberry-treated mice therefore represents a potentially beneficial re-adjustment in the regulation of collagen deposition and breakdown.

TGFβ is associated with both normal (20) and pathological (17, 22, 56) tissue repair processes through its role in extracellular matrix production. In this study, it was observed that chronic OVA challenge led to a decrease in TGFβ levels that was reversed by Boysenberry consumption. There is evidence that TGFβ lowers the TIMP-1/MMP-9 ratio, thus favouring a more fibrolytic environment (18, 54, 56). As such the increase in TGFβ levels observed in the lungs of OVA-challenged mice following Boysenberry treatment could serve to limit excessive tissue fibrosis and inappropriate remodelling during lung repair by lowering the TIMP-1/MMP-9 ratio. TGFβ is also known to stimulate fibroblast contraction for normal tissue repair (20), which could likewise contribute toward the beneficial effects of Boysenberry treatment. As such the elevation of TGFβ has the potential to promote an anti-inflammatory, pro-resolution environment within the lung via multiple mechanisms.

The results from these studies show that Boysenberry administration exhibits a beneficial effect on chronic lung fibrosis in both a therapeutic and a prophylactic setting. This indicates that Boysenberry consumption may help avoid inappropriate fibrotic remodelling in cases of both poorly controlled and well-controlled asthma. Finally, these findings provide the first evidence that Boysenberry consumption could be used to support the development of fibrolytic AAMs with the potential to regulate appropriate lung remodelling in asthma and other lung conditions exhibiting fibrotic pathologies.

In summary, these findings have showed that Boysenberry compositions may be used to decrease inflammation and aberrant collagen deposition in the respiratory tract, and thereby find use in the treatment and prevention of various disorders of the airways, including asthma, chronic obstructive pulmonary disease, reactive airway disease, airway fibrosis, and airway remodelling.

Example 2: OVA-Induced Acute Airway Inflammation and Oral Treatment with Boysenberry and Apple Materials and Methodology Six-week-old mice treated and assessed as in Example 1, noted above with the following modifications. The tested solutions included: Boysenberry 1 and Boysenberry 10, 0.67% or 6.7%, respectively, apple 1 and apple 10 10, 1.87% and 18.7%, respectively, BerriQi™ Boysenberry with apple 1 and BerriQi™ Boysenberry with apple 10, 0.67%/1.87% and 6.7%/18.7%, respectively. Commercial Boysenberry juice concentrate was obtained as described in Example 1. Apple juice concentrate was supplied from Infruit Ltd (Titirangi, Auckland, New Zealand), as manufactured by Profruit (2006) Ltd (Hastings, New Zealand).

For the 18.7% solutions, 18.7 g juice concentrate was diluted in 100 g water. For the 6.7% solutions, 6.7 g juice concentrate was diluted with 100 g water. For the 1.87% solutions, 1.87 g juice concentrate was diluted in 100 g water. For the 0.67% solutions, 0.67 g juice concentrate was diluted in 100 g water. For the combined 6.7%/18.7% solutions, 6.7 g and 18.7 g for the respective juice concentrate was diluted in 100 g water. For the combined 0.67%/1.87% solutions, 0.67 g and 1.87 g for the respective juice concentrate was diluted in 100 g water. In reference to the combined solutions, the Boysenberry to apple percentage was 27% to 73%. Prepared in parallel, BerriQi™ Boysenberry with apple test solutions were heated for 8 hours at 80° C. prior to administration to test for deactivation of anti-inflammatory activity.

The protocol for testing the combined administration of Boysenberry with apple administration was based on previously published methods for inducing allergic airways inflammation (52). The protocol for acute inflammation utilised an 11 day model. To evaluate the efficacy of Boysenberry, apple, combined Boysenberry and apple administration, and determine the effect of diluting the treatments 10-fold the following treatment groups were tested: 1) Baseline control (no disease); 2) Disease control; 3) Apple 10 (at 18.7%)+disease; 4) Apple 1 (at 1.87%)+disease; 5) Boysenberry 10 (at 6.7%)+disease; 6) Boysenberry 1 (at 0.67%)+disease; 7) BerriQi™ Boysenberry with apple 10 (at 6.7/18.7%)+disease; 8) BerriQi™ Boysenberry with apple 1 (at 0.67/1.87%)+Disease; 9) 'Cooked' BerriQi™ Boysenberry with apple (at 6.7/18.7%)+disease. Each group included 10 animals. Experiments were repeated three times. Statistical analysis was performed as described in Example 1.

As per prior employment of this model, the following dosing/challenge regimen was used. Mice were primed for allergic airways inflammation 7 days prior to the challenge and samples were collected 4 days post challenge. Mice were administered (treated) with 250 μl of the noted treatments or water (control) on day 0 and day +2 (see below). For the Boysenberry 10 test solutions (Boysenberry 10 and BerriQi™ Boysenberry with apple 10), the dosage was administered to deliver 4.87 mg/kg total anthocyanins. For the Boysenberry 1 test solutions (Boysenberry 1 and BerriQi™ Boysenberry with apple 1), the dosage was administered to deliver 0.487 mg/kg total anthocyanins.

The following samples were collected: 1) lung wash; 2) lung tissue; 3) mediastinal lymph node; 4) blood. These samples were analysed for the following as per the methodologies outlined in (52): 1) total cell counts (and cellular composition): lung wash, lung tissue, and lymph node; 2) cytokine and chemokine production including IL-4, IL-5, IL-6, IL-10, IL-13, CCL11, IFNγ: lung wash, lung tissue and blood; 3) IgE, IgG1: blood only. Cytokine levels were tested using BioLegend LEGENDplex™ multi-analyte flow assay kit in accordance with the manufacturer's instructions.

Results

Figure 8:
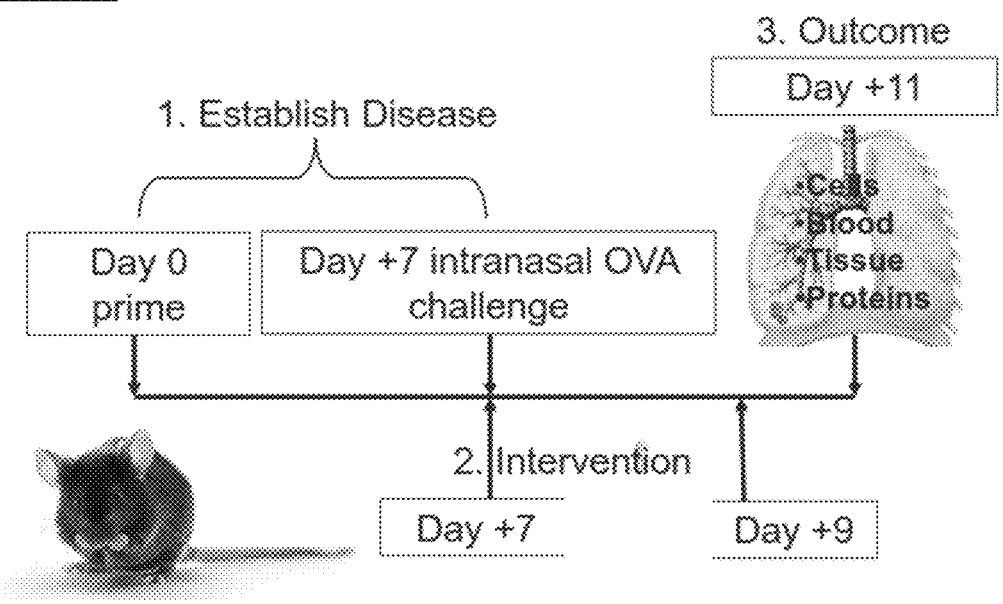
FIG. 8. Schematics for experiments testing Boysenberry treatment combinations in a model of acute allergic airways inflammation.

FIG. 8 shows the testing schematic. From the results obtained, ovalbumin challenge increased the appearance of inflammatory cells within the lung. This increase was reduced by particular treatments back to naïve levels, i.e., without OVA addition.

Figure 9:
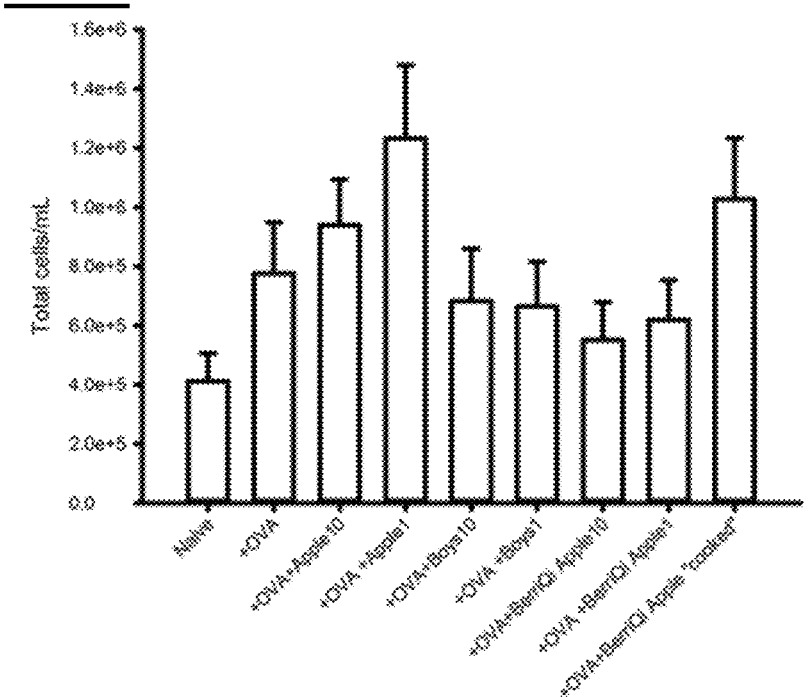
FIG. 9. Treatment utilising BerriQi™ Boysenberry with apple administration reduced immune cell numbers in model of acute allergic airways inflammation. Total cell infiltration into the lung following ovalbumin (OVA)-induced allergic airways infiltration. Total bronchioalveolar lavage fluid (BALF) cell numbers were determined 4 days post-OVA challenge (n=10 per intervention group).

The results demonstrated increased total immune cell infiltration into the lung in mice challenged intranasally with the allergen, OVA (FIG. 9). Treatment with apple alone did not reduce the cellular infiltration. BerriQi™ Boysenberry with apple reduced the cellular infiltration at both concentrations tested, and this was reversed when the BerriQi™ Boysenberry with apple was heated to 80° C. for 8 hours.

Figure 10:
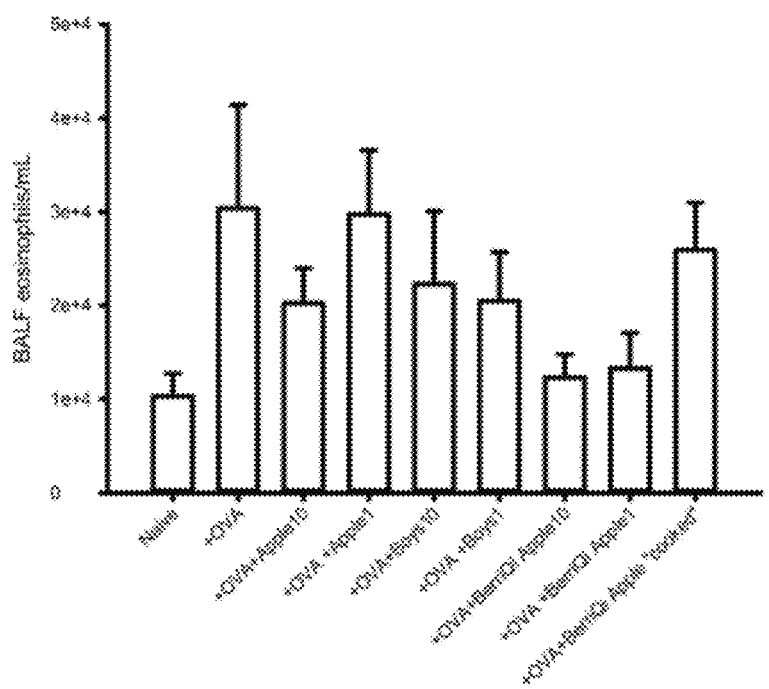
FIG. 10. Treatment utilising BerriQi™ Boysenberry with apple administration reduced eosinophil numbers in model of acute allergic airways inflammation. Eosinophil infiltration into the lung following an ovalbumin (OVA)-induced allergic airways infiltration. Total bronchioalveolar lavage fluid (BALF) eosinophil cell numbers were determined 4 days post-OVA challenge (n=10 per intervention group). BerriQi™ concentrates and the other concentrates are described in Example 2, below.
Figure 11:
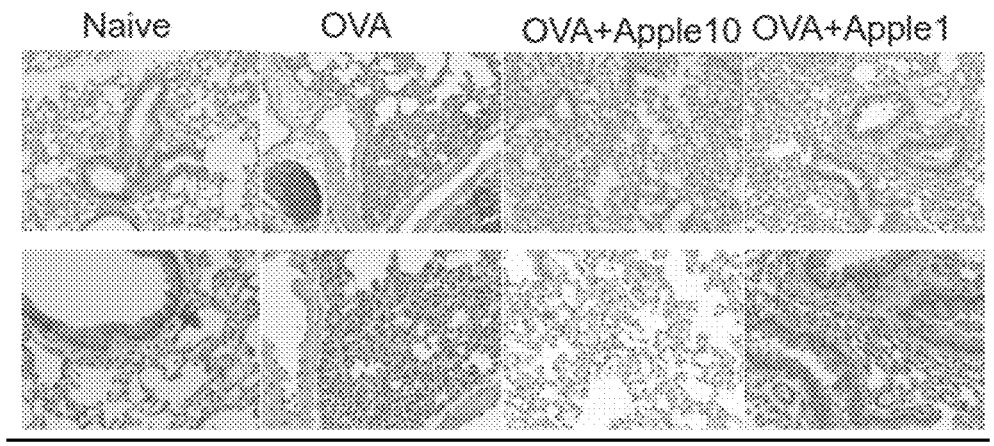
FIG. 11. Treatment utilising BerriQi™ Boysenberry with apple administration in model of acute allergic airways inflammation. Haematoxylin and eosin staining of lung tissues following apple treatment.
Figure 14:
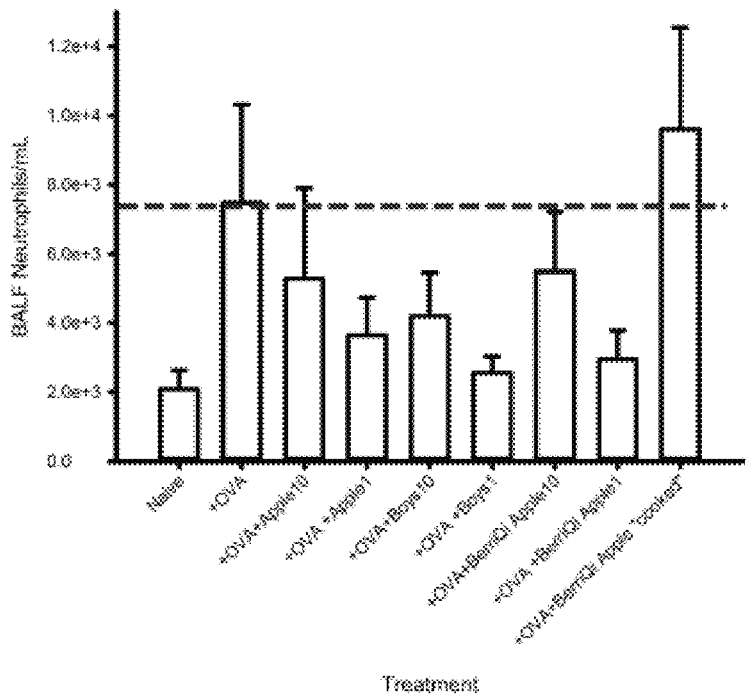
FIG. 14. Treatment utilising BerriQi™ Boysenberry with apple administration reduced neutrophil numbers in model of acute allergic airways inflammation. Neutrophil infiltration into the lung following ovalbumin (OVA)-induced allergic airways infiltration. Total bronchoalveolar lavage fluid (BALF) neutrophil cell numbers were determined 4 days post-OVA challenge (n=10 per intervention group).
Figure 15:
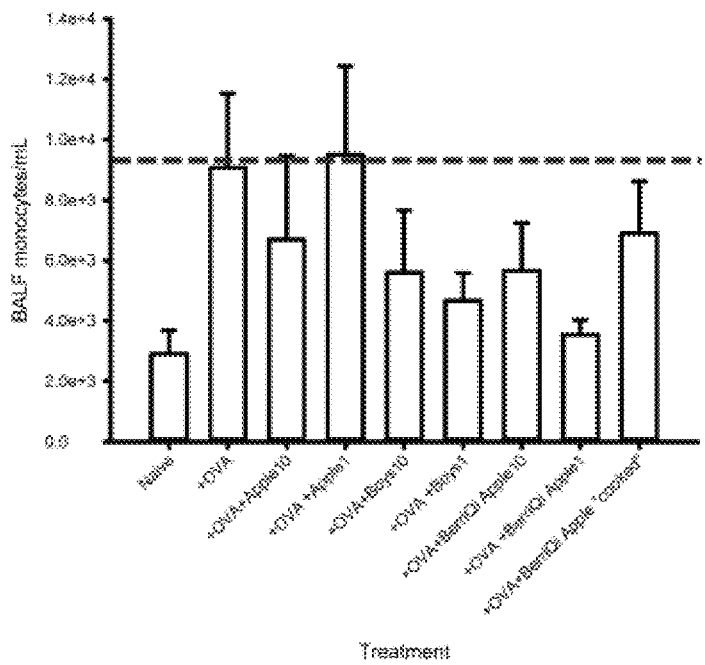
FIG. 15. Treatment utilising BerriQi™ Boysenberry with apple administration reduced monocyte numbers in model of acute allergic airways inflammation. Monocyte infiltration into the lung following an ovalbumin (OVA)-induced allergic airways infiltration. Total bronchioalveolar lavage fluid (BALF) monocyte cell numbers were determined 4 days post-OVA challenge (n=10 per intervention group).
Figure 16:
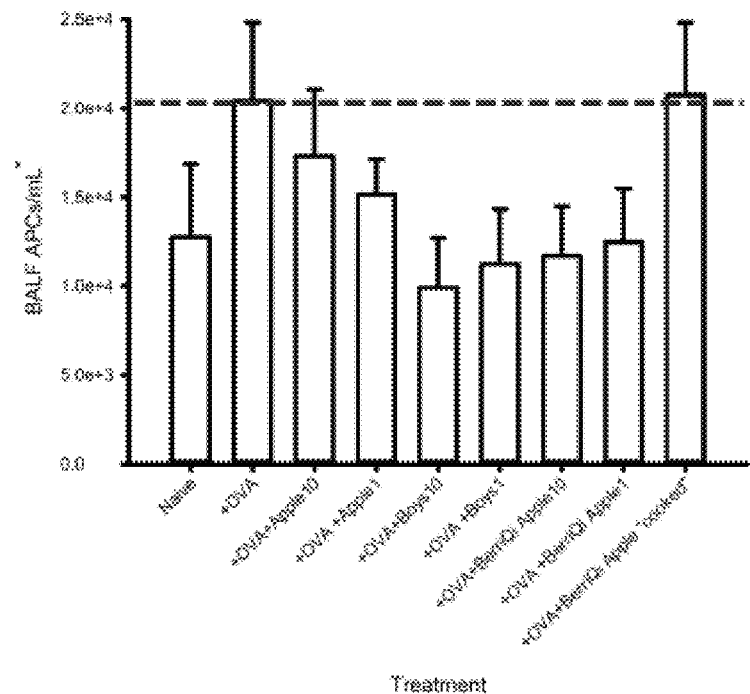
FIG. 16. Treatment utilising BerriQi™ Boysenberry with apple administration reduced antigen presenting cells in model of acute allergic airways inflammation. Antigen Presenting Cell (APC) infiltration into the lung following an ovalbumin (OVA)-induced allergic airways infiltration. Total bronchioalveolar lavage fluid (BALF) APC numbers were determined 4 days post-OVA challenge (n=10 per intervention group).
Figure 17:
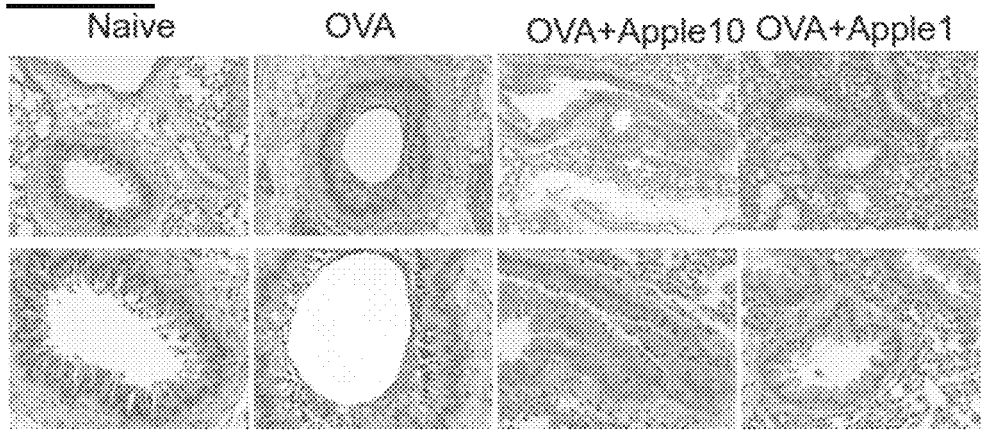
FIG. 17. Treatment utilising BerriQi™ Boysenberry with apple administration in model of acute allergic airways inflammation. Alcian blue/periodic acid Schiff diastase staining of lung tissues following apple treatment.

The results showed that apple treatment alone had little effect on eosinophil numbers, neutrophils, monocytes, or antigen presenting cells (APCs; FIGS. 10, 14-16). In contrast to this, combined BerriQi™ Boysenberry with apple treatment substantially reduced the number of eosinophils, neutrophils, and monocytes at low dosage levels (FIGS. 10, 14, 15). Heating the BerriQi™ Boysenberry with apple solution prior to treatment reversed this effect (FIGS. 10, 14, 15). Combined BerriQi™ Boysenberry with apple treatment also reduced the number of APCs (FIG. 16). Heating reversed this effect (FIG. 16).

Haematoxylin and eosin staining showed that the ovalbumin challenge resulted in tissue swelling and immune cell infiltration, while combined BerriQi™ Boysenberry with apple treatment appeared to reduce tissue swelling compared to OVA alone (FIGS. 13A-13H).

AB-PAS staining showed mucous production was variable between the different treatments (FIGS. 17, 18, and 19A-19H). None of the treatments made mucous production worse, although there were more mucous-producing cells observed in the lowest fruit concentrations, and none of the treatments appeared to prevent increased mucous production (FIGS. 17, 18, and 19A-19H). These results were attributed to the short duration and small number of administrations (two) for the acute experimental model. This contrasted to the longer experimental testing period and additional administrations noted in Example 1, noted above. It was proposed that effects on mucus production could be better observed given longer testing times and additional dosages.

Masson's trichrome staining showed that acute OVA challenge did not substantially increase fibrosis. There was not an increase in collagen deposition within the lung tissue (FIGS. 20, 21, and 22A-22H). The results from this histology indicated that the effect of treatments on fibrosis could not be tested in this acute experimental model. This confirmed that the short duration of the acute experimental model did not provide sufficient time to see effects for longer-term symptoms such as mucus production and collagen deposition.

Figure 23:
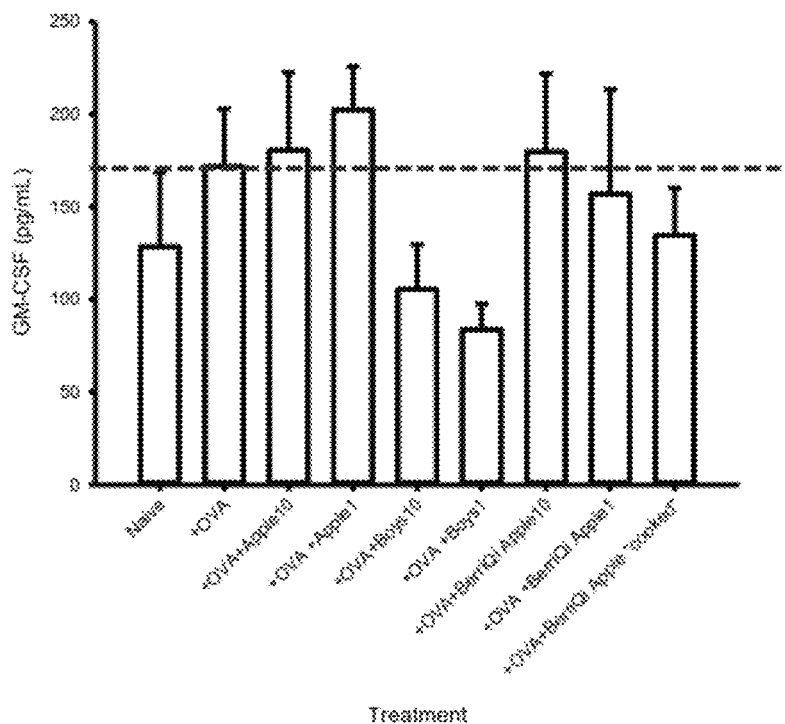
FIG. 23. Treatment utilising BerriQi™ Boysenberry with apple administration in model of acute allergic airways inflammation. Granulocyte-macrophage colony-stimulating factor levels following Boysenberry, apple, and BerriQi™ Boysenberry with apple treatments.
Figure 24:
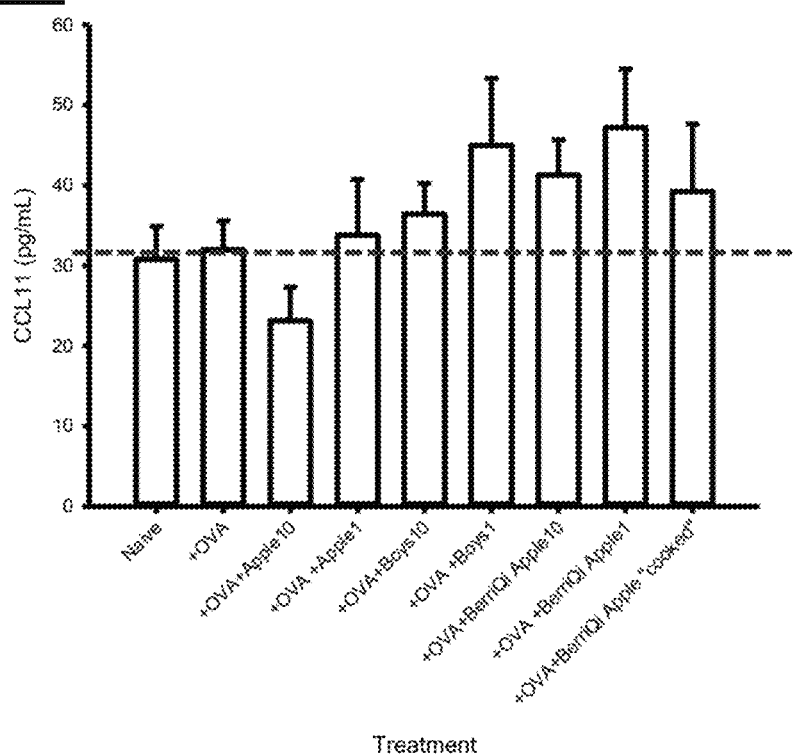
FIG. 24. Treatment utilising BerriQi™ Boysenberry with apple administration in model of acute allergic airways inflammation. CCL11 levels following Boysenberry, apple, and BerriQi™ Boysenberry with apple treatments.

Lung fluid obtained from test and control animals was assessed for cytokine levels, including granulocyte-macrophage colony-stimulating factor (GM-CSF), IFNγ, IFNβ, IL-1α, IL-1β, TNFα, IL-12(p40), IL-10, IL-6, IL-27, CXCL1, and CCL2. Boysenberry treatment alone reduced GM-CSF levels (FIG. 23), while apple treatment and combined BerriQi™ Boysenberry with apple treatment did not reduce GM-CSF levels (FIG. 23). CCL11 levels did not appear to be significantly affected (FIG. 24). IFNγ, IFNβ, IL-1α, IL-1β, TNFα, IL-12(p40), IL-10, IL-6, IL-27, CXCL1, and CCL2 were not detected in the samples tested (data not shown). Based on this, it was postulated that the effects of the BerriQi™ Boysenberry with apple treatment were not mediated by CCL11 secretion.

Discussion

From the results, it was concluded that combined BerriQi™ Boysenberry with apple treatment reduced the number of infiltrating eosinophils at both the standard and lower dosage levels. This effect was dependent on temperature-sensitive elements of the BerriQi™ Boysenberry with apple composition. Treatment using apple alone had little effect on numbers of neutrophils, monocytes, or APCs. Combined BerriQi™ Boysenberry with apple treatment reduced the number of neutrophils and monocytes at lower dosage levels, and reduced the number of APCs at standard and lower dosage levels. These effects were dependent on temperature-sensitive elements. It is clear, then, that combined administration of Boysenberry and apple compositions can be used to reduce numbers of immune cells associated with allergic airways inflammation.

The assessment of mucous production was variable between the different treatments, leading to the conclusion that additional or alternative measures of mucous suppression such as IL-13, IL-9 production may provide further clarity. Analysis of lung tissue supernatant to identify changes in proinflammatory cytokines showed that CCL11 levels were unaffected by BerriQi™ Boysenberry with apple treatment, suggesting that the decrease in eosinophils was not mediated via inhibition of CCL11. Additional analysis may be used to identify the particular agents that are involved in this process.

Overall, the results of this acute study were positive, showing that BerriQi™ Boysenberry with apple treatment reduced the cellular infiltration at both concentrations tested, whereas apple alone did not at either concentrations tested. Boysenberry alone also reduced cellular infiltration which was similar to what was found in the previous research described herein (see, e.g., Example 1 and (74)). Notably, the acute model of allergic-airways inflammation used in this study did not sufficiently promote the development of tissue fibrosis, so it could not be determined if BerriQi™ Boysenberry with apple treatment was able to promote the development of anti-fibrosis macrophages and prevent tissue damage. To determine the presence of such effects, it has been necessary to carry out further studies on chronic allergic-airways inflammation.

Example 3: OVA-Induced Chronic Airways Inflammation and Oral Treatment with Boysenberry and Apple Overview While consumption of certain fruits and vegetables has been studied in relation to beneficial health effects (87, 88, 91-94), the experiments described herein have been the first to show a substantial beneficial effect for specific Boysenberry compositions. See Example 1 and 2, and also (74). The key findings from the studies of Example 1 include: 1) Boysenberry consumption significantly reduced allergen-induced airways inflammation through decreased cell infiltration and increased anti-inflammatory protein production; 2) Boysenberry reduced collagen deposition and assisted in the repair of damaged tissue repair by supporting the development of fibrolytic macrophages, a type of immune cell; and 3) Boysenberry treatment prophylactically prevents ovalbumin (OVA)-induced airways inflammation.

The effect of different apple varieties on key cytokines for allergic airways disease has also been investigated (96), and cytokine inhibitory ability has been established for apple varieties in a cell culture model of allergic asthma induction. The inhibitory ability was correlated to the presence of the procyanidin polyphenols (96), and it has been shown that these compounds, in isolation, are potent inhibitors of key allergic chemokines CCL11 (90) and CCL26 (89). The aim of the current project was to evaluate BerriQi™ Boysenberry with apple treatment, a novel combination of Boysenberry and apple juice concentrates and water, in an animal model of chronic OVA-induced allergic airways inflammation.

Materials and Methodology

To perform this study, the previously established mouse model and an oral dosing strategy of chronic OVA-induced allergic airways inflammation was utilised as in Example 1 (see also, (52), (97)). Briefly, mice were primed with OVA/

Alum intraperitoneally (i.p.) and then challenged 7 days later with OVA intranasally (i.n.). These i.n. challenges were performed every week for 10 weeks. After 5 weeks of OVA challenges, the BerriQi™ interventions were begun. For these interventions, mice were fasted for 4 hours before being orally gavaged with water (disease and vehicle control), BerriQi™ Boysenberry with apple at 100%, 50% or 25%, at 2 days prior, at 1 hour prior to i.n. OVA challenge, and at 2 days post OVA challenge.

The intervention groups were: 1) Naïve (baseline control); 2) +OVA (disease and water vehicle control); 3) +OVA+BerriQi™ 100% (disease plus 100% BerriQi™ Boysenberry with apple) containing New Zealand sourced 70° Brix apple juice concentrate and New Zealand sourced 65° Brix Boysenberry juice concentrate; 4) +OVA+BerriQi™ 50% (disease plus 50% BerriQi™ Boysenberry with apple) containing New Zealand sourced 70° Brix apple juice concentrate and New Zealand sourced 65° Brix Boysenberry juice concentrate; and 5) +OVA+BerriQi™ 25% (disease plus 25% BerriQi™ Boysenberry with apple) containing New Zealand sourced 70° Brix apple juice concentrate and New Zealand sourced 65° Brix Boysenberry juice concentrate. The Boysenberry juice concentrate was obtained from Boysenberry NZ (Nelson, New Zealand). The apple juice concentrate was supplied by RD2 International (Auckland, New Zealand), and manufactured by Profruit (Hastings, New Zealand).

The concentration of Boysenberry in BerriQi™ Boysenberry with apple was calculated to deliver 0.73 mg/kg Boysenberry anthocyanins per serve for a 70 kg human, this being equivalent to 10 mg/kg in mouse. This dose was selected based on the previous studies (see Example 1 and (52)) that determined that consumption of 10 mg/kg Boysenberry anthocyanins resulted in reduced inflammation and tissue fibrosis in a mouse model of chronic allergic airways inflammation. 100% BerriQi™ Boysenberry with apple provided 10 mg/kg total Boysenberry anthocyanins for a 25 g mouse; 50% and 25% BerriQi™ Boysenberry with apple provided 5 mg/kg and 2.5 mg/kg total Boysenberry anthocyanins for a 25 g mouse, respectively. Details for the dosages are provided in Example 5, below.

Mice were euthanised 4 days following i.n. OVA challenge. The following parameters were measured as described in Example 1: 1) cellular infiltration: eosinophils, neutrophils, monocytes, and antigen presenting cells (APCs); 2) histological changes: haematoxylin and eosin (H&E), Alcian blue and periodic acid-Schiff (AB-PAS), Masson's trichrome staining; and 3) collagen production using the hydroxyproline assay. For the hydroxyproline assay, the commercial colorimetric kit was used (AbCam ab222941).

Results

Figure 25:
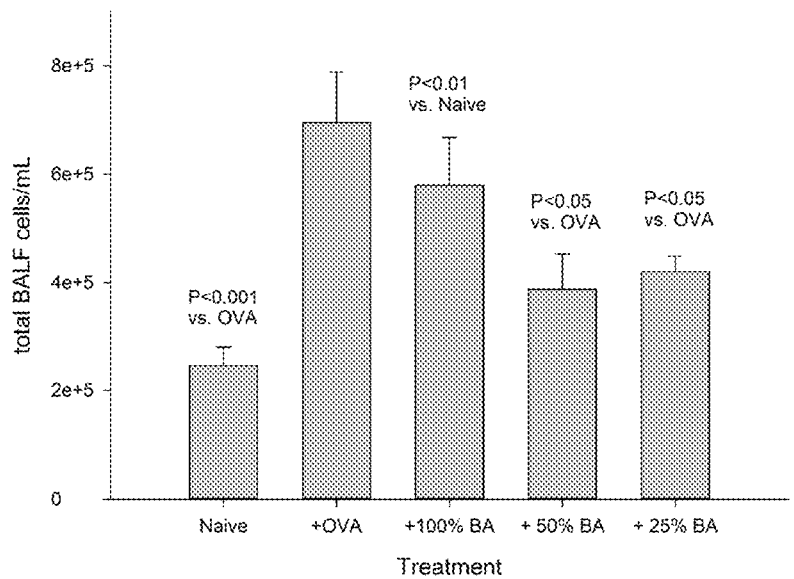
FIG. 25. Treatment utilising BerriQi™ Boysenberry with apple (BA) administration reduced immune cell numbers in model of chronic allergic airways inflammation. Total cell infiltration into the lung following chronic ovalbumin (OVA)-induced allergic airways infiltration. Total bronchioalveolar lavage fluid (BALF) cell numbers were determined 4 days following final OVA challenge. Data are mean±SEM (n=20 per intervention group). P<0.05, P<0.001 compared to OVA; P<0.01 compared to naïve.

The results showed an increased total immune cell infiltration into the lung in mice challenged i.n. with the allergen, OVA (FIG. 25). BerriQi™ Boysenberry with apple treatment significantly reduced the cellular infiltration at the 50% and 25% concentrations tested (FIG. 25). The 100% concentration BerriQi™ Boysenberry with apple treatment appeared to have no effect on the OVA-induced increase in immune cells in the lung. This was postulated as showing a therapeutic window for the BerriQi™ Boysenberry with apple treatment.

Figure 26:
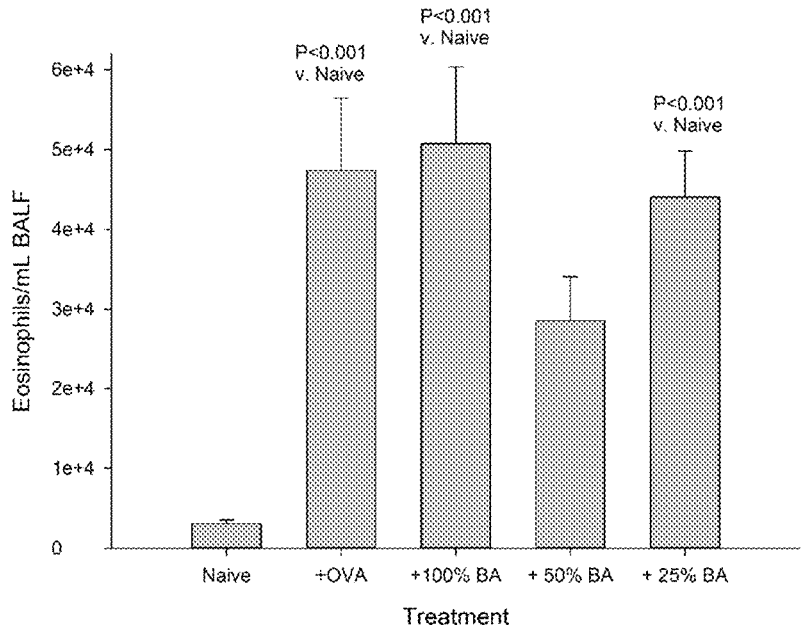
FIG. 26. Treatment utilising BerriQi™ Boysenberry with apple (BA) administration reduced eosinophil numbers in model of chronic allergic airways inflammation. Eosinophil infiltration into the lung following chronic ovalbumin (OVA)-induced allergic airways infiltration. Number of eosinophils in bronchioalveolar lavage fluid (BALF) cell was determined 4 days following final OVA challenge. Data are mean±SEM (n=20 per intervention group). P<0.001 compared to naïve.
Figure 27:
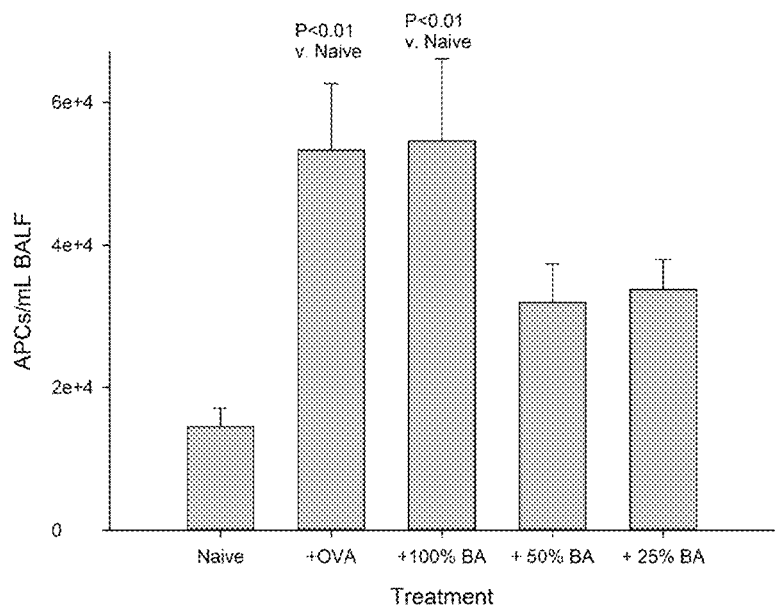
FIG. 27. Treatment utilising BerriQi™ Boysenberry with apple (BA) administration reduced antigen presenting cell numbers in model of chronic allergic airways inflammation. Antigen presenting cell (APC) infiltration into the lung following chronic ovalbumin (OVA)-induced allergic airways infiltration. Number of APCs in bronchioalveolar lavage fluid (BALF) cell was determined 4 days following final OVA challenge. Data are mean±SEM (n=20 per intervention group). P<0.01 compared to naïve.
Figure 28:
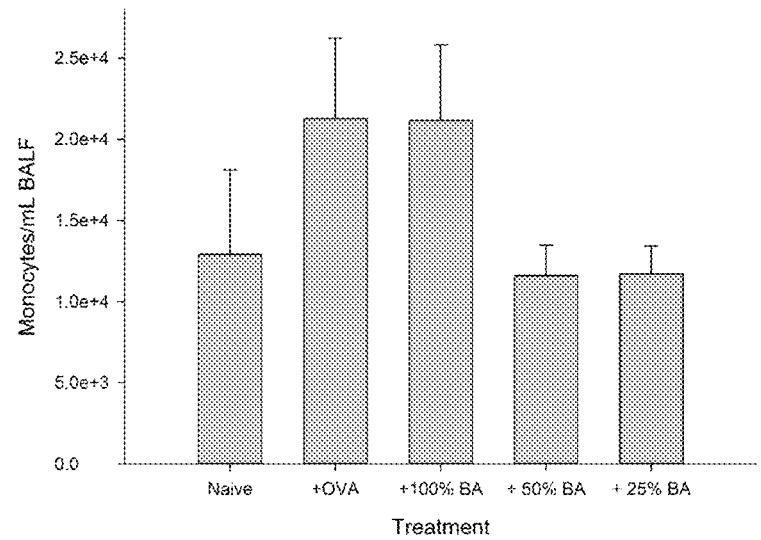
FIG. 28. Treatment utilising BerriQi™ Boysenberry with apple (BA) administration reduced monocyte numbers in model of chronic allergic airways inflammation. Monocyte infiltration into the lung following chronic ovalbumin (OVA)-induced allergic airways infiltration. Number of monocytes in bronchioalveolar lavage fluid (BALF) cell was determined 4 days following final OVA challenge. Data are mean±SEM (n=20 per intervention group).
Figure 29:
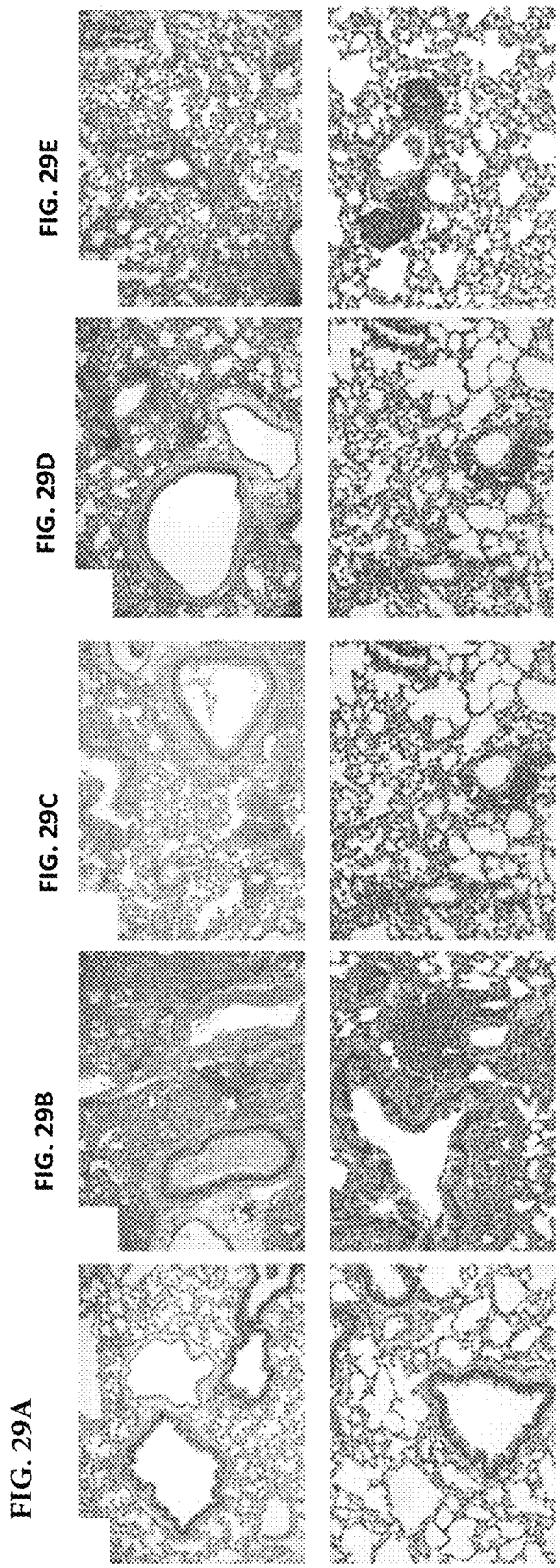
FIGS. 29A-29E. Treatment utilising BerriQi™ Boysenberry with apple (BA) administration in model of chronic allergic airways inflammation. Photomicrographs of lung tissue sections stained with haematoxylin and eosin staining following chronic ovalbumin (OVA)-induced allergic airways infiltration. Mice were primed with OVA/Alum intraperitoneally and then challenged 7 days later with OVA intranasally for 10 weeks. After 5 weeks mice were orally gavaged with nothing (FIG. 29A—naïve) water (FIG. 29B—OVA control) 100% (FIG. 29C) 50% (FIG. 29D) or 25% (FIG. 29E) BerriQi™ Boysenberry with apple 2 days prior, 1 hour before an OVA challenge and again 2 days post-challenge for 5 weeks.
Figure 30:
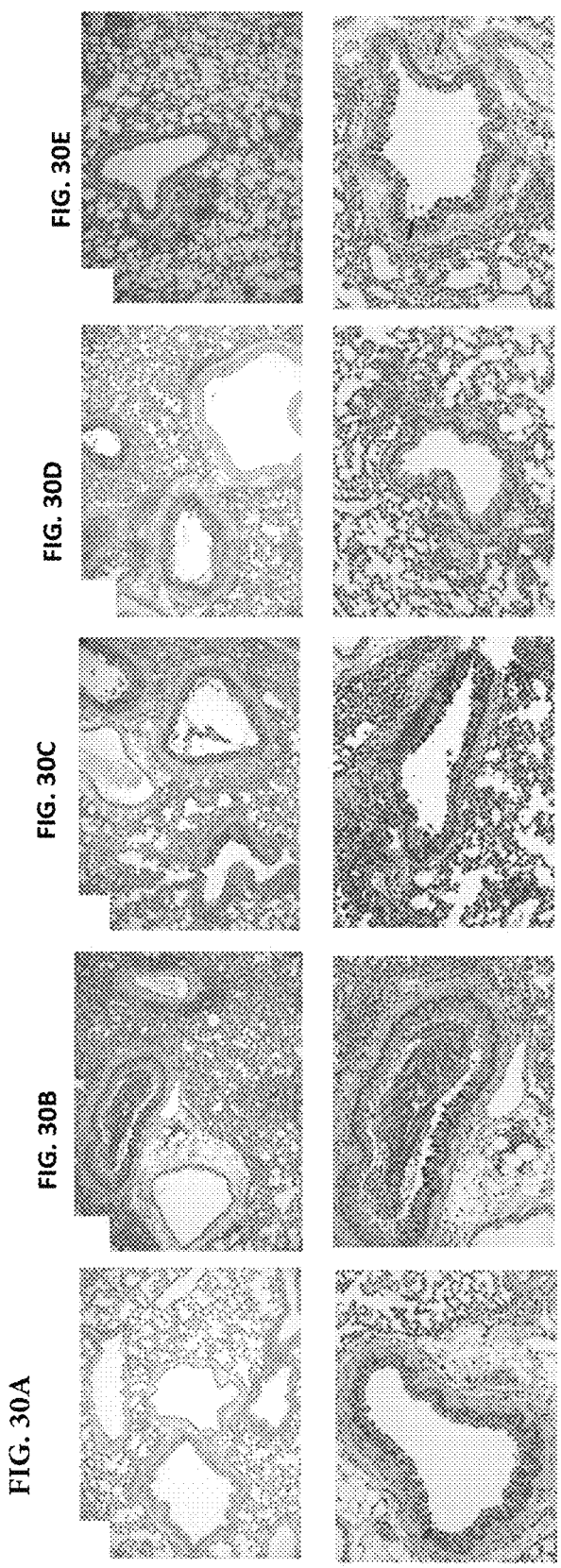
FIGS. 30A-30E. Treatment utilising BerriQi™ Boysenberry with apple (BA) administration in model of chronic allergic airways inflammation. Photomicrographs of lung tissue sections stained with Alcian blue and periodic acid-Schiff staining of lung tissue following chronic ovalbumin (OVA)-induced allergic airways infiltration. Mice were primed with OVA/Alum intraperitoneally and then challenged 7 days later with OVA intranasally for 10 weeks. After 5 weeks mice were orally gavaged with nothing (FIG. 30A—naïve) water (FIG. 30B—OVA control) 100% (FIG. 30C) 50% (FIG. 30D) or 25% (FIG. 30E) BerriQi™ Boysenberry with apple 2 days prior, 1 hour before an OVA challenge and again 2 days post-challenge for 5 weeks.
Figure 31:
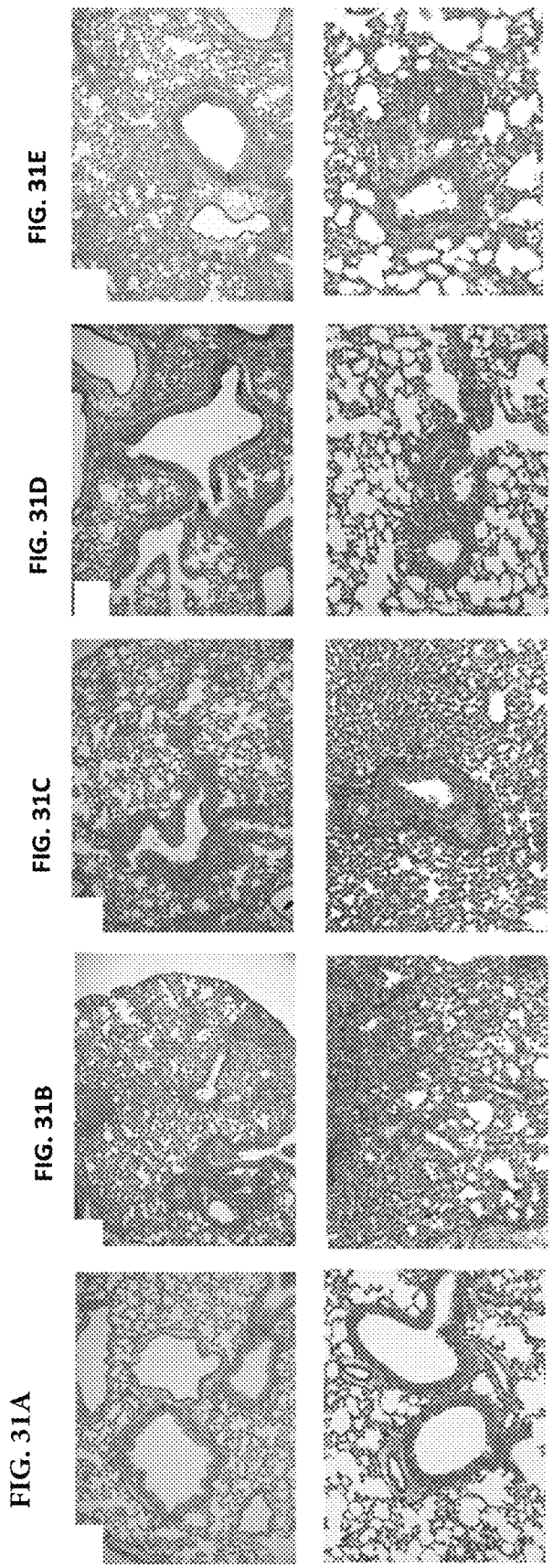
FIGS. 31A-31E. Treatment utilising BerriQi™ Boysenberry with apple (BA) administration in model of chronic allergic airways inflammation. Photomicrographs of lung tissue sections stained with Masson's Trichrome staining of lung tissue following chronic ovalbumin (OVA)-induced allergic airways infiltration. Mice were primed with OVA/Alum intraperitoneally and then challenged 7 days later with OVA intranasally for 10 weeks. After 5 weeks mice were orally gavaged with nothing (FIG. 31A—naïve) water (FIG. 31B—OVA control) 100% (FIG. 31C) 50% (FIG. 31D) or 25% (FIG. 31E) BerriQi™ Boysenberry with apple 2 days prior, 1 hour before an OVA challenge and again 2 days post-challenge for 5 weeks.

The immune cells were identified as eosinophils (FIG. 26), antigen presenting cells (FIG. 27), and monocytes (FIG. 28). The number of eosinophils showed a significant increase in mice challenged with OVA (FIG. 26). A decrease in eosinophil number was obtained by the 50% BerriQi™ Boysenberry and apple treatment (FIG. 26). Antigen presenting cells showed a significant increase with the OVA challenge, and a decrease in APC number was obtained by the 50% and the 25% BerriQi™ Boysenberry and apple treatment (FIG. 27). The number of monocytes was increased in mice challenged with OVA, and a decrease in monocyte number was obtained by the 50% and the 25% BerriQi™ Boysenberry and apple treatment (FIG. 28).

Haematoxylin and eosin staining showed that the ovalbumin challenge resulted in tissue swelling and confirmed the immune cell infiltration, and that this was decreased by BerriQi™ Boysenberry and apple treatment (FIGS. 29A-29E). AB-PAS staining showed that the ovalbumin challenge resulted in increased mucous production that was decreased in a dose-dependent manner by BerriQi™ Boysenberry and apple treatment (FIGS. 30A-30E).

Masson's trichrome staining showed that repeated OVA challenges resulted in diffuse blue staining of collagen fibres within the airways (FIGS. 31A-31E). BerriQi™ Boysenberry and apple treatment reduced the appearance of these blue collagen fibres within the lung (FIGS. 31A-31E).

Figure 32:
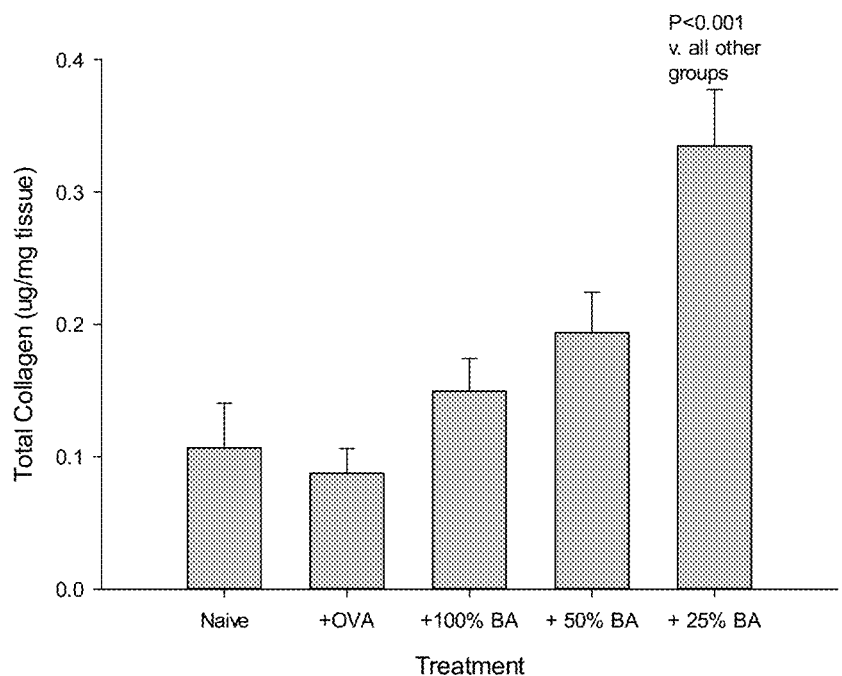
FIG. 32. Treatment utilising BerriQi™ Boysenberry with apple (BA) administration in model of chronic allergic airways inflammation. Quantification of collagen in the lung following chronic ovalbumin (OVA)-induced allergic airways infiltration. Mice were primed with OVA/Alum intraperitoneally and then challenged 7 days later with OVA intranasally for 10 weeks. After 5 weeks mice were orally gavaged with nothing (naïve), water (OVA control), 100%, 50%, or 25% BerriQi™ Boysenberry with apple (BA) 2 days prior, 1 hour before an OVA challenge and again 2 days post-challenge for 5 weeks. Collagen was determined using the hydroxyproline assay 4 days following the final OVA challenge. Data are mean±SEM (n=20 per intervention group). P<0.001 compared to all other treatment groups.

Quantification of collagen levels with the hydroxyproline assay showed no increase in collagen with OVA challenges (FIG. 32), which was contrary to previous results. No significant changes in collagen levels were seen with 100% or 50% BerriQi™ Boysenberry and apple treatment (FIG. 32). However, a significant increase in collagen levels was seen with 25% BerriQi™ Boysenberry and apple treatment (FIG. 32). This is discussed in more detail, below.

Discussion

The i.n. OVA challenge resulted in the appearance of increased inflammatory cells within the lung, which was reduced by 50% and 25% BerriQi™ Boysenberry with apple treatment. The 100% BerriQi™ Boysenberry with apple treatment had no effect on the number of infiltrating immune cells compared to the OVA challenged mice, indicating that there may be an optimal concentration for this treatment.

Mucous production was reduced by BerriQi™ Boysenberry with apple treatment in a dose-dependent manner, with the 25% BerriQi™ Boysenberry with apple treatment mediating the greatest reduction in mucous production.

Analysis of lung tissue to quantify the changes in total collagen showed that the quantity of collagen following OVA challenges was unchanged, which is inconsistent with the results from the original hydroxyproline assay (see, e.g., Example 1 and (74)). The assay used in this Example employed measurement reagents obtained from an alternate source as compared to the original assay.

Notably, Masson's trichrome staining indicated that OVA challenges resulted in collagen infiltrating into the airways, and BerriQi™ Boysenberry and apple treatment helped to reverse this infiltration. Thus, histological methods established that the location of the collagen around the tissues is altered by OVA, and this can be addressed by BerriQi™ Boysenberry and apple treatment.

Further research is needed to fully elucidate the meaning of the present hydroxyproline assay results. One possible explanation is the assay differences, as noted. In addition, it is possible that, although there was no change in the quantity of total collagen from OVA challenge, the location of the collagen has been altered, and this is being addressed by the BerriQi™ Boysenberry with apple and blackcurrant treatment. It is also possible that the increase in the amount collagen coupled with the reduction of collagen staining in the airways, as seen with the 25% BerriQi™ Boysenberry and apple treatment, is a result of tissue remodelling that occurs when the inflammation is being resolved.

Example 4: OVA-Induced Chronic Airways Inflammation and Oral Treatment with Boysenberry, Apple and Blackcurrant Materials and Methodology To perform this study, the mouse model and an oral dosing strategy of chronic OVA-induced allergic airways inflammation was utilised as in Example 1. See also, (52), (97). Briefly, mice were primed with OVA/Alum intraperitoneally (i.p) and then challenged 7 days later with OVA intranasally (i.n), this i.n challenge every week for 10 weeks. After 5 weeks of OVA challenges, the interventions were begun. For the interventions, mice were fasted for 4 hours before being orally gavaged with water (disease and vehicle control), or BerriQi™ Boysenberry with apple and blackcurrant at 100%, at 2 days prior, at 1 h prior to i.n. OVA challenge, and at 2 days post OVA challenge.

The intervention groups were: 1) Naïve (baseline control); 2) +OVA (disease and water vehicle control); 3) +OVA+BerriQi™ Boysenberry with apple and blackcurrant 100% (disease plus 100% BerriQi™ Boysenberry with apple and blackcurrant) containing New Zealand sourced 70 Brix apple juice concentrate, New Zealand sourced blackcurrant juice, and New Zealand sourced 65 Brix Boysenberry juice concentrate. The Boysenberry juice concentrate was obtained from Boysenberry NZ (Nelson, New Zealand). The apple juice concentrate was supplied by RD2 International (Auckland, New Zealand), and manufactured by Profruit (Hastings, New Zealand). The blackcurrant juice concentrate was obtained from New Zealand Blackcurrant Co-operative Ltd (Nelson, New Zealand).

The concentration of Boysenberry in BerriQi™ Boysenberry with apple and blackcurrant oral composition was calculated to deliver 0.73 mg/kg total anthocyanins per serve for a 70 kg human, this being equivalent to 10 mg/kg in mouse. This dose was selected based on the previous studies (see Example 1 and (52)) that determined that consumption of 10 mg/kg Boysenberry anthocyanins resulted in reduced inflammation and tissue fibrosis in a mouse model of chronic allergic airways inflammation. The 100% BerriQi™ Boysenberry with apple and blackcurrant oral composition provided 10 mg/kg total anthocyanins for a 25 g mouse. Details for the dosages are provided in Example 5, below.

Thus, in this study, it was tested whether a reduced concentration of Boysenberry anthocyanins could be utilised by supplementing the Boysenberry juice concentrate with an equal amount of blackcurrant juice concentrate to make the total concentration of anthocyanins to 10 mg/kg.

Mice were euthanized 4 days following i.n. OVA challenge. The following parameters were measured as described in Example 1: 1) cellular infiltration: eosinophils, monocytes and antigen presenting cells (APCs); 2) histological changes: haematoxylin and eosin (H&E), Alcian blue and periodic acid-Schiff (AB-PAS), and Masson's trichrome staining; and 3) collagen production using the hydroxyproline assay. For the hydroxyproline assay, the commercial colorimetric kit was used (AbCam ab222941).

Results

Figure 33:
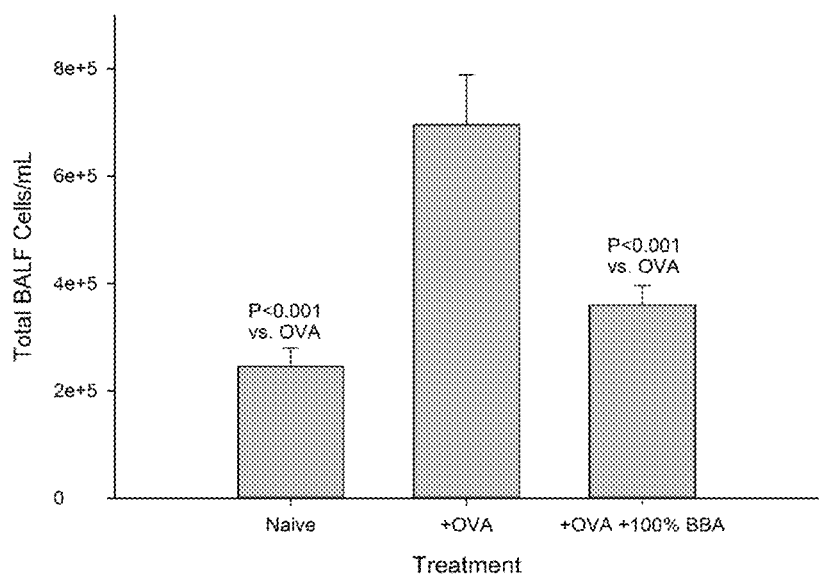
FIG. 33. Treatment utilising BerriQi™ Boysenberry with blackcurrant and apple (BBA) administration reduced immune cell numbers in model of chronic allergic airways inflammation. Total cell infiltration into the lung following chronic ovalbumin (OVA)-induced allergic airways infiltration. Total bronchioalveolar lavage fluid (BALF) cell numbers were determined 4 days following final OVA challenge (n=20 per intervention group).

The results showed increased total immune cell infiltration into the lung in mice challenged i.n. with the allergen, OVA (FIG. 33). BerriQi™ Boysenberry with apple and blackcurrant treatment significantly reduced the cellular infiltration at the concentrations tested (FIG. 33).

Figure 34:
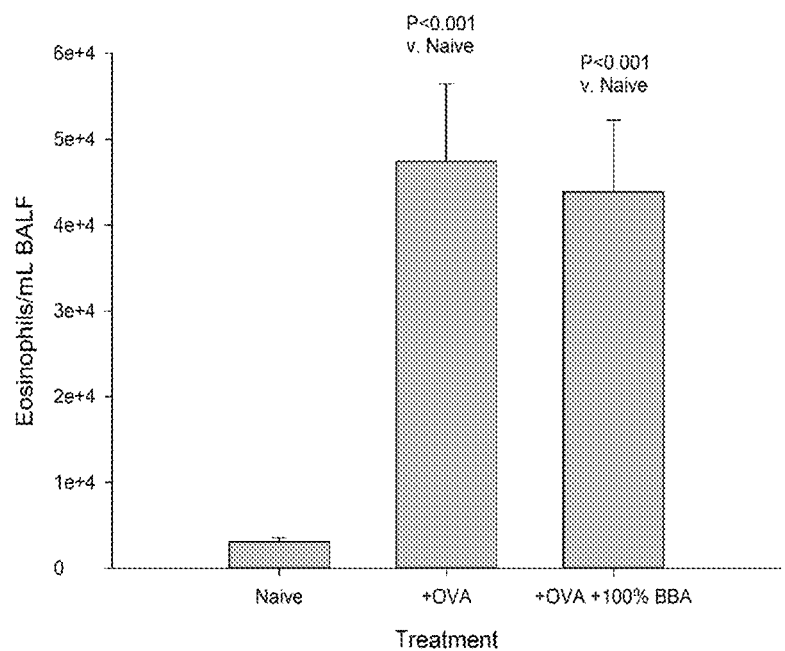
FIG. 34. Treatment utilising BerriQi™ Boysenberry with blackcurrant and apple (BBA) administration reduced eosinophil numbers in model of chronic allergic airways inflammation. Eosinophil infiltration into the lung following chronic ovalbumin (OVA)-induced allergic airways infiltration. Number of eosinophils in bronchioalveolar lavage fluid (BALF) cell was determined 4 days following final OVA challenge (n=20 per intervention group). P<0.001 compared to naïve.
Figure 35:
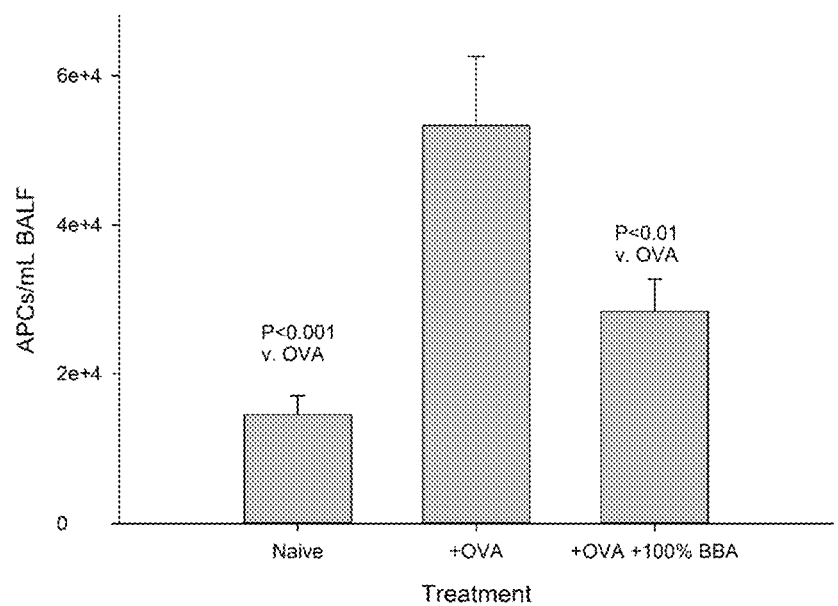
FIG. 35. Treatment utilising BerriQi™ Boysenberry with blackcurrant and apple (BBA) administration reduced antigen presenting cell numbers in model of chronic allergic airways inflammation. Antigen presenting cell (APC) infiltration into the lung following chronic ovalbumin (OVA)-induced allergic airways infiltration. Number of APCs in bronchioalveolar lavage fluid (BALF) cell was determined 4 days following final OVA challenge (n=20 per intervention group). P<0.001, P<0.01 compared to OVA.
Figure 36:
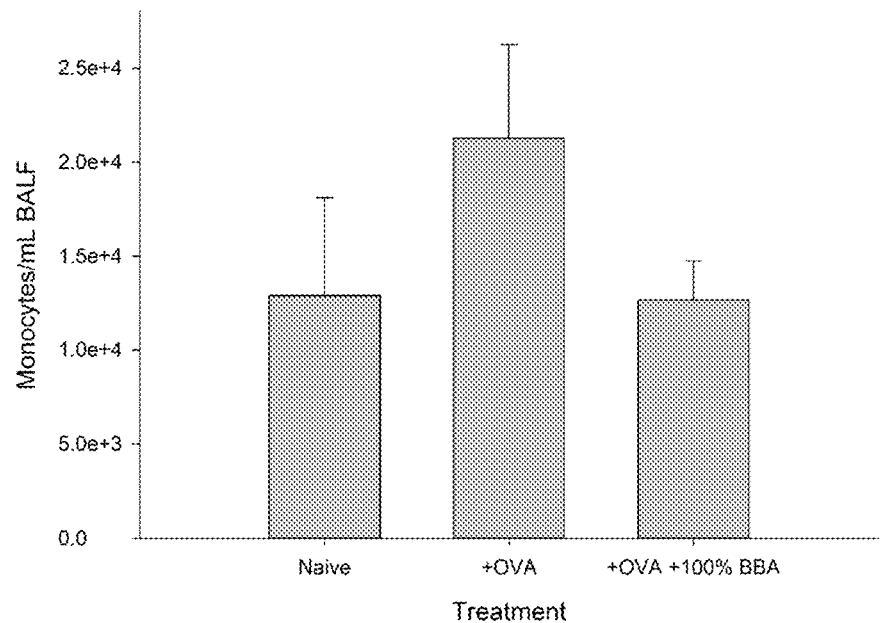
FIG. 36. Treatment utilising BerriQi™ Boysenberry with blackcurrant and apple (BBA) administration reduced monocyte numbers in model of chronic allergic airways inflammation. Monocyte infiltration into the lung following chronic ovalbumin (OVA)-induced allergic airways infiltration. Number of monocytes in bronchioalveolar lavage fluid (BALF) cell was determined 4 days following final OVA challenge (n=20 per intervention group).

The infiltrating cells were made up of eosinophils (FIG. 34), antigen presenting cells (FIG. 35), and monocytes (FIG. 36). The number of eosinophils was increased in mice challenged with OVA, but this increase was not affected by BerriQi™ Boysenberry with apple and blackcurrant treatment (FIG. 34). The number of antigen presenting cells was significantly increased by OVA challenge, and the APC number was significantly decreased by BerriQi™ Boysenberry with apple and blackcurrant treatment (FIG. 35). Monocytes trended towards increased numbers in mice challenged with OVA, and the monocyte numbers were decreased by BerriQi™ Boysenberry with apple and blackcurrant treatment (FIG. 36).

Figure 37:
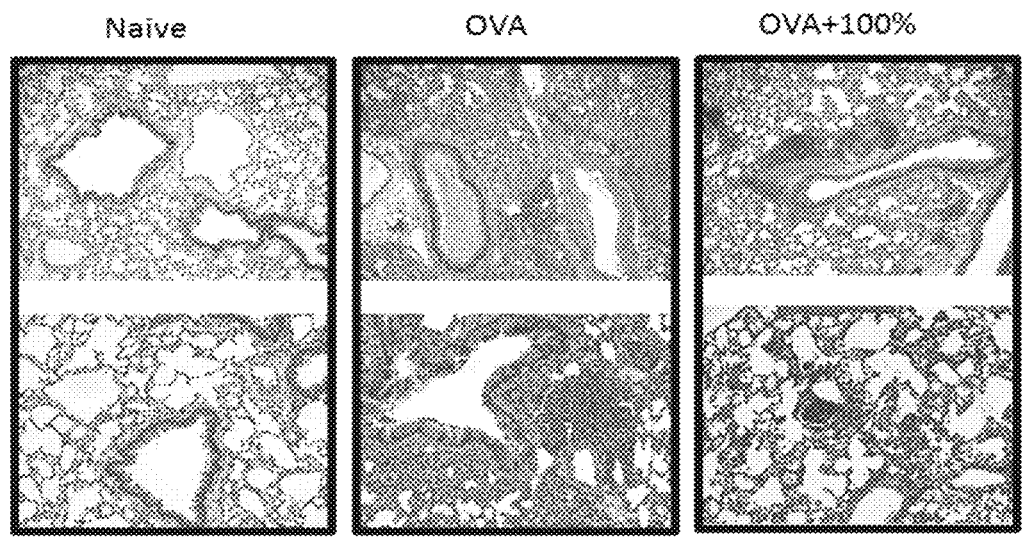
FIG. 37. Treatment utilising BerriQi™ Boysenberry with blackcurrant and apple (BBA) administration in model of chronic allergic airways inflammation. Haematoxylin and eosin staining of lung tissue following ovalbumin (OVA)-induced allergic airways infiltration. Mice were primed with OVA/Alum intraperitoneally and then challenged 7 days later with OVA intranasally for 10 weeks. After 5 weeks mice were orally gavaged with nothing (naïve) water (OVA control) or 100% BerriQi™ Boysenberry with apple and blackcurrant (OVA+100%) 2 days prior, 1 hour before an OVA challenge and again 2 days post-challenge for 5 weeks.
Figure 38:
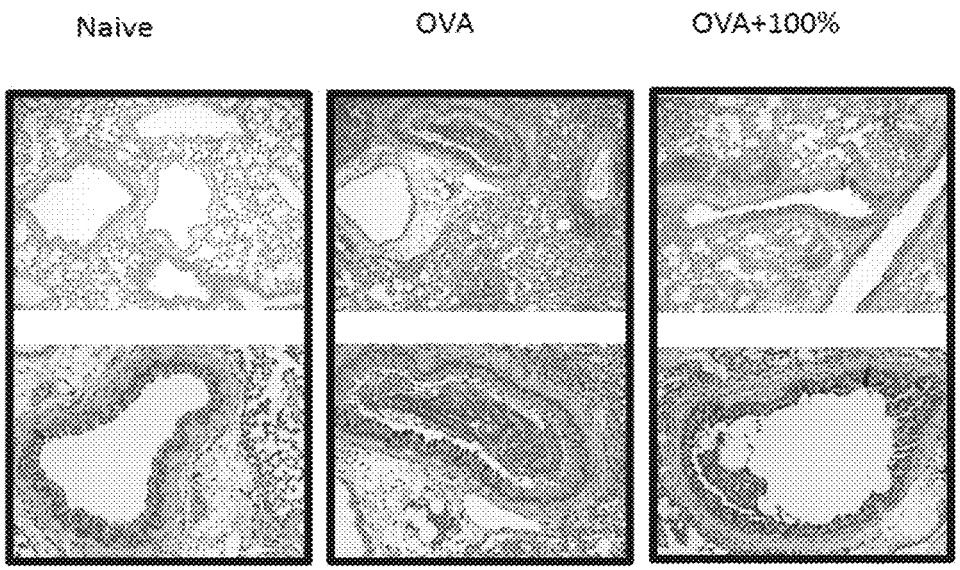
FIG. 38. Treatment utilising BerriQi™ Boysenberry with blackcurrant and apple (BBA) administration in model of chronic allergic airways inflammation. Alcian blue and periodic acid-Schiff staining of lung tissue following ovalbumin (OVA)-induced allergic airways infiltration. Mice were primed with OVA/Alum intraperitoneally and then challenged 7 days later with OVA intranasally for 10 weeks. After 5 weeks mice were orally gavaged with nothing (naïve) water (OVA control) or 100% BerriQi™ Boysenberry with apple and blackcurrant (OVA+100%) 2 days prior, 1 hour before an OVA challenge and again 2 days post-challenge for 5 weeks.

Haematoxylin and eosin staining showed that the ovalbumin challenge resulted in tissue swelling and immune cell infiltration, which was decreased by BerriQi™ Boysenberry with apple and blackcurrant treatment (FIG. 37). AB-PAS staining showed that the ovalbumin challenge resulted in increased mucous production that was unaffected by BerriQi™ Boysenberry with apple and blackcurrant treatment (FIG. 38).

Figure 39:
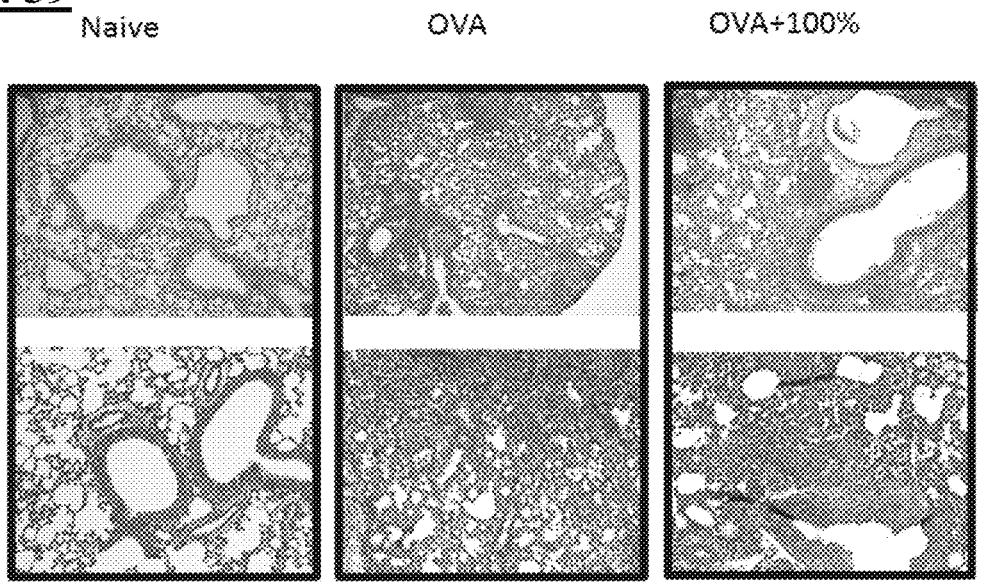
FIG. 39. Treatment utilising BerriQi™ Boysenberry with blackcurrant and apple (BBA) administration in model of chronic allergic airways inflammation. Masson's trichrome staining of lung tissue following ovalbumin (OVA)-induced allergic airways infiltration. Mice were primed with OVA/Alum intraperitoneally and then challenged 7 days later with OVA intranasally for 10 weeks. After 5 weeks mice were orally gavaged with nothing (naïve) water (OVA control) or 100% BerriQi™ Boysenberry with apple and blackcurrant (OVA+100%) 2 days prior, 1 hour before an OVA challenge and again 2 days post-challenge for 5 weeks.

Masson's trichrome staining showed that repeated OVA challenges resulted in diffuse blue staining of collagen fibres within the airways (FIG. 39). BerriQi™ Boysenberry with apple and blackcurrant treatment reduced the appearance of these blue collagen fibres within the lung (FIG. 39).

Figure 40:
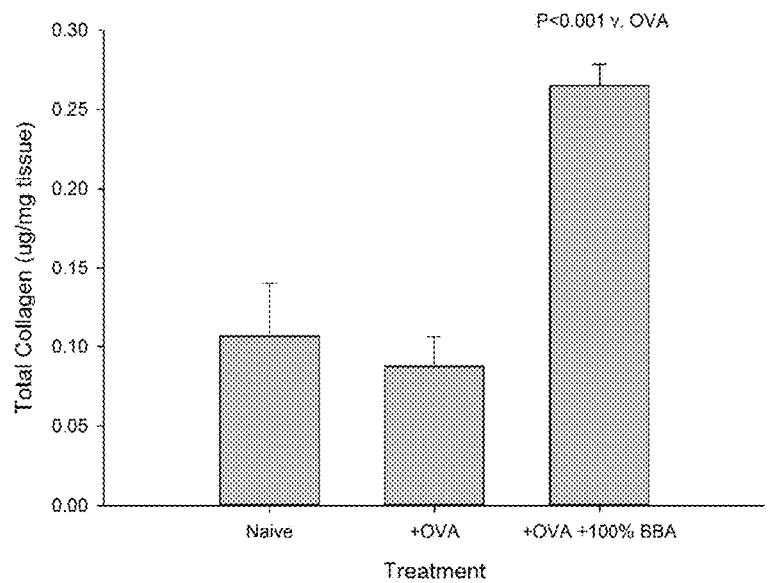
FIG. 40. Treatment utilising BerriQi™ Boysenberry with blackcurrant and apple (BBA) administration in model of chronic allergic airways inflammation. Quantification of collagen in the lung following ovalbumin (OVA)-induced allergic airways infiltration. Mice were primed with OVA/Alum intraperitoneally and then challenged 7 days later with OVA intranasally for 10 weeks. After 5 weeks mice were orally gavaged with 100% BerriQi™ Boysenberry with apple and blackcurrant (100% BBA) 2 days prior, 1 h before an OVA challenge and again 2 days post-challenge for 5 weeks. Collagen was determined using the hydroxyproline assay was determined 4 days post-OVA challenge (n=20 per intervention group).
Figure 41:
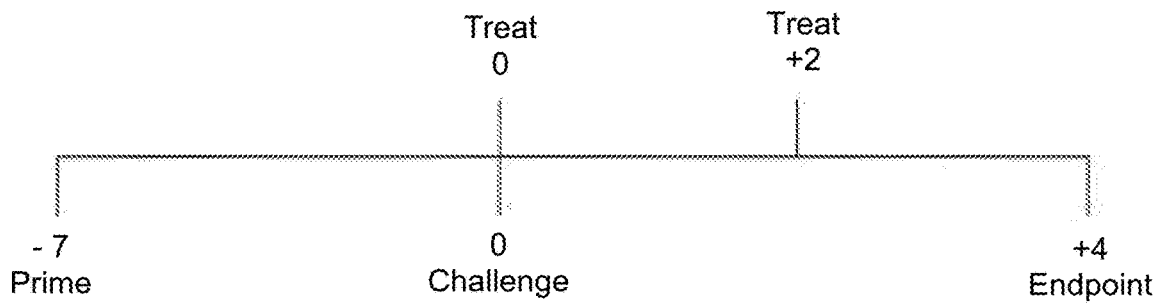
FIG. 41 is the dosing/challenge regimen for Example 2.

The hydroxyproline assay showed that there was no increase in total collagen with OVA challenges (FIG. 40), contrary to the original findings. In this assay, the 100% BerriQi™ Boysenberry with apple and blackcurrant treatment produced a significant increase in the quantity of collagen compared to the other groups (FIG. 40). This is discussed in more detail, below.

Discussion

The i.n. OVA challenge resulted in the appearance of increased inflammatory cells within the lung. The number of eosinophils in the lung were unaffected by BerriQi™ Boysenberry with apple and blackcurrant treatment, but the number of APCs was significantly decreased by BerriQi™ Boysenberry with apple and blackcurrant treatment. Monocytes trended towards an increase by OVA challenge and trended towards a decrease with BerriQi™ Boysenberry with apple and blackcurrant treatment.

Analysis of lung tissue to quantify the changes in collagen showed that the quantity of total collagen following OVA challenges was unchanged, which is inconsistent with the findings from the original assay (see, e.g., Example 1 and (74)). However, Masson's trichrome staining indicated that OVA challenges resulted in collagen infiltrating into the airways, which was counteracted by the 100% BerriQi™ Boysenberry with apple and blackcurrant treatment.

The differences in results for the hydroxyproline assays could be due to the differences in these assays, as already noted. In addition, it is possible that although there was no change in the quantity of total collagen from OVA challenge, the location of the collagen has been altered, and this is being addressed by the BerriQi™ Boysenberry with apple and blackcurrant treatment. It is also possible that the observations made for this this BerriQi™ Boysenberry with apple and blackcurrant treatment, including the increase in the amount collagen, coupled with the reduction of the appearance of collagen staining within the airways, is a result of tissue remodelling that occurs when inflammation is undergoing resolution.

Example 5: Dosage Calculations for Oral Treatments

The oral treatment dosages for Examples 3 and 4 were calculated in accordance with the following information.

TABLE 1

Dose calculations for chronic challenge mouse studies
Four treatment groups:

| | Sample and description | Dose rate in mice (mg/kg total anthocyanins TAC) | | Human Equivalent Dose * (mg/kg) |
|---|---|---|---|---|
| 1 | BerriQi ™ concentrate (1) | 100% | 10 † | 0.729 |
| 2 | (Boysenberry + Apple) | 50% | 5 | 0.364 |
| 3 | See Example 3 | 25% | 2.5 | 0.182 |
| 4 | BerriQi ™ concentrate (2) (Boysenberry + Blackcurrant + Apple) See Example 4 | 100% | 10 | 0.729 |

Dosing of $BerriQi^{TM}$ concentrate based on 200 µL for a 25 g mouse being equivalent for a 70 kg human
(in total anthocyanins)

†See Example 1 and (74)

*HED = animal dose in mg/kg ×

$$(\text{animal weight in kg/human weight in kg})^{0.33}$$

For example := 10 mg/kg mouse dose ×

$$(0.025 \text{ kg mouse/70 kg human})^{0.33}$$

= 0.73 mg/kg total anthocyanins for 70 kg human

TABLE 2

Starting concentrates and their composition

| Sample | Description | Composition |
|---|---|---|
| Sample (1) | BerriQi ™ Concentrate (1) (Boysenberry + Apple) | 27% Boysenberry juice concentrate 65 Brix (Boysenberries NZ Ltd); 72.88% Apple juice concentrate (clear) 70 Brix (RD2 International); 0.12% Potassium sorbate |
| Sample (2) | BerriQi ™ Concentrate (2) (Boysenberry + Blackcurrant + Apple) | 13.5% Boysenberry juice concentrate 65 Brix (Boysenberries NZ Ltd); 13.5% Blackcurrant juice concentrate 65 Brix (NZ Blackcurrant Co-op); 72.88% Apple juice concentrate (clear) 70 Brix (RD2 International); 0.12% Potassium sorbate |

TABLE 3

Calculations for anthocyanin concentrations

| Sample | Description | Total anthocyanins (as cyanidin-3-glucoside) | Calculation |
|---|---|---|---|
| Sample (1) | BerriQi ™ Concentrate (1) (Boysenberry + Apple) | 145 mg/100 g juice concentrate | Specific gravity = 1.34 g/ml 1 g juice concentrate = 0.746 ml 1 ml juice concentrate = 1.34 g Therefore: 1,450 µg/g (1.45 mg/g) or 1,943 µg/ml juice concentrate |
| Sample (2) | BerriQi ™ Concentrate (2) (Boysenberry + Blackcurrant + Apple) | 236 mg/100 g juice concentrate | Specific gravity = 1.34 g/ml 1 g juice concentrate = 0.746 ml 1 ml juice concentrate = 1.34 g Therefore: 2,360 µg/g (2.36 mg/g) or 3,162 µg/ml juice concentrate |

TABLE 4

Dosage calculations based on anthocyanin concentrations

| Sample | Description | Dose rate in mice (mg/kg total anthocyanins TAC) | | Volume of BerriQi ™ Concentrate required in 200 µL dose (µL) |
|---|---|---|---|---|
| 1 | BerriQi ™ | 100% | 10 | 129 |
| 2 | Concentrate (1) | 50% | 5 | Serial dilution |
| 3 | (Boysenberry + Apple) | 25% | 2.5 | Serial dilution |
| 4 | BerriQi ™ Concentrate (2) (Boysenberry + Blackcurrant + Apple) | 100% | 10 | 79 |

Detailed calculations for dosages in Table 1 for BerriQi™ concentrate (1) at 100% as utilised in Example 3 (Boysenberry with apple):

Calculation to Determine Mouse Dosage

Desire a dose of 10 mg anthocyanin/kg for a 25 g mouse (Example 1 and (74)) —100%

A 10 mg anthocyanin/kg dose for a 25 g mouse would require 0.25 mg of anthocyanin Therefore: 0.172 g $BerriQi^{TM} conc$ (1) required to deliver a 0.25 mg dose of anthocyanin = 0.29 mL $BerriQi^{TM} conc$ (1) required to deliver a 0.25 mg dose anthocyanin = 128.667 µL $BerriQi^{TM} conc$ (1) required to deliver a 0.25 mg dose anthocyanin $Sp$ Gravity 1.34 g/ml Preparation of Oral Composition for Mouse Trial Take 128.667 µL BerriQi™ conc (1) and make it up to 200 µL with $H_2O$ There is now 0.25 mg of anthocyanin in 200 µL mouse dose, 10 mg/kg for a 25 g mouse Detailed calculations for dosages in Table 1 for BerriQi™ concentrate (2) at 100% as utilised in Example 4 (Boysenberry with apple and blackcurrant):

Calculation to Determine Mouse Dosage

Desire a dose of 10 mg anthocyanin/kg for a 25 g mouse (Example 1 and (74)) —100%
A 10 mg anthocyanin/kg dose for a 25 g mouse would require 0.25 mg of anthocyanin Therefore: 0.106 g $BerriQi^{TM}conc$ (2) required to deliver a 0.25 mg dose of anthocyanin = 0.079 mL $BerriQi^{TM}conc$ (2) required to deliver a 0.25 mg dose of anthocyanin = 79.054 µL $BerriQi^{TM}conc$ (2) required to deliver a 0.25 mg dose of anthocyanin Sp Gravity 1.340 g/ml Preparation of Oral Composition for Mouse Trial Take 79.054 µL BerriQi™ conc (2) and make it up to 200 µL with $H_2O$
There is now 0.25 mg of anthocyanin in 200 µL mouse dose, 10 mg/kg for a 25 g mouse
Alternative dosage calculation details for BerriQi™ concentrate (1) (Boysenberry+Apple):
Mouse weight 25 g
Dose (total anthocyanins) 10 mg/kg (or 0.1 mg/10 g)
Therefore: dose=0.25 mg per mouse
BerriQi™ (Boysenberry+Apple) total anthocyanins 145 mg/100 g (or 1.45 mg/g)
Weight product needed 0.25 mg/1.45 mg=0.172 g BerriQi™
Able to do weight of product in water because specific gravity is known
Specific Gravity 1.34 kg/L (or 1.34 g/mL)
Volume needed 0.172 g/1.34 g=0.128.66 mL
This equates to 129 µL per mouse plus 71 µL water (200 µl minus 129 µl)

Example 6: Compositional Analysis of Treatment Formulations

BerriQi™ liquid formulations were subjected to chemical analysis to determine anthocyanin and phenolic composition. The formulations tested included: Sample 1, BerriQi™ with apple concentrate 1 (BB+AP); Sample 2, BerriQi™ with apple plus blackcurrant concentrate 2 (BB+BC+AP). See Example 5. Weighed aliquots of the samples were diluted 5-fold with 10% formic $acid_{aq}$ for analysis by ultra high pressure liquid chromatography (UHPLC). For analysis of other phenolics by liquid chromatography mass spectrometry (LC-MS), samples were diluted 10-fold with 0.1% formic $acid_{aq}$. Sample density was determined and samples taken for dry matter calculations.

UHPLC analysis of anthocyanins: Anthocyanin concentrations were measured using a Dionex UltiMate 3000 Series UHPLC (ThermoFisher Scientific, San Jose, CA, USA) with PDA (photodiode array) detection at 520 nm. Compound separation was achieved using a Synergi 4µ hydro-RP 80A column, 4.6×250 mm (Phenomenex, Torrance, CA, USA), maintained at 40° C. Solvents were (A) 5:5:90 acetonitrile:formic acid:water v/v/v and (B) 5:95 v/v formic acid:acetonitrile and the flow rate was 1 mL/min. The initial mobile phase, 100% A was held for 1 min, then ramped linearly to 84% A in 16 min, followed by a column flush at 5% A before resetting to the original conditions. The sample injection volume was 0.5 µL. Detected anthocyanins were quantified by UHPLC using a pure standard of cyanidin 3-O-glucoside and all the results for individual and total anthocyanins are expressed as cyanidin 3-O-glucoside equivalents.

LC-MS confirmation: LC-MS employed an LTQ linear ion trap mass spectrometer fitted with an ESI interface (ThermoFisher Scientific, San Jose, CA, USA) coupled to an Ultimate 3000 UHPLC and PDA detector (Dionex, Sunnyvale, CA, USA).

Anthocyanin confirmation: Anthocyanin compound separation was achieved using a Poroshell 120 SB-C18 column, 2.7µ 2.1×150 mm (Agilent, Torrance, CA, USA), maintained at 70° C. Solvents were (A) 5:3:92 acetonitrile:formic acid:water v/v/v and (B) acetonitrile+0.1% formic acid, and the flow rate was 200 µL/min. The initial mobile phase, 100% A was held for 2 min before being ramped linearly to 88% A at 14 min, 5% A at 15 min and held for 4 min before resetting to the original conditions. The sample injection volume was 10 µL. MS data were acquired in the positive mode using a data-dependent LC-$MS^3$ method. This method isolates and fragments the most intense parent ion to give $MS^2$ data (daughter ions), then isolates and fragments the most intense daughter ion ($MS^3$ data).

Other phenolics: Other phenolic compound separation was achieved using a Hypersil GOLD aQ 1.9µ, C18 175 Å (Thermo Scientific, Waltham, Massachusetts USA), 150×2.1 mm column maintained at 45° C. Solvents were (A) water+0.1% formic acid and (B) acetonitrile+0.1% formic acid, and the flow rate was 200 µl/min. The initial mobile phase, 95% A/5% B, was ramped linearly to 85% A at 10 min, held for 3.75 min, then ramped linearly to 75% A at 18 min, 67.2% A at 25 min, 50% A at 28 min, 3% A at 29 min and held for 4 min before resetting to the original conditions. The sample injection volume was 4 µL. UV-vis detection was by absorbance at 200-600 nm. MS data were acquired in both negative and positive modes with ESI ionisation using three data-dependent LC-$MS^3$ methods, the first using mass range [m/z 150-900] optimised for detection of low molecular weight phenolic compounds, the second using mass range [m/z 150-2000] optimised for detection of ellagitannins and the third using mass range [m/z 150-4000] optimised for detection of higher molecular weight soluble tannins. MS data were also acquired in both negative and positive modes with APCI ionisation.

Phenolic acids, gallic acid, protocatechuric acid, chlorogenic acid (3-caffeoylquinic acid), caffeic acid were quantified by LC-MS using pure standards of these compounds. Detected derivatives of coumaric acid were quantified by LC-MS using p-coumaric acid, and are expressed as p-coumaric acid equivalents. The flavan-3-ols, epi-catechin and catechin, and procyanidin B2, were quantified by LC-MS using pure standards of these compounds. Unknowns m/z 563 and m/z 579 were quantified by LC-MS using epi-catechin, and expressed as epi-catechin equivalents. Hydrolysable tannins were quantified by LC-MS using a standard of Sanguiin H6 that had been isolated previously (>98% purity by LC-MS). Other detected tannins and unknown m/z 639 were quantified by LC-MS as Sanguiin H6 equivalents. Ellagic acid was quantified by LC-MS using a standard of ellagic acid. Detected flavonol glycosides were quantified by LC-MS using a pure standard of quercetin 3-O-glucoside and are expressed as quercetin 3-O-glucoside equivalents. The non-glycosylated flavanols, quercetin and myricetin, and the chalcones, phloretin and phloretin-2-O-glucoside were quantified by LC-MS using pure standards of these compounds. The preservative sorbic acid was quantified by LC-MS using a pure standard of this compound.

The results for the analysis are shown as follows.

TABLE 5

Density and dry matter data for BerriQi™ samples

| Sample | Description | Density (g/mL) | Dry Matter (%) |
|---|---|---|---|
| 1 | BerriQi™ concentrate (1) BB + AP | 1.346 | 70.24 |
| 2 | BerriQi™ concentrate (2) BB + BC + AP | 1.351 | 71.37 |

TABLE 6

Quantitation summary for detected phenolics in BerriQi™ samples 1 and 2 expressed in μg/mL and μg/g dry weight (DW)

| Compound | Sample 1 μg/mL | Sample 1 μg/g DW | Sample 2 μg/mL | Sample 2 μg/g DW |
|---|---|---|---|---|
| Anthocyanins | | | | |
| Delphinidin 3-O-glucoside | nd | nd | 120 | 125 |
| Cyanidin 3-O-sophoroside | 925 | 978 | 306 | 317 |
| Delphinidin 3-O-rutinoside | nd | nd | 868 | 900 |
| Cyanidin 3-O-glucoside | 597 | 631 | 248 | 258 |
| Cyanidin 3-O-sambubioside | 26 | 28 | 8 | 8 |
| Cyanidin 3-O-(2-glucosylrutinoside) | 431 | 456 | 146 | 152 |
| Cyanidin 3-O-rutinoside | 69 | 73 | 913 | 947 |
| Cyanidin 3-O-xylosylrutinoside | 18 | 19 | 5 | 5 |
| Phenolic acids | | | | |
| Gallic acid | 162 | 171 | 33 | 35 |
| Protocatechuric acid | 41 | 43 | 17 | 18 |
| Chlorogenic acid | 74 | 78 | 60 | 63 |
| Caffeic acid | 6 | 6 | 6 | 6 |
| 4-p-Coumaroylquinic acid | 20 | 21 | 33 | 35 |
| 5-p-Coumaroylquinic acid | 3 | 3 | 8 | 9 |
| Flavan-3-ols and procyanidins | | | | |
| Procyanidin B2 | 5 | 5 | 6 | 7 |
| Catechin | 3 | 3 | 5 | 5 |
| Epi-catechin | 17 | 18 | 11 | 12 |
| Hydrolysable tannins | | | | |
| Sanguiin H10 isomer 1 | 13 | 13 | 6 | 7 |
| Sangui sorbic acid dilactone | 234 | 248 | 5 | 52 |
| Galloyl-SH6 | 79 | 84 | 24 | 25 |
| Sanguiin H10 isomer 2 | 79 | 84 | 44 | 45 |
| Lambertian C (minus ellagic acid) | 13 | 14 | 9 | 9 |
| Lambertian C | 27 | 29 | 9 | 10 |
| Sanguiin H6 | 257 | 271 | 99 | 103 |
| Ellagic acid | 626 | 662 | 96 | 100 |
| Flavanols | | | | |
| Quercetin 3-O-rutinoside | 8 | 8 | 62 | 64 |
| Quercetin 3-O-galactoside | 18 | 19 | 26 | 27 |
| Quercetin 3-O-glucuronide | 42 | 45 | 3 | 3 |
| Quercetin 3-O-glucoside | 13 | 14 | 36 | 37 |
| Quercetin 3-O-pentoside 1 | 9 | 10 | 12 | 12 |
| Quercetin 3-O-pentoside 2 | 11 | 12 | 14 | 15 |
| Quercetin 3-O-pentoside 3 | 6 | 7 | 3 | 4 |
| Quercetin 3-O-rhamnoside | 14 | 13 | 15 | 13 |
| Quercetin | 33 | 35 | 37 | 38 |

TABLE 6-continued

Quantitation summary for detected phenolics in BerriQi™ samples 1 and 2 expressed in μg/mL and μg/g dry weight (DW)

| Compound | Sample 1 μg/mL | Sample 1 μg/g DW | Sample 2 μg/mL | Sample 2 μg/g DW |
|---|---|---|---|---|
| Myricetin-3-O-rutinoside | nd | nd | 81 | 84 |
| Myricetin-3-O-glucoside | nd | nd | 33 | 35 |
| Myricetin-malonylglucoside | nd | nd | 4 | 4 |
| Myricetin | nd | nd | 7 | 7 |
| Aureusidin-glucoside | nd | nd | 3 | 3 |
| Kaempferol-3-O-rutinoside | nd | nd | 8 | 8 |
| Kaempferol-3-O-glucoside | nd | nd | 5 | 5 |
| Chalcones | | | | |
| Phloretin 2-O-xylo-glucoside | 10 | 11 | 9 | 10 |
| Phloretin 2-O-glucoside | 76 | 80 | 95 | 99 |
| Unknowns | | | | |
| Unknown m/z 563# | 10 | 11 | 4 | 4 |
| Unknown m/z 639 | 65 | 69 | 54 | 56 |
| Unknown m/z 579 | 3 | 3 | 3 | 3 |
| Totals | 4043 | 4275 | 3645 | 3784 | nd = not detected
= detected as [M + formate]-adduct

Persons of ordinary skill can utilise the disclosures and teachings herein to produce other embodiments and variations without undue experimentation. All such embodiments and variations are considered to be part of this invention.

Accordingly, one of ordinary skill in the art will readily appreciate from the disclosure that later modifications, substitutions, and/or variations performing substantially the same function or achieving substantially the same result as embodiments described herein may be utilised according to such related embodiments of the present invention. Thus, the invention is intended to encompass, within its scope, the modifications, substitutions, and variations to processes, manufactures, compositions of matter, compounds, means, methods, and/or steps disclosed herein.

The description herein may contain subject matter that falls outside of the scope of the claimed invention. This subject matter is included to aid understanding of the invention.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

REFERENCES

1. Atkinson J J, Lutey B A, Suzuki Y, Toennies H M, Kelley D G, Kobayashi D K, Ijem W G, Deslee G, Moore C H, Jacobs M E, Conradi S H, Gierada D S, Pierce R A, Betsuyaku T, Senior R M. The role of matrix metalloproteinase-9 in cigarette smoke-induced emphysema. Am J Respir Crit Care Med 183: 876-884, 2011.
2. Beamer C A, Migliaccio C T, Jessop F, Trapkus M, Yuan D, Holian A. Innate immune processes are sufficient for driving silicosis in mice. J Leukoc Biol 88: 547-557, 2010.
3. Belleguic C, Corbel M, Germain N, Lena H, Boichot E, Delaval P H, Lagente V. Increased release of matrix metalloproteinase-9 in the plasma of acute severe asthmatic patients. Clin Exp Allergy 32: 217-223, 2002.
4. Byers D E, Holtzman M J. Alternatively activated macrophages and airway disease. Chest 140: 768-774, 2011.
5. Cabrera S, Gaxiola M, Arreola J L, Ramirez R, Jara P, D'Armiento J, Richards T, Selman M, Pardo A. Overexpression of MMP9 in macrophages attenuates pulmonary fibrosis induced by bleomycin. Int J Biochem Cell Biol 39: 2324-2338, 2007.
6. Cataldo D D, Bettiol J, Noel A, Bartsch P, Foidart J M, Louis R. Matrix metalloproteinase-9, but not tissue inhibitor of matrix metalloproteinase-1, increases in the sputum from allergic asthmatic patients after allergen challenge. Chest 122: 1553-1559, 2002.
7. Cho J Y, Miller M, McElwain K, McElwain S, Shim J Y, Raz E, Broide D H. Remodeling associated expression of matrix metalloproteinase 9 but not tissue inhibitor of metalloproteinase 1 in airway epithelium: modulation by immunostimulatory DNA. J Allergy Clin Immunol 117: 618-625, 2006.
8. Corbel M, Belleguic C, Boichot E, Lagente V. Involvement of gelatinases (MMP-2 and MMP-9) in the development of airway inflammation and pulmonary fibrosis. Cell Biol Toxicol 18: 51-61, 2002.
9. Dasgupta P, Keegan A D. Contribution of alternatively activated macrophages to allergic lung inflammation: a tale of mice and men. J Innate Immun 4: 478-488, 2012.
10. Fireman E, Kraiem Z, Sade O, Greif J, Fireman Z. Induced sputum-retrieved matrix metalloproteinase 9 and tissue metalloproteinase inhibitor 1 in granulomatous diseases. Clin Exp Immunol 130: 331-337, 2002.
11. Forastiere F, Pistelli R, Sestini P, Fortes C, Renzoni E, Rusconi F, Dell'Orco V, Ciccone G, Bisanti L. Consumption of fresh fruit rich in vitamin C and wheezing symptoms in children. SIDRIA Collaborative Group, Italy (Italian Studies on Respiratory Disorders in Children and the Environment). Thorax 55: 283-288, 2000.
12. Fujita H, Aoki H, Ajioka I, Yamazaki M, Abe M, Oh-Nishi A, Sakimura K, Sugihara I. Detailed expression pattern of aldolase C (Aldoc) in the cerebellum, retina and other areas of the CNS studied in Aldoc-Venus knock-in mice. PLoS One 9: e86679, 2014.
13. Garcia V, Arts I C, Sterne J A, Thompson R L, Shaheen S O. Dietary intake of flavonoids and asthma in adults. Eur Respir J 26: 449-452, 2005.
14. Gibbons M A, MacKinnon A C, Ramachandran P, Dhaliwal K, Duffin R, Phythian-Adams A T, van Rooijen N, Haslett C, Howie S E, Simpson A J, Hirani N, Gauldie J, Iredale J P, Sethi T, Forbes S J. Ly6Chi monocytes direct alternatively activated profibrotic macrophage regulation of lung fibrosis. Am J Respir Crit Care Med 184: 569-581, 2011.
15. Greenlee K J, Corry D B, Engler D A, Matsunami R K, Tessier P, Cook R G, Werb Z, Kheradmand F. Proteomic identification of in vivo substrates for matrix metalloproteinases 2 and 9 reveals a mechanism for resolution of inflammation. J Immunol 177: 7312-7321, 2006.
16. Jang H Y, Kim S M, Yuk J E, Kwon O K, Oh S R, Lee H K, Jeong H, Ahn K S. Capsicum annuum L. methanolic extract inhibits ovalbumin-induced airway inflammation and oxidative stress in a mouse model of asthma. J Med Food 14: 1144-1151, 2011.
17. Kang H R, Cho S J, Lee C G, Homer R J, Elias J A. Transforming growth factor (TGF)-beta1 stimulates pulmonary fibrosis and inflammation via a Bax-dependent, bid-activated pathway that involves matrix metalloproteinase-12. J Biol Chem 282: 7723-7732, 2007.
18. Kaviratne M, Hesse M, Leusink M, Cheever A W, Davies S J, McKerrow J H, Wakefield L M, Letterio J J, Wynn T A. IL-13 activates a mechanism of tissue fibrosis that is completely TGF-beta independent. J Immunol 173:4020-4029, 2004.
19. Kim S H, Kim B K, Lee Y C. Effects of Corni fructus on ovalbum-induced airway inflammation and airway hyper-responsiveness in a mouse model of allergic asthma. J Inflamm (Lond) 9: 9, 2012.
20. Kobayashi T, Kim H, Liu X, Sugiura H, Kohyama T, Fang Q, Wen F Q, Abe S, Wang X, Atkinson J J, Shipley J M, Senior R M, Rennard S I. Matrix metalloproteinase-9 activates TGF-beta and stimulates fibroblast contraction of collagen gels. Am J Physiol Lung Cell Mol Physiol 306: L1006-L1015, 2014.
21. Lagente V, Manoury B, Nenan S, Le Quement C, Martin-Chouly C, Boichot E. Role of matrix metalloproteinases in the development of airway inflammation and remodeling. Braz J Med Biol Res 38: 1521-1530, 2005.
22. Lee C G, Homer R J, Zhu Z, Lanone S, Wang X, Koteliansky V, Shipley J M, Gotwals P, Noble P, Chen Q, Senior R M, Elias J A. Interleukin-13 induces tissue fibrosis by selectively stimulating and activating transforming growth factor beta(1). J Exp Med 194: 809-821, 2001.
23. Lee Y C, Lee H B, Rhee Y K, Song C H. The involvement of matrix metalloproteinase-9 in airway inflammation of patients with acute asthma. Clin Exp Allergy 31: 1623-1630, 2001.
24. Lim D H, Cho J Y, Miller M, McElwain K, McElwain S, Broide D H. Reduced peribronchial fibrosis in allergen-challenged MMP-9-deficient mice. Am J Physiol Lung Cell Mol Physiol 291: L265-L271, 2006.
25. Lukkarinen H, Hogmalm A, Lappalainen U, Bry K. Matrix metalloproteinase-9 deficiency worsens lung injury in a model of bronchopulmonary dysplasia. Am J Respir Cell Mol Biol 41: 59-68, 2009.
26. Maarsingh H, Dekkers B G, Zuidhof A B, Bos I S, Menzen M H, Klein T, Flik G, Zaagsma J, Meurs H. Increased arginase activity contributes to airway remodelling in chronic allergic asthma. Eur Respir J 38:318-328, 2011.
27. Maarsingh H, Zaagsma J, Meurs H. Arginase: a key enzyme in the pathophysiology of allergic asthma opening novel therapeutic perspectives. Br J Pharmacol 158: 652-664, 2009.
28. Manoury B, Caulet-Maugendre S, Guenon I, Lagente V, Boichot E. TIMP-1 is a key factor of fibrogenic response to bleomycin in mouse lung. Int J Immunopathol Pharmacol 19: 471-487, 2006.
29. Martinez F O, Helming L, Gordon S. Alternative activation of macrophages: an immunologic functional perspective. Annu Rev Immunol 27:451-483, 2009.
30. Mauad T, Bel E H, Sterk P J. Asthma therapy and airway remodeling. J Allergy Clin Immunol 120: 997-1009; quiz 1010-1001, 2007.
31. McKinstry S U, Karadeniz Y B, Worthington A K, Hayrapetyan V Y, Ozlu M I, Serafin-Molina K, Risher W C, Ustunkaya T, Dragatsis I, Zeitlin S, Yin H H, Eroglu C. Huntingtin is required for normal excitatory synapse development in cortical and striatal circuits. J Neurosci 34:9455-9472, 2014.
32. McMillan S J, Kearley J, Campbell J D, Zhu X W, Larbi K Y, Shipley J M, Senior R M, Nourshargh S, Lloyd C M. Matrix metalloproteinase-9 deficiency results in enhanced allergen-induced airway inflammation. J Immunol 172: 2586-2594, 2004.

33. Mehra D, Sternberg D I, Jia Y, Canfield S, Lemaitre V, Nkyimbeng T, Wilder J, Sonett J, D'Armiento J. Altered lymphocyte trafficking and diminished airway reactivity in transgenic mice expressing human MMP-9 in a mouse model of asthma. Am J Physiol Lung Cell Mol Physiol 298:L189-L196, 2010.

34. Meurs H, Maarsingh H, Zaagsma J. Arginase and asthma: novel insights into nitric oxide homeostasis and airway hyperresponsiveness. Trends Pharmacol Sci 24: 450-455, 2003.

35. Mori M, Gotoh T. Regulation of nitric oxide production by arginine metabolic enzymes. Biochem Biophys Res Commun 275: 715-719, 2000.

36. Nair M G, Du Y, Perrigoue J G, Zaph C, Taylor J J, Goldschmidt M, Swain G P, Yancopoulos G D, Valenzuela D M, Murphy A, Karow M, Stevens S, Pearce E J, Artis D. Alternatively activated macrophage-derived RELM-α is a negative regulator of type 2 inflammation in the lung. J Exp Med 206: 937-952, 2009.

37. Nieuwenhuizen N E, Kirstein F, Jayakumar J, Emedi B, Hurdayal R, Horsnell W G, Lopata A L, Brombacher F. Allergic airway disease is unaffected by the absence of IL-4R alpha-dependent alternatively activated macrophages. J Allergy Clin Immunol 130: 743-750.e8, 2012.

38. Ohbayashi H, Shimokata K. Matrix metalloproteinase-9 and airway remodeling in asthma. Curr Drug Targets Inflamm Allergy 4: 177-181, 2005.

39. Okoko B J, Burney P G, Newson R B, Potts J F, Shaheen S O. Childhood asthma and fruit consumption. Eur Respir J 29: 1161-1168, 2007.

40. Park S J, Shin W H, Seo J W, Kim E J. Anthocyanins inhibit airway inflammation and hyperresponsiveness in a murine asthma model. Food Chem Toxicol 45: 1459-1467, 2007.

41. Pera T, Zuidhof A B, Smit M, Menzen M H, Klein T, Flik G, Zaagsma J, Meurs H, Maarsingh H. Arginase inhibition prevents inflammation and remodeling in a guinea pig model of chronic obstructive pulmonary disease. J Pharmacol Exp Ther 349: 229-238, 2014.

42. Pesce J T, Ramalingam T R, Mentink-Kane M M, Wilson M S, El Kasmi K C, Smith A M, Thompson R W, Cheever A W, Murray P J, Wynn T A. Arginase-1-expressing macrophages suppress Th2 cytokine-driven inflammation and fibrosis. PLoS Pathog 5: e1000371, 2009.

43. Peters S P. Asthma treatment in the 21st century: what's next? Clin Rev Allergy Immunol 27: 197-205, 2004.

44. Priceman S J, Sung J L, Shaposhnik Z, Burton J B, Torres-Collado A X, Moughon D L, Johnson M, Lusis A J, Cohen D A, Iruela-Arispe M L, Wu L. Targeting distinct tumor-infiltrating myeloid cells by inhibiting CSF-1 receptor: combating tumor evasion of antiangiogenic therapy. Blood 115: 1461-1471, 2010.

45. Roche W R, Beasley R, Williams J H, Holgate S T. Subepithelial fibrosis in the bronchi of asthmatics. Lancet 1: 520-524, 1989.

46. Romieu I, Varraso R, Avenel V, Leynaert B, Kauffmann F, Clavel-Chapelon F. Fruit and vegetable intakes and asthma in the E3N study. Thorax 61: 209-215, 2006.

47. Rosenlund H, Kull I, Pershagen G, Wolk A, Wickman M, Bergstrom A. Fruit and vegetable consumption in relation to allergy: disease-related modification of consumption? J Allergy Clin Immunol 127: 1219-1225, 2011.

48. Rosenlund H, Magnusson J, Kull I, Hakansson N, Wolk A, Pershagen G, Wickman M, Bergstrom A. Antioxidant intake and allergic disease in children. Clin Exp Allergy 42: 1491-1500, 2012.

49. Russell R E, Culpitt S V, DeMatos C, Donnelly L, Smith M, Wiggins J, Barnes P J. Release and activity of matrix metalloproteinase-9 and tissue inhibitor of metalloproteinase-1 by alveolar macrophages from patients with chronic obstructive pulmonary disease. Am J Respir Cell Mol Biol 26: 602-609, 2002.

50. Schneider C A, Rasband W S, Eliceiri K W. NIH Image to ImageJ: 25 years of image analysis. Nat Methods 9: 671-675, 2012.

51. Shaheen S O, Sterne J A, Thompson R L, Songhurst C E, Margetts B M, Burney P G. Dietary antioxidants and asthma in adults: population-based case-control study. Am J Respir Crit Care Med 164: 1823-1828, 2001.

52. Shaw O M, Harper J L. An efficient single prime protocol for the induction of antigen-induced airways inflammation. J Immunol Methods 395: 79-82, 2013.

53. Sin Y Y, Ballantyne L L, Mukherjee K, St Amand T, Kyriakopoulou L, Schulze A, Funk C D. Inducible arginase 1 deficiency in mice leads to hyperargininemia and altered amino acid metabolism. PLoS One 8:e80001, 2013.

54. Todorova L, Gurcan E, Westergren-Thorsson G, Miller-Larsson A. Budesonide/formoterol effects on metalloproteolytic balance in TGFbeta-activated human lung fibroblasts. Respir Med 103: 1755-1763, 2009.

55. Urso M L, Wang R, Zambraski E J, Liang B T. Adenosine A3 receptor stimulation reduces muscle injury following physical trauma and is associated with alterations in the MMP/TIMP response. J Appl Physiol 112: 658-670, 2012.

56. Van Bruaene N, Derycke L, Perez-Novo C A, Gevaert P, Holtappels G, De Ruyck N, Cuvelier C, Van Cauwenberge P, Bachert C. TGF-beta signaling and collagen deposition in chronic rhinosinusitis. J Allergy Clin Immunol 124: 253-259, 259.e1-e2, 2009.

57. van den Hengel L G, Hellingman A A, Nossent A Y, van Oeveren-Rietdijk A M, de Vries M R, Spek C A, van Zonneveld A J, Reitsma P H, Hamming J F, de Boer H C, Versteeg H H, Quax P H. Protease-activated receptor (PAR)2, but not PAR1, is involved in collateral formation and anti-inflammatory monocyte polarization in a mouse hind limb ischemia model. PLoS One 8: e61923, 2013.

58. Van Rooijen N, Sanders A. Liposome mediated depletion of macrophages: mechanism of action, preparation of liposomes and applications. J Immunol Methods 174: 83-93, 1994.

59. Vignola A M, Kips J, Bousquet J. Tissue remodeling as a feature of persistent asthma. J Allergy Clin Immunol 105: 1041-1053, 2000.

60. Weidenbusch M, Anders H J. Tissue microenvironments define and get reinforced by macrophage phenotypes in homeostasis or during inflammation, repair and fibrosis. J Innate Immun 4: 463-477, 2012.

61. WHO. Prevention of Allergy and Allergic Asthma: Based on the WHO/WAO Meeting on the Prevention of Allergy and Allergic Asthma, Geneva, 8-9 Jan. 2002. Geneva: World Health Organization, 2003.

62. Woods R K, Walters E H, Raven J M, Wolfe R, Ireland P D, Thien F C K, Abramson M J. Food and nutrient intakes and asthma risk in young adults. Am J Clin Nutr 78: 414-421, 2003.

63. Wu G, Morris S M Jr. Arginine metabolism: nitric oxide and beyond. Biochem J 336: 1-17, 1998.

64. Wu K, Koo J, Jiang X, Chen R, Cohen S N, Nathan C. Improved control of tuberculosis and activation of macrophages in mice lacking protein kinase R. PLoS One 7: e30512, 2012.

65. Yoon H K, Cho H Y, Kleeberger S R. Protective role of matrix metalloproteinase-9 in ozone-induced airway inflammation. Environ Health Perspect 115: 1557-1563, 2007.
66. Zimmermann N, Rothenberg M E. The arginine-arginase balance in asthma and lung inflammation. Eur J Pharmacol 533: 253-262, 2006.
67. Lieberman P L, Oppenheimer J, Desai M, 2015, Allergic Remodelling, World Allergy Organisation, article published online at: http://www.worldallergy.org/professional/allergic_diseases_center/allergic_remodeling/68.
68. Holgate S T, Holloway J, Wilson S, Bucchieri F, Puddicombe S, Davies D E. Epithelial-mesenchymal communication in the pathogenesis of chronic asthma. Proc Am Thorac Soc. 1(2):93-98, 2004.
69. Chakir J, Shannon J, Molet S, et al. Airway remodeling-associated mediators in moderate to severe asthma: effect of steroids on TGF-beta, IL-11, IL-17, and type I and type III collagen expression. J Allergy Clin Immunol. 111(6): 1293-1298, 2003.
70. The Childhood Asthma Management Program Research Group. Long-term effects of budesonide or nedocromil in children with asthma. N Engl J Med. 343(15):1054-1063, 2000.
71. Busse W W, Pedersen S, Pauwels R A, et al. The Inhaled Steroid Treatment As Regular Therapy in Early Asthma (START) study 5-year follow-up: effectiveness of early intervention with budesonide in mild persistent asthma. J Allergy Clin Immunol. 121(5):1167-1174, 2008.
72. Covar R A, Spahn J D, Murphy J R, Szefler S J, Group CAMPR. Progression of asthma measured by lung function in the childhood asthma management program. Am J Respir Crit Care Med. 170(3):234-241, 2004.
73. Guilbert T W, Morgan W J, Zeiger R S, et al. Long-term inhaled corticosteroids in preschool children at high risk for asthma. N Engl J Med. 354(19):1985-1997, 2006.
74. Shaw O M, Hurst R D, Harper J L, Boysenberry ingestion supports fibrolytic macrophages with the capacity to ameliorate chronic lung remodelling, Am J Physiol Lung Cell Mol Physiol 311: L628-L638, 2016.
75. Singleton, Vernon L, Orthofer, Rudolf, Lamuela-Raventós, Rosa M. Analysis of total phenols and other oxidation substrates and antioxidants by means of Folin-Ciocalteu reagent 299: 152, 1999.
76. Lister C E, Lancaster J E, Sutton K H, Walker J R L. Development changes in the concentration and composition of flavonoids in skin of a red and a green apple cultivar. Journal of the Science of Food and Agriculture 64: 155-161, 1994.
77. Cao G, Alessio H, Cutler R. Oxygen-radical absorbance capacity assay for antioxidants. Free Radical Biology and Medicine 14 (3): 303-311, 1993.
78. Ou B, Hampsch-Woodill M, Prior R. Development and validation of an improved oxygen radical absorbance capacity assay using fluorescein as the fluorescent probe. Journal of Agricultural and Food Chemistry 49 (10): 4619-4626, 2001.
79. Brand-Williams W, Cuvelier M E, Berset C. Use of a free radical method to evaluate antioxidant activity. Lebensm. Wiss. Tecnol. 28: 25-30, 1995.
80. Sanchez-Moreno C, Larraui J A, Saura-Calixto F. A procedure to measure the antiradical efficiency of polyphenols. Journal of Science and the Food of Agriculture 76: 270-276, 1998.
81. Sun-Waterhouse D, Wen I, Wibisono R, Melton L D, Wadhwa S. Evaluation of the extraction efficiency for polyphenol extracts from by-products of green kiwifruit juicing. International Journal of Food Science & Technology. 44(12): 2644-2652, 2009.
82. Eidenberger T, Selg M, Fuerst S, Krennhuber K. In-vitro inhibition of human lipase PS by polyphenols from kiwi fruit. Journal of Food Research. 3(4): 71-77, 2014.
83. Athar N, McLaughlin J, Taylor G. The concise New Zealand food composition tables. 6th edition. New Zealand Institute for Crop & Food Research/Ministry of Health: Palmerston North, New Zealand. 177 p, 2003.
84. Wada L, Ou B. Antioxidant activity and phenolic content of Oregon caneberries. Journal of Agricultural and Food Chemistry 50: 3495-3500, 2002.
85. Lister C E, Andrews F M, Ganeshan D. Comparison of Chilean and New Zealand boysenberry fruit and concentrates, Crop & Food Research Report No. 2059, 2008.
86. Terzikhan N, et al. Prevalence and incidence of COPD in smokers and non-smokers: the Rotterdam Study Eur J Epidemiol 31:785-792, 2016.
87. Bakolis I, Hooper R, Thompson R L, Shaheen S O. Dietary patterns and adult asthma: population-based case-control study, Allergy 65(5): 606-15, 2010.
88. Butland B K, Fehily A M, Elwood P C. Diet, lung function, and lung function decline in a cohort of 2512 middle aged men, Thorax 55(2): 102-8, 2000.
89. Coleman S, Kruger M, Sawyer G, Hurst R. Procyanidin A2 Modulates IL-4-Induced CCL26 Production in Human Alveolar Epithelial Cells, Int J Mol Sci 17(11): 1888, 2016.
90. Coleman S L, Hurst R D, Sawyer G M, Kruger M C. The in vitro evaluation of isolated procyanidins as modulators of cytokine-induced eotaxin production in human alveolar epithelial cells, J Berry Res 6(2): 115-124, 2016.
91. Gilliland F D. Children's Lung Function and Antioxidant Vitamin, Fruit, Juice, and Vegetable Intake, American Journal of Epidemiology 158(6): 576-584, 2003.
92. Hurst R D, Hurst S M. Fruits and Vegetables as Functional Foods for Exercise and Inflammation, In: Watson R R and Preedy V R, Eds., Bioactive Food as Dietary Interventions for Arthritis and Related Inflammatory Diseases, Elsevier, p 319-336, 2013.
93. Lee S C, Yang Y H, Chuang S Y, Huang S Y, Pan W H. Reduced medication use and improved pulmonary function with supplements containing vegetable and fruit concentrate, fish oil and probiotics in asthmatic school children: a randomised controlled trial, British Journal of Nutrition 110(1): 145-55, 2013.
94. Nagel G, Weinmayr G, Kleiner A, Garcia-Marcos L, Strachan D P, Group IPTS. Effect of diet on asthma and allergic sensitisation in the International Study on Allergies and Asthma in Childhood (ISAAC) Phase Two, Thorax 65(6): 516-22, 2010.
95. Nyanhanda T, Gould E M, McGhie T, Shaw O M, Harper J L, Hurst R D. Blackcurrant cultivar polyphenolic extracts suppress CCL26 secretion from alveolar epithelial cells, Food Funct 5(4): 671-7, 2014.
96. Sawyer G M, Stevenson D E, McGhie T K, Hurst R D. Suppression of CCL26 and CCL11 generation in human alveolar epithelial cells by apple extracts containing procyanidins, J Funct Foods 31: 141-151, 2017.
97. Shaw O M, Nyanhanda T, McGhie T K, Harper J L, Hurst R D. Blackcurrant anthocyanins modulate CCL11 secretion and suppress allergic airway inflammation, Mol Nutr Food Res, 61(9): 1600868, 2017.
98. Slimestad R I, Solheim H. J. Anthocyanins from black currants (*Ribes nigrum* L.), J Agric Food Chem, 50(11): 3228-3231, 2002.

99. Matsumoto, H et al. Preparative-Scale isolation of four anthocyanin components of black currant (*Ribes nigrum* L.) fruits, J Agric Food Chem, 49(3): 1541-1545, 2001.
100. Spanos, G A and Wrolstad, R E. Influence of processing and storage on the phenolic composition of Thompson Seedless grape juice, J Agric Food Chem, 38(7): 1565-1571, 1990.

What is claimed is:

1. A method for:
   (i) treating an airway inflammation in a subject in need thereof;
   (ii) treating accumulation of collagen fibres in lung tissue of a subject in need thereof; or
   (iii) treating immune cell infiltration in lung tissue of a subject in need thereof;
   the method comprising administering to the subject a nutraceutical composition comprising:
      a Boysenberry and apple concentrate comprising at least 27% Boysenberry concentrate, wherein the Boysenberry and apple concentrate comprises at least 145 mg/100 g anthocyanin content, and wherein anthocyanins in the Boysenberry and apple concentrate account for at least 40% of the total polyphenol content of the Boysenberry and apple concentrate; and
      a Boysenberry, apple, and blackcurrant concentrate comprising at least 13.5% Boysenberry concentrate, wherein the Boysenberry, apple, and blackcurrant concentrate comprises at least 236 mg/100 g anthocyanin content, and wherein anthocyanins in the Boysenberry, apple, and blackcurrant concentrate account for at least 65% of the total polyphenol content of the Boysenberry, apple, and blackcurrant concentrate.

2. The method of claim 1, wherein the nutraceutical composition is administered to the subject once per day.

3. The method of claim 1, wherein the nutraceutical composition comprises a dosage unit comprising about 5 mg to about 500 mg total anthocyanins.

4. The method of claim 1, wherein the nutraceutical composition is administered enterally or orally.

5. The method of claim 1, wherein the nutraceutical composition is administered as a syrup, drop, gel, jelly, tablet, or capsule.

6. The method of claim 1, wherein the nutraceutical composition is administered at:
   (i) a dosage of about 0.1 mg/kg to about 10 mg/kg total anthocyanins per the subject's body weight; or
   (ii) a dosage of about 0.1 mg/kg to about 5 mg/kg total anthocyanins per subject's body weight; or
   (iii) a dosage of about 10 mg to about 200 mg total anthocyanins per day.

7. The method of claim 1, wherein the nutraceutical composition further comprises added polyphenols.

8. The method of claim 1, wherein the nutraceutical composition is administered with a respiratory aid.

9. The method of claim 8, wherein the further respiratory aid is a medication, a herbal remedy, or an essential oil.

10. The method of claim 8, wherein the further respiratory aid has one or more of anti-inflammatory, anti-spasmodic, bronchodilation, or muscle relaxation effects.

11. The method of claim 1, wherein the subject has a chronic respiratory disorder.

12. The method of claim 1, wherein the subject has allergic airways inflammation or reactive airway disease.

13. The method of claim 1, wherein the immune cell is selected from the group consisting of monocytes, eosinophils, neutrophils, and antigen presenting cells.

14. The method of claim 1, wherein the nutraceutical composition is administered to the subject at a dosage of (i) about 10 mg to about 200 mg total Boysenberry anthocyanins per day, or (ii) about 10 mg to about 200 mg total Boysenberry and blackcurrant anthocyanins per day.

15. The method of claim 1, wherein a juice concentrate volume in the nutraceutical composition is adjusted to include less than 1% v/v preservative.

\* \* \* \* \*